United States Patent
Le Hir de Fallois et al.

(10) Patent No.: US 9,776,999 B2
(45) Date of Patent: Oct. 3, 2017

(54) ANTIPARISITIC DIHYDROAZOLE COMPOUNDS AND COMPOSITIONS COMPRISING SAME

(71) Applicant: MERIAL, INC., Duluth, GA (US)

(72) Inventors: Loic Patrick Le Hir de Fallois, Atlanta, GA (US); Hyoung Ik Lee, Cary, NC (US); Douglas Edward Wilkinson, Wake Forest, NC (US); Brent Christopher Beck, US, GA (US)

(73) Assignee: MERIAL INC., Duluth, GA (US)

(*) Notice: Subject to any disclaimer, the term of this patent is extended or adjusted under 35 U.S.C. 154(b) by 0 days.

(21) Appl. No.: 15/191,163

(22) Filed: Jun. 23, 2016

(65) Prior Publication Data

US 2017/0022197 A1  Jan. 26, 2017

Related U.S. Application Data

(60) Continuation of application No. 14/658,668, filed on Mar. 16, 2015, now Pat. No. 9,376,434, which is a continuation of application No. 14/086,712, filed on Nov. 21, 2013, now Pat. No. 8,980,893, which is a division of application No. 12/970,670, filed on Dec. 16, 2010, now Pat. No. 8,618,126.

(60) Provisional application No. 61/287,545, filed on Dec. 17, 2009.

(51) Int. Cl.

| | |
|---|---|
| A61K 31/495 | (2006.01) |
| A61K 31/365 | (2006.01) |
| C07D 471/04 | (2006.01) |
| A01N 43/90 | (2006.01) |
| A01N 43/80 | (2006.01) |
| A61K 31/437 | (2006.01) |
| A61K 38/05 | (2006.01) |
| A61K 45/06 | (2006.01) |
| C07K 5/06 | (2006.01) |

(52) U.S. Cl.
CPC .......... *C07D 471/04* (2013.01); *A01N 43/80* (2013.01); *A01N 43/90* (2013.01); *A61K 31/365* (2013.01); *A61K 31/437* (2013.01); *A61K 31/495* (2013.01); *A61K 38/05* (2013.01); *A61K 45/06* (2013.01); *C07K 5/06* (2013.01)

(58) Field of Classification Search
CPC ............................ A61K 31/495; A61K 31/365
USPC .......................................... 514/300, 303, 246
See application file for complete search history.

(56) References Cited

U.S. PATENT DOCUMENTS

| 6,228,868 | B1 | 5/2001 | Gwaltney et al. ............ 514/300 |
| 2007/0066617 | A1 | 3/2007 | Mita et al. .................... 514/241 |
| 2009/0156643 | A1 | 6/2009 | Mita et al. .................... 514/340 |
| 2010/0137612 | A1 | 6/2010 | Yaosaka et al. .............. 548/240 |
| 2010/0144797 | A1 | 6/2010 | Mita et al. .................... 514/340 |
| 2010/0298558 | A1 | 11/2010 | Mita et al. ...................... 544/60 |
| 2011/0009438 | A1 | 1/2011 | Mita et al. .................... 514/274 |
| 2011/0124858 | A1 | 5/2011 | Iwata et al. ................... 544/105 |
| 2011/0144349 | A1 | 6/2011 | Kousaka et al. ............. 548/240 |

FOREIGN PATENT DOCUMENTS

| EP | 1932836 | 6/2008 | .......... C07D 261/04 |
| JP | 6247969 | 9/1994 | ............ A01N 43/90 |
| JP | 2008/133273 | 6/2008 | .......... C07D 207/20 |
| JP | 2010/168367 | 8/2009 | ............ A01N 37/18 |
| JP | 2010/083883 | 4/2010 | .......... C07D 261/04 |
| JP | 2010/235590 | 10/2010 | ............ A01N 43/80 |
| WO | WO00/06556 | 2/2000 | .......... C07D 263/10 |
| WO | WO2005/085216 | 9/2005 | ............ A01N 43/80 |
| WO | WO2007/070606 | 6/2007 | ............ A01N 43/80 |
| WO | WO2007/075459 | 7/2007 | |
| WO | WO2007/079162 | 7/2007 | ............ A01N 43/80 |
| WO | WO2007/123855 | 11/2007 | ............ A01N 43/80 |
| WO | WO2007/125984 | 11/2007 | ............ A01N 43/80 |
| WO | WO2008/019760 | 2/2008 | ............ A01N 43/80 |
| WO | WO2008/108448 | 9/2008 | ............ A01N 43/80 |
| WO | WO2008/122375 | 10/2008 | |
| WO | WO2008/126665 | 10/2008 | ............ A01N 43/80 |
| WO | WO2008/128711 | 10/2008 | ............ A01N 43/36 |
| WO | WO2008/130651 | 10/2008 | ............ A01N 43/80 |
| WO | WO2008/150393 | 12/2008 | .......... C07D 413/10 |
| WO | WO2008/154528 | 12/2008 | ............ A01N 43/80 |
| WO | WO2009/001942 | 12/2008 | ............ C07B 61/00 |
| WO | WO2009/002809 | 12/2008 | |

(Continued)

OTHER PUBLICATIONS

"Synthesis and Biological Evaluation of 2-Indolyloxazolines as a New Class of TubulinPolymerization Inhibitors. Discovery of A-289099 as an Orally Active AntitumorAgent" Li et al., Bioorganic & Medicinal Chemistry Letters (2002),12(3), 465-469.

(Continued)

*Primary Examiner* — Niloofar Rahmani
(74) *Attorney, Agent, or Firm* — Judy Jarecki-Black; John Ezcurra; Merial Inc.

(57) ABSTRACT

The present invention relates to novel dihydroazole of formula (I) and salts thereof:

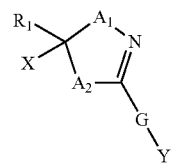

Wherein $R_1$, $A_1$, $A_2$, G, X and Y are as defined in the description, compositions thereof, processes for their preparation and their uses to prevent or treat parasitic infections or infestations in animals and as pesticides.

29 Claims, No Drawings

(56) References Cited

FOREIGN PATENT DOCUMENTS

| WO | WO2009/003075 | 12/2008 | A61K 31/42 |
|----|---------------|---------|------------|
| WO | WO2009/022746 | 2/2009  | A01N 43/80 |
| WO | WO2009/024541 | 2/2009  | A01N 43/80 |
| WO | WO2009/025983 | 2/2009  | C07D 261/04 |
| WO | WO2009/035004 | 3/2009  | A01N 43/80 |
| WO | WO2009/045999 | 4/2009  | C07D 261/04 |
| WO | WO2009/049845 | 4/2009  | A01N 37/46 |
| WO | WO2009/049846 | 4/2009  | A01N 43/80 |
| WO | WO2009/051956 | 4/2009  | C07D 413/10 |
| WO | WO2009/072621 | 6/2009  | A01N 43/36 |
| WO | WO2009/097992 | 8/2009  | A01N 43/36 |
| WO | WO2009/112275 | 9/2009  | C07D 207/20 |
| WO | WO2009/126668 | 10/2009 | C07D 25/13 |
| WO | WO2010/005048 | 1/2010  | C07D 261/04 |
| WO | WO2010/020521 | 2/2010  | A01N 43/80 |
| WO | WO2010/020522 | 2/2010  | A01N 43/80 |
| WO | WO2010/027051 | 3/2010  | C07C 233/31 |
| WO | WO2010/043315 | 4/2010  | A01N 43/36 |
| WO | WO2010/070068 | 6/2010  | A01N 43/80 |
| WO | WO2010/072781 | 7/2010  | A01N 43/80 |
| WO | WO2010/079077 | 7/2010  | A01N 43/80 |
| WO | WO2010/084067 | 7/2010  | A01N 43/80 |
| WO | WO2010/086225 | 8/2010  | A01N 43/80 |
| WO | WO2010/090344 | 8/2010  | A01N 35/00 |
| WO | WO2010/108733 | 9/2010  | A01N 43/80 |
| WO | WO2010/112545 | 10/2010 | A01N 43/80 |

OTHER PUBLICATIONS

"Diagnosis of parasitic diseases: old and new approaches," Momar Ndao, Interdisciplinary Perspectives on Infectious Diseases, vol. 2009, Article ID 278246, 15 pags doi: 10.1155/2009/278246.

"Antiparasitic isoxazoline: Novel Chemistry of Ligand-gated Chloride Channel Blockers" Yoshihisa Ozoe et al., Abstracts of Papers, 238th ACS National Meeting, Washington, DC, United States, Aug. 16-20, 2009, AGRO-051.

"Isoxazoline Insecticides", George Lahm et al., 238th ACS National Meeting, Washington, DC, United States, Aug. 16-20, 2009, AGRO-159.

"A Novel Cu-Assisted Cycloisomerization of Alkynyl Imines: Efficient Synthesis of Pyrroles and Pyrrole-Containing Heterocycles", Gevorgyan et al., J. Am. Chem. Soc. 2001, 123, 2074-2075.

"Gold-Catalyzed 1,2-Migration of Silicon, Tin, and Germanium en Route to C-2 Substituted Fused Pyrrole-Containing Heterocycles", Ilya V. Seregin and Vladimir Gevorgyan, J. Am. Chem. Soc., 2006, 128(37), 12050-12051.

"Mechanistically Diverse Copper-, Silver-, and Gold-Catalyzed Acyloxy and Phosphatyloxy Migrations: Efficient Synthesis of Heterocycles via Cascade Migration/Cycloisomerization Approach", Gevorgyan et al., J. Am. Chem. Soc., 2007, 129, 9868-9878.

"Base- and Ligand-free Room-Temperature Synthesis of N-Fused Heteroaromatic Compounds via the Transition Metal-Catalyzed Cycloisomerization Protocol", Gevorgyan et al., Org. Lett., 2007, 9(17), 3433-3436.

"Low Temperature Organocopper-Mediated Two-Component Cross Coupling/Cycloisomerization Approach Toward N-Fused Heterocycles", Gevorgyan et al., Org. Lett., 2008, 10(11), 2307-2310.

"Electronic Effects in the Pt-Catalyzed Cycloisomerization of Propargylic Esters: Synthesis of 2,3-Disubstituted Indolizines as a Mechanistic Probe", Hardin and Sarpong, Org. Lett., 2007, 9(22), 4547-4550.

"Direct Synthesis of Monofunctionalized Indolizine Derivatives Bearing Alkoxymethyl Substituents at C-3 and Their Benzofused Analogues", Kaloko and Hayford, Org. Lett., 2005, 7(19), 4305-4308.

"Mechanistic Investigation on the Formation of Indolizines from 2-Enynylpyridines", Lahoz et al., Org. Lett., 2009, 11(21), 4802-4805.

"Development of a Practical Synthesis of STA-5312, a Novel Indolizine Oxalylamide Microtubule Inhibitor", Li et al., Organic Process Research & Development, 2007, 11, 246-250.

"General and Direct Synthesis of 3-Aminoindolizines and Their Analogues via Pd/Cu-Catalyzed Sequential Cross-Coupling/Cycloisomerization Reactions", Liu et al., Org. Lett., 2007, 9(3), 409-412.

"The antiparasitic isoxazoline A1443 is a potent blocker of insect ligand-gated chloride channels", Ozoe et al., Biochemical and Biophysical Research Communications, 2010, 391, 744-749.

"Pt-Catalyzed Cyclization/1,2-Migration for the Synthesis of Indolizines, Pyrrolones, and Indolizinones", Smith et al., Org. Lett., 2007, 9(6), 1169-1171.

"Highly Efficient Synthesis of Functionalized Indolizines and Indolizinones by Copper-Catalyzed Cycloisomerizations of Propargylic Pyridines", Yan et al., J. Org. Chem. 2007, 72, 7783-7786.

"Gold-Catalyzed Multicomponent Synthesis of Aminoindolizines from Aldehydes, Amines, and Alkynes under Solvent-Free Conditions or in Water", Liu et al., Org. Lett., 2007, 9(21), 4323-4326.

ANTIPARISITIC DIHYDROAZOLE COMPOUNDS AND COMPOSITIONS COMPRISING SAME

CROSS REFERENCE TO RELATED APPLICATIONS

This application is a continuation of U.S. patent application Ser. No. 14/658,668, filed on Mar. 16, 2015, now U.S. Pat. No. 9,376,434; which is a continuation of U.S. patent application Ser. No. 14/086,712, filed on Nov. 21, 2013, now U.S. Pat. No. 8,980,893; which is a division of U.S. patent application Ser. No. 12/970,670, now U.S. Pat. No. 8,618,126; which claims the benefit of priority to U.S. Provisional Application No. 61/287,545 filed Dec. 17, 2009, all of which are incorporated herein by reference in their entirety.

FIELD OF THE INVENTION

The present invention relates to novel paraciticidal dihydroazole compounds of formula (I):

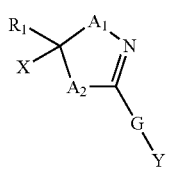

(I)

wherein, $R_1$, $A_1$, $A_2$, G, X and Y are as defined below, and compositions comprising at least one compound of formula (I) in combination with a pharmaceutically acceptable or agriculturally acceptable carrier. The invention also relates to uses of the compounds and methods comprising the compounds for the treatment and prevention of parasitic infections or infestations and for controlling pests in crops, plants, plant propagation material and material derived from wood.

BACKGROUND OF THE INVENTION

Various patent publications have described isoxazoline derivatives having pesticidal properties, compositions comprising these compounds and use of the compounds in the fields of agriculture and veterinary medicine. International Patent Publication Nos. WO2009/072621, WO 2009/001942, WO 2009/024541, WO 2009/035004, WO 2008/108448, WO 2005/085216, WO 2007/075459, WO 2007/079162, WO 2008/150393, WO 2008/154528, WO 2009/002809, WO 2009/003075, WO 2009/045999, WO 2009/051956, WO 2009/02451, WO 2008/122375, WO 2007/125984, WO 2008/130651, WO 2009/022746, JP 2008/133273, WO 2008/126665, WO 2009/049846 and WO 2008/019760 describe pesticidal isoxazoline derivatives, compositions comprising the compounds and uses of the compounds against parasites and pests that harm animals and plants.

More recently, International Patent Publication Nos. WO 2009/141093, WO 2010/027051, WO 2010/005048, WO 2009/049845, WO 2009/04946, WO 2010/020521, WO 2010/020522, WO 2010/070068, WO 2010/084067, WO 2010/086225, WO 2010/108733, WO2010/070068, WO2010/079077, WO 2010/072781, WO2010/112545, WO2009/025983, WO2009/126668 and WO2010/090344 and Japanese Patent Publication Nos. JP2010/235590 and JP2010/168367 have also described isoxazoline derivatives having pesticidal activity and compositions comprising these compounds.

WO 2009/097992 describes arylpyrrolines with pesticidal activity, and WO 2008/128711 and WO 2010/043315, describes aryl pyrrolidines that are active against pests. WO 2009/112275 describes condensed ring aryl compounds with pesticidal activity.

Although some of these publications describe compounds containing a substituted isoxazoline ring having pesticidal and parasiticidal properties, none of the foregoing publications describe compounds of formula (I), that possess parasiticidal and pesticidal activity, particularly for controlling endoparasites or ectoparasites in or on animals.

The foregoing documents and all documents cited therein or during their prosecution ("application cited documents") and all documents cited or referenced in the application cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention.

Citation or identification of any document in this application is not an admission that such document is available as prior art to the present invention.

SUMMARY OF THE INVENTION

The present invention provides novel and inventive dihydroazole compounds of formula (I) that are biologically active against endoparasites and ectoparasites that harm animals and against pests that damage crops, plants, plant propagation material and material derived from wood. Accordingly, the application provides parasiticidal and pesticidal compositions comprising the dihydroazole compounds in combination with a pharmaceutically acceptable carrier or an agriculturally acceptable carrier. The present invention also provides methods for the treatment or prevention of a parasitic infection or infestation in an animal and for controlling pests that harm plants, plant propagation material and material derived from wood, which comprise administering an effective amount of a compound of the invention to the animal or to the plants, or the soil in which the infected plant grows, or the wood-derived material, with a pesticidally effective amount of a compound of formula (I).

A first object of the invention is to provide parasiticidal and pesticidal novel and inventive dihydroazole compounds of formula (I):

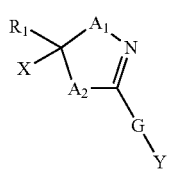

(I)

wherein:

$R_1$ is hydrogen, halogen, —CN, or alkyl, haloalkyl, alkenyl, haloalkenyl, alkynyl, haloalkynyl, cycloalkyl, halocycloalkyl, alkylcycloalkyl or cycloalkylalkyl, each which is unsubstituted or substituted with one or more of halogen, hydroxy, amino, alkyl- or di(alkyl)amino, alkyl, cycloalkyl, haloalkyl, alkenyl, haloalkenyl, alkynyl, haloalkynyl, alkoxy, haloalkoxy, alkylthio, haloalkylthio, $R_7S(O)$—, $R_7S(O)_2$—, $R_7C(O)$—, $R_7R_8NC(O)$—, $R_7OC(O)$—, $R_7C(O)O$—, $R_7C(O)NR_8$—, —CN or —NO$_2$;

X is aryl or heteroaryl, which may be unsubstituted or substituted by one or more of halogen, hydroxy, amino, alkyl- or di(alkyl)amino, alkyl, cycloalkyl, haloalkyl, alkenyl, haloalkenyl, alkynyl, haloalkynyl, alkoxy, haloalkoxy, alkylthio, haloalkylthio, $R_7S(O)$—, $R_7S(O)_2$—, $R_7C(O)$—, $R_7R_8NC(O)$—, $R_7OC(O)$—, $R_7C(O)O$—, $R_7C(O)NR_8$—, —CN or —NO$_2$;

$A_1$ and $A_2$ are independently oxygen, $NR_2$ or $CR_7R_8$;

G is G-1 or G-2;

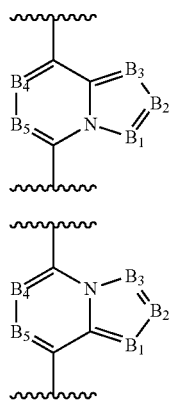

G-1

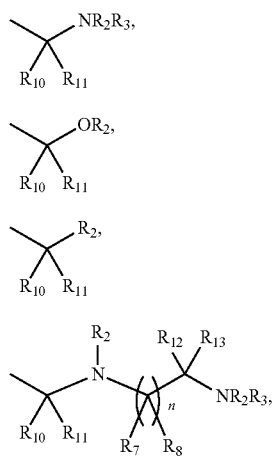

G-2

$B_1$, $B_2$, $B_3$, $B_4$ and $B_5$ are independently N or C—$R_9$;

Y is hydrogen, halogen, —CN; or Y is alkyl, haloalkyl, alkenyl, haloalkenyl, alkynyl, haloalkynyl, cycloalkyl, alkylcycloalkyl, cycloalkylalkyl, aryl, heterocyclyl or heteroarylm each of which is unsubstituted or substituted with one or more of halogen, hydroxy, amino, alkyl- or di(alkyl)amino, alkyl, cycloalkyl, haloalkyl, alkenyl, haloalkenyl, alkynyl, haloalkynyl, alkoxy, haloalkoxy, alkylthio, haloalkylthio, $R_7S(O)$—, $R_7S(O)_2$—, $R_7C(O)$—, $R_7R_8NC(O)$—, $R_7OC(O)$—, $R_7C(O)O$—, $R_7C(O)NR_8$—, —CN or —NO$_2$; or Y is Y-1, Y-2, Y-3, Y-4, Y-5, Y-6, Y-7, Y-8, Y-9, Y-10, Y-11, Y-12 or Y-13;

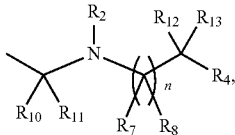

Y-1

Y-2

Y-3

Y-4

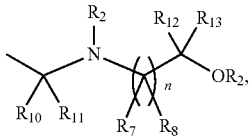

Y-5

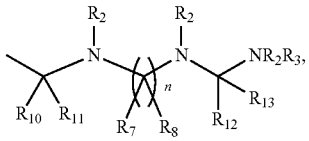

Y-6

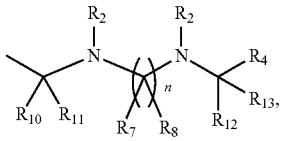

Y-7

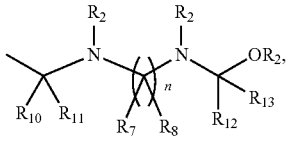

Y-8

Y-9

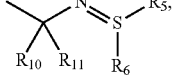

Y-10

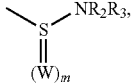

Y-11

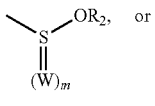

Y-12 or

Y-13

$R_2$, $R_3$ are independently hydrogen, alkyl, haloalkyl, thioalkyl, alkylthioalkyl, hydroxyalkyl, alkoxylakyl, alkenyl, haloalkenyl, alkynyl, haloalkynyl, cycloalkyl, $R_{10}S(O)$—, $R_{10}S(O)_2$—, $R_{10}C(O)$—, $R_{10}C(S)$—, $R_{10}R_{11}NC(O)$—, $R_{10}R_{11}NC(S)$—$R_{10}OC(O)$—;

$R_4$, $R_5$ and $R_6$ are independently hydrogen, alkyl, haloalkyl, thioalkyl, alkylthioalkyl, hydroxyalkyl, alkoxylakyl, alkenyl, haloalkenyl, alkynyl, haloalkynyl, cycloalkyl, aryl or heteroaryl;

$R_7$ and $R_8$ are independently hydrogen, alkyl, haloalkyl, thioalkyl, alkylthioalkyl, hydroxyalkyl, alkoxylakyl, alkenyl, haloalkenyl, alkynyl or haloalkynyl;

$R_9$ is hydrogen, halogen, —CN, or alkyl, haloalkyl, alkenyl, haloalkenyl, alkynyl, haloalkynyl, cycloalkyl, halocycloalkyl, alkylcycloalkyl or cycloalkylalkyl, each which is unsubstituted or substituted with one or more of halogen, hydroxy, amino, alkyl- or di(alkyl)amino, alkyl, cycloalkyl, haloalkyl, alkenyl, haloalkenyl, alkynyl, haloalkynyl, alkoxy, haloalkoxy, alkylthio, haloalkylthio, $R_7S(O)-$, $R_7S(O)_2-$, $R_7C(O)-$, $R_7R_8NC(O)-$, $R_7OC(O)-$, $R_7C(O)O-$, $R_7C(O)NR_8-$, $-CN$ or $-NO_2$;

$R_{10}$, $R_{11}$, $R_{12}$ and $R_{13}$ are each independently hydrogen, alkyl, haloalkyl, thioalkyl, alkylthioalkyl, hydroxyalkyl, alkoxylakyl, alkenyl, haloalkenyl, alkynyl or haloalkynyl; or $R_{10}$ together with $R_{11}$ form $=O$, $=S$ or $=NR_2$;
$R_{12}$ together with $R_{13}$ form $=O$, $=S$ or $=NR_2$;
W is O, S or $NR_2$;
n is 1-4; and
m is 0, 1 or 2.

Further, this invention provides for antiparasitic compositions for the treatment or prevention of parasitic infections and infestations in animals comprising a parasiticidally effective amount of the compounds of formula (I) in combination with a pharmaceutically acceptable carrier. The compositions may be formulated for oral, subcutaneous, parenteral, and topical administration including spot-on and pour-on administration.

Another object of the invention is to provide pesticidal compositions comprising a compound of formula (I) for combating pests that are harmful to plants, plant propagation material or material derived from wood in combination with a pesticidally effective carrier.

Another object of the invention is to provide veterinary and agricultural compositions for combating pests and parasites comprising a pesticidally or parasiticidally effective amount of the compounds of the invention, or veterinarily or agriculturally acceptable salts thereof, in combination with one more other active agent and a veterinarily or agriculturally acceptable carrier or diluent.

Another object of the invention is to provide plant propagation material (e.g. seed), comprising at least one compound of formula (I) or agriculturally acceptable salts thereof, and plant propagation material that has been treated with a compound of formula (I) or a composition comprising the compound.

Another object of this invention is to provide methods of treatment and prevention of parasitic infections or infestations in or on an animal, which comprise treating the infected animal with a parasiticidally effective amount of a compound of formula (I).

Another object of this invention is to provide methods for combating pests on crops, plants, plant propagation material or material derived from wood, which comprises treating the infected plant, or the soil in which the infected plant grows, or the wood-derived material with a pesticidally effective amount of a compound of formula (I).

Another object of the invention is to provide methods for combating or controlling pests at a locus, comprising administering a pesticidally or parasiticidally effective amount of a compound of formula (I), or veterinarily or agriculturally acceptable salts thereof, to the locus.

Another object of the invention is to provide use of a compound of formula (I) in the treatment or prevention of a parasitic infection or infestation in or on an animal. Still another object of the invention is use of a compound of formula (I) in the preparation of a medicament for the treatment or prevention of a parasitic infestation or infection in or on an animal.

Still another object of this invention is to provide processes for the preparation of dihydroazole compounds of formula (I).

The present invention does not intend to encompass within the scope of the invention any previously disclosed compound, product, process of making the product or method of using the product, which meets the written description and enablement requirements of the USPTO (35 U.S.C. 112, first paragraph) or the EPO (Article 83 of the EPC), such that the applicant(s) reserve the right and hereby disclose a disclaimer of any previously described product, method of making the product or process of using the product. It is therefore an intention of the invention to not explicitly cover compounds, products, processes of making products or compounds, or methods of using products or compounds that are explicitly disclosed in the prior art or whose novelty is destroyed by prior art, including without limitation any prior art herein mentioned; and the applicant(s) explicitly reserve the right to introduce into any claim a disclaimer as to any previously disclosed compound, product, process of making the product or method of using the product. Specifically, the compounds of the invention are not intended to encompass dihydroazole compounds that have been previously disclosed in the art.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law; e.g., they allow for elements not explicitly recited, but exclude elements that are found in the prior art or that affect a basic or novel characteristic of the invention.

These and other embodiments are disclosed or are obvious from and encompassed by, the following Detailed Description.

DETAILED DESCRIPTION OF THE INVENTION

The novel and inventive dihydroazole compounds of the invention have been found to have superior activity against pests, including parasites that cause harm to animals, and pests that damage plants, plant propagation material and material containing wood or derived from wood. It has been surprisingly been found that the dihydroazole compounds of the invention are highly efficacious against pests and parasites. Accordingly, the compounds of the invention have been found useful for preventing and treating a parasitic infestation/infection in an animal and for controlling and eradicating pests that damage plants, plant propagation material and material derived from wood.

The present invention provides novel and inventive dihydroazole compounds and compositions comprising the compounds. Furthermore, the invention provides methods for preventing and/or treating a parasitic infestation or infection in an animal, and the use of the compounds for treating a parasitic infestation or infection in an animal or the use of the compounds in the manufacture of a medicament for treating a parasitic infestation or infection in an animal. The compounds of the present invention have been surprisingly been found to have potent activity against both ectoparasites and endoparasites that harm animals. In one embodiment, the compounds of the invention may be used for the prevention and/or treatment of endoparasitic infections of animals, including infections by parasitic nematodes. In another embodiment, the compounds of the invention are used for the prevention and/or treatments of endoparasitic infections of animals by *Dirofilaria immitis*.

In another embodiment, the present invention provides uses of the compounds for controlling and eradicating pests that cause damage to plants, plant propagation material and material derived from wood.

A first object of the invention is to provide parasiticidal and pesticidal novel and inventive dihydroazole compounds of formula (I):

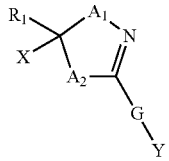
(I)

wherein:

$R_1$ is hydrogen, halogen, —CN, or alkyl, haloalkyl, alkenyl, haloalkenyl, alkynyl, haloalkynyl, cycloalkyl, halocycloalkyl, alkylcycloalkyl or cycloalkylalkyl, each which is unsubstituted or substituted with one or more of halogen, hydroxy, amino, alkyl- or di(alkyl)amino, alkyl, cycloalkyl, haloalkyl, alkenyl, haloalkenyl, alkynyl, haloalkynyl, alkoxy, haloalkoxy, alkylthio, haloalkylthio, $R_7S(O)$—, $R_7S(O)_2$—, $R_7C(O)$—, $R_7R_8NC(O)$—, $R_7OC(O)$—, $R_7C(O)O$—, $R_7C(O)NR_8$—, —CN or —NO$_2$;

X is aryl or heteroaryl, which may be unsubstituted or substituted by one or more of halogen, hydroxy, amino, alkyl- or di(alkyl)amino, alkyl, cycloalkyl, haloalkyl, alkenyl, haloalkenyl, alkynyl, haloalkynyl, alkoxy, haloalkoxy, alkylthio, haloalkylthio, $R_7S(O)$—, $R_7S(O)_2$—, $R_7C(O)$—, $R_7R_8NC(O)$—, $R_7OC(O)$—, $R_7C(O)O$—, $R_7C(O)NR_8$—, —CN or —NO$_2$;

$A_1$ and $A_2$ are independently oxygen, $NR_2$ or $CR_7R_8$;

G is G-1 or G-2;

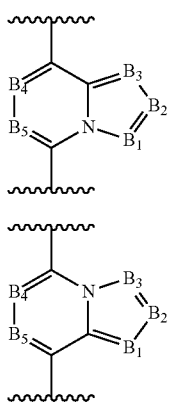

$B_1$, $B_2$, $B_3$, $B_4$ and $B_5$ are independently N or C—$R_9$;

Y is hydrogen, halogen, —CN; or Y is alkyl, haloalkyl, alkenyl, haloalkenyl, alkynyl, haloalkynyl, cycloalkyl, alkylcycloalkyl, cycloalkylalkyl, aryl, or heterocyclyl or heteroaryl each of which is unsubstituted or substituted with one or more of halogen, hydroxy, amino, alkyl- or di(alkyl)amino, alkyl, cycloalkyl, haloalkyl, alkenyl, haloalkenyl, alkynyl, haloalkynyl, alkoxy, haloalkoxy, alkylthio, haloalkylthio, $R_7S(O)$—, $R_7S(O)_2$—, $R_7C(O)$—, $R_7R_8NC(O)$—, $R_7OC(O)$—, $R_7C(O)O$—, $R_7C(O)NR_8$—, —CN or —NO$_2$; or Y is Y-1, Y-2, Y-3, Y-4, Y-5, Y-6, Y-7, Y-8, Y-9, Y-10, Y-11, Y-12 or Y-13;

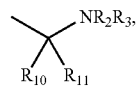
Y-1

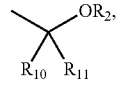
Y-2

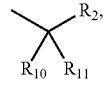
Y-3

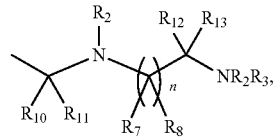
Y-4

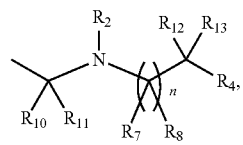
Y-5

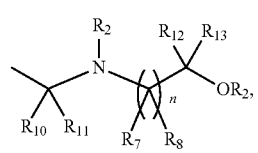
Y-6

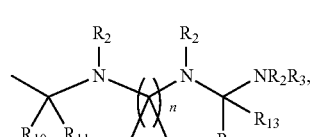
Y-7

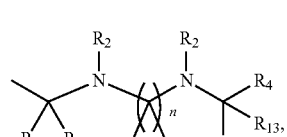
Y-8

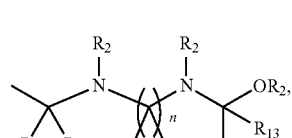
Y-9

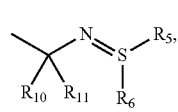
Y-10

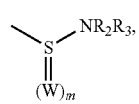
Y-11

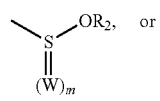
Y-12

-continued

Y-13

$R_2$, $R_3$ are independently hydrogen, alkyl, haloalkyl, thioalkyl, alkylthioalkyl, hydroxyalkyl, alkoxylakyl, alkenyl, haloalkenyl, alkynyl, haloalkynyl, cycloalkyl, $R_{10}S(O)$—, $R_{10}S(O)_2$—, $R_{10}C(O)$—, $R_{10}C(S)$—, $R_{10}R_{11}NC(O)$—, $R_{10}R_{11}NC(S)$—$R_{10}OC(O)$—, $R_4$, $R_5$ and $R_6$ are independently hydrogen, alkyl, haloalkyl, thioalkyl, alkylthioalkyl, hydroxyalkyl, alkoxylakyl, alkenyl, haloalkenyl, alkynyl, haloalkynyl, cycloalkyl, aryl or heteroaryl;

$R_7$ and $R_8$ are independently hydrogen, alkyl, haloalkyl, thioalkyl, alkylthioalkyl, hydroxyalkyl, alkoxylakyl, alkenyl, haloalkenyl, alkynyl or haloalkynyl;

$R_9$ is hydrogen, halogen, —CN, or alkyl, haloalkyl, alkenyl, haloalkenyl, alkynyl, haloalkynyl, cycloalkyl, halocycloalkyl, alkylcycloalkyl or cycloalkylalkyl, each which is unsubstituted or substituted with one or more of halogen, hydroxy, amino, alkyl- or di(alkyl)amino, alkyl, cycloalkyl, haloalkyl, alkenyl, haloalkenyl, alkynyl, haloalkynyl, alkoxy, haloalkoxy, alkylthio, haloalkylthio, $R_7S(O)$—, $R_7S(O)_2$—, $R_7C(O)$—, $R_7R_8NC(O)$—, $R_7OC(O)$—, $R_7C(O)O$—, $R_7C(O)NR_8$—, —CN or —$NO_2$;

$R_{10}$, $R_{11}$, $R_{12}$ and $R_{13}$ are each independently hydrogen, alkyl, haloalkyl, thioalkyl, alkylthioalkyl, hydroxyalkyl, alkoxylakyl, alkenyl, haloalkenyl, alkynyl or haloalkynyl; or $R_{10}$ together with $R_{11}$ form =O, =S or =$NR_2$; or
$R_{12}$ together with $R_{13}$ form =O, =S or =$NR_2$;
W is O, S or $NR_2$;
n is 1-4; and
m is 0, 1 or 2.

In one embodiment, the invention provides compounds of formula (I), wherein G is G-1. In another embodiment, the invention provides compounds of formula (I), wherein G is G-2.

In still another embodiment, the invention provides compounds of formula (I), wherein $R_1$ is alkyl, haloalkyl, alkenyl, haloalkenyl, alkynyl or haloalkynyl.

In another embodiment, the invention provides compounds of formula (I), wherein $A_1$ is oxygen and $A_2$ is $CR_7R_8$.

In another embodiment of the invention, a compound of formula (I) is provided wherein $A_1$ is oxygen and $A_2$ is $CR_7R_8$, $R_1$ is $C_1$-$C_4$alkyl or $C_1$-$C_4$haloalkyl, and X is aryl.

In another embodiment of the invention, a compound of formula (I) is provided wherein $A_1$ is oxygen and $A_2$ is $NR_2$, $R_1$ is $C_1$-$C_4$alkyl or $C_1$-$C_4$haloalkyl, and X is aryl.

In another embodiment of the invention, a compound of formula (I) is provided wherein $A_1$ is $CR_7R_8$ and $A_2$ is oxygen, $R_1$ is $C_1$-$C_4$alkyl or $C_1$-$C_4$haloalkyl, and X is aryl.

In yet another embodiment, the invention provides a compound of formula (I) wherein $A_1$ is oxygen and $A_2$ is $CR_7R_8$, $R_1$ is $C_1$-$C_4$alkyl or $C_1$-$C_4$haloalkyl, and X is heteroaryl.

In another embodiment, a compound of formula (I) is provided wherein $R_{10}$ and $R_{11}$ together form =O, =S or =$NR_2$.

In still another embodiment of the invention, a compound of formula (I) is provided wherein $R_{12}$ and $R_{13}$ together form =O, =S or =$NR_2$.

In another embodiment of the invention, a compound of formula (I) is provided wherein:
G is G-1;
$A_1$ is oxygen;
X is aryl;
$R_1$ is hydrogen, alkyl or haloalkyl; and
Y is Y-1, Y-2 or Y-3.

In another embodiment of the invention, a compound of formula (I) is provided wherein:
G is G-1;
$A_1$ is oxygen;
X is aryl;
$R_1$ is hydrogen, alkyl or haloalkyl; and
Y is Y-4, Y-5 or Y-6.

In yet another embodiment of the invention, a compound of formula (I) is provided wherein:
G is G-1;
$A_1$ is oxygen;
X is aryl;
$R_1$ is hydrogen, alkyl or haloalkyl; and
Y is Y-7, Y-8 or Y-9.

In still another embodiment, the invention provides a compound of formula (I) wherein:
G is G-1;
$A_1$ is oxygen;
X is aryl;
$R_1$ is hydrogen, alkyl or haloalkyl; and
Y is Y-10, Y-11, Y-12 or Y-13.

In another embodiment of the invention, a compound of formula (I) is provided wherein:
G is G-1;
$A_1$ is oxygen;
X is heteroaryl;
$R_1$ is hydrogen, alkyl or haloalkyl; and
Y is Y-1, Y-2 or Y-3.

In another embodiment of the invention, a compound of formula (I) is provided wherein:
G is G-1;
$A_1$ is oxygen;
X is heteroaryl;
$R_1$ is hydrogen, alkyl or haloalkyl; and
Y is Y-4, Y-5 or Y-6.

In yet another embodiment of the invention, a compound of formula (I) is provided wherein:
G is G-1;
$A_1$ is oxygen;
X is heteroaryl;
$R_1$ is hydrogen, alkyl or haloalkyl; and
Y is Y-7, Y-8 or Y-9.

In still another embodiment, the invention provides a compound of formula (I) wherein:
G is G-1;
$A_1$ is oxygen;
X is heteroaryl;
$R_1$ is hydrogen, alkyl or haloalkyl; and
Y is Y-10, Y-11, Y-12 or Y-13.

In another embodiment of the invention, a compound of formula (I) is provided wherein:
G is G-2;
$A_1$ is oxygen;
X is aryl;
$R_1$ is hydrogen, alkyl or haloalkyl; and
Y is Y-1, Y-2 or Y-3.

In another embodiment of the invention, a compound of formula (I) is provided wherein:
G is G-2;
$A_1$ is oxygen;

X is aryl;
$R_1$ is hydrogen, alkyl or haloalkyl; and
Y is Y-4, Y-5 or Y-6.

In yet another embodiment of the invention, a compound of formula (I) is provided wherein:
G is G-2;
$A_1$ is oxygen;
X is aryl;
$R_1$ is hydrogen, alkyl or haloalkyl; and
Y is Y-7, Y-8 or Y-9.

In still another embodiment, the invention provides a compound of formula (I) wherein:
G is G-2;
$A_1$ is oxygen;
X is aryl;
$R_1$ is hydrogen, alkyl or haloalkyl; and
Y is Y-10, Y-11, Y-12 or Y-13.

In another embodiment of the invention, a compound of formula (I) is provided wherein:
G is G-2;
$A_1$ is oxygen;
X is heteroaryl;
$R_1$ is hydrogen, alkyl or haloalkyl; and
Y is Y-1, Y-2 or Y-3.

In another embodiment of the invention, a compound of formula (I) is provided wherein:
G is G-2;
$A_1$ is oxygen;
X is heteroaryl;
$R_1$ is hydrogen, alkyl or haloalkyl; and
Y is Y-4, Y-5 or Y-6.

In yet another embodiment of the invention, a compound of formula (I) is provided wherein:
G is G-2;
$A_1$ is oxygen;
X is heteroaryl;
$R_1$ is hydrogen, alkyl or haloalkyl; and
Y is Y-7, Y-8 or Y-9.

In still another embodiment, the invention provides a compound of formula (I) wherein:
G is G-2;
$A_1$ is oxygen;
X is heteroaryl;
$R_1$ is hydrogen, alkyl or haloalkyl; and
Y is Y-10, Y-11, Y-12 or Y-13.

In still another embodiment, the invention provides a compound of formula (I) wherein:
G is G-1;
$A_1$ is oxygen;
X is aryl or heteroaryl;
$R_1$ is halogen, —CN, alkenyl, haloalkenyl, alkynyl or haloalkynyl; and
Y is Y-1, Y-2 or Y-3.

In another embodiment of the invention, a compound of formula (I) is provided wherein:
G is G-1;
$A_1$ is oxygen;
X is aryl or heteroaryl;
$R_1$ is halogen, —CN, alkenyl, haloalkenyl, alkynyl or haloalkynyl; and
Y is Y-4, Y-5 or Y-6.

In yet another embodiment of the invention, a compound of formula (I) is provided wherein:
G is G-1;
$A_1$ is oxygen;
X is aryl or heteroaryl;
$R_1$ is halogen, —CN, alkenyl, haloalkenyl, alkynyl or haloalkynyl; and
Y is Y-7, Y-8 or Y-9.

In still another embodiment, the invention provides a compound of formula (I) wherein:
G is G-1;
$A_1$ is oxygen;
X is aryl or heteroaryl;
$R_1$ is halogen, —CN, alkenyl, haloalkenyl, alkynyl or haloalkynyl; and
Y is Y-10, Y-11, Y-12 or Y-13.

In still another embodiment, the invention provides a compound of formula (I) wherein:
G is G-2;
$A_1$ is oxygen;
X is aryl or heteroaryl;
$R_1$ is halogen, —CN, alkenyl, haloalkenyl, alkynyl or haloalkynyl; and
Y is Y-1, Y-2 or Y-3.

In another embodiment of the invention, a compound of formula (I) is provided wherein:
G is G-2;
$A_1$ is oxygen;
X is aryl or heteroaryl;
$R_1$ is halogen, —CN, alkenyl, haloalkenyl, alkynyl or haloalkynyl; and
Y is Y-4, Y-5 or Y-6.

In yet another embodiment of the invention, a compound of formula (I) is provided wherein:
G is G-2;
$A_1$ is oxygen;
X is aryl or heteroaryl;
$R_1$ is halogen, —CN, alkenyl, haloalkenyl, alkynyl or haloalkynyl; and
Y is Y-7, Y-8 or Y-9.

In still another embodiment, the invention provides a compound of formula (I) wherein:
G is G-2;
$A_1$ is oxygen;
X is aryl or heteroaryl;
$R_1$ is halogen, —CN, alkenyl, haloalkenyl, alkynyl or haloalkynyl; and
Y is Y-10, Y-11, Y-12 or Y-13.

In another embodiment of the invention, a compound of formula (I) is provided wherein:
G is G-1;
$A_1$ is oxygen;
X is aryl;
$R_1$ is hydrogen, alkyl or haloalkyl; and
Y is aryl.

In yet another embodiment of the invention, a compound of formula (I) is provided wherein:
G is G-2;
$A_1$ is oxygen;
X is aryl;
$R_1$ is hydrogen, alkyl or haloalkyl; and
Y is aryl.

In another embodiment of the invention, a compound of formula (I) is provided wherein:
G is G-1;
$A_1$ is oxygen;
X is aryl;
$R_1$ is hydrogen, alkyl or haloalkyl; and
Y is heteroaryl.

In yet another embodiment of the invention, a compound of formula (I) is provided wherein:
G is G-2;
$A_1$ is oxygen;
X is aryl;
$R_1$ is hydrogen, alkyl or haloalkyl; and
Y is heteroaryl.

In another embodiment of the invention, a compound of formula (I) is provided wherein:
G is G-1;
$A_1$ is oxygen;
X is heteroaryl;
$R_1$ is hydrogen, alkyl or haloalkyl; and
Y is heteroaryl.

In yet another embodiment of the invention, a compound of formula (I) is provided wherein:
G is G-2;
$A_1$ is oxygen;
X is heteroaryl;
$R_1$ is hydrogen, alkyl or haloalkyl; and
Y is heteroaryl.

In another embodiment of the invention, a compound of formula (I) is provided wherein:
G is G-1;
$A_1$ is oxygen;
X is aryl;
$R_1$ is hydrogen, alkyl or haloalkyl; and
Y is pyrazolyl or triazolyl.

In another embodiment of the invention, a compound of formula (I) is provided wherein:
G is G-2;
$A_1$ is oxygen;
X is aryl;
$R_1$ is hydrogen, alkyl or haloalkyl; and
Y is pyrazolyl or triazolyl.

In still another embodiment of the invention, a compound of formula (I) is provided wherein:
G is G-1;
$A_1$ is oxygen;
X is aryl or heteroaryl;
$R_1$ is hydrogen, alkyl or haloalkyl; and Y is

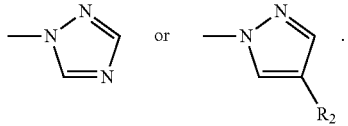

In yet another embodiment of the invention, a compound of formula (I) is provided wherein:
G is G-2;
$A_1$ is oxygen;
X is aryl or heteroaryl;
$R_1$ is hydrogen, alkyl or haloalkyl; and Y is

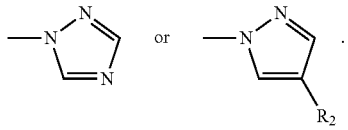

In another embodiment of the invention, a compound of formula (I) is provided wherein:
G is G-1;
$A_2$ is oxygen;
X is aryl; and
$R_1$ is hydrogen, alkyl or haloalkyl.

In another embodiment of the invention, a compound of formula (I) is provided wherein:
G is G-2;
$A_2$ is oxygen;
X is aryl; and
$R_1$ is hydrogen, alkyl or haloalkyl.

In another embodiment of the invention, a compound of formula (I) is provided wherein:
G is G-1;
$A_2$ is $NR_2$;
X is aryl; and
$R_1$ is hydrogen, alkyl or haloalkyl.

In another embodiment of the invention, a compound of formula (I) is provided wherein:
G is G-2;
$A_2$ is $NR_2$;
X is aryl; and
$R_1$ is hydrogen, alkyl or haloalkyl.

In yet another embodiment of the invention, a compound of formula (I) is provided wherein:
G is G-1;
$A_1$ is oxygen;
X is phenyl, which is unsubstituted or substituted by one or more halogen, $C_1$-$C_4$alkyl or $C_1$-$C_4$haloalkyl;
$R_1$ is hydrogen, alkyl or haloalkyl; and
Y is aryl.

In yet another embodiment of the invention, a compound of formula (I) is provided wherein:
G is G-2;
$A_1$ is oxygen;
X is phenyl, which is unsubstituted or substituted by one or more halogen, $C_1$-$C_4$alkyl or $C_1$-$C_4$haloalkyl;
$R_1$ is hydrogen, alkyl or haloalkyl; and
Y is aryl.

In yet another embodiment of the invention, a compound of formula (I) is provided wherein:
G is G-1;
$A_1$ is oxygen;
X is phenyl, which is unsubstituted or substituted by one or more halogen, $C_1$-$C_4$alkyl or $C_1$-$C_4$haloalkyl;
$R_1$ is hydrogen, alkyl or haloalkyl; and
Y is hydrogen, halogen, alkyl, haloalkyl, alkenyl, haloalkenyl, alkynyl or haloalkynyl.

In yet another embodiment of the invention, a compound of formula (I) is provided wherein:
G is G-2;
$A_1$ is oxygen;
X is phenyl, which is unsubstituted or substituted by one or more halogen, $C_1$-$C_4$alkyl or $C_1$-$C_4$haloalkyl;
$R_1$ is hydrogen, alkyl or haloalkyl; and
Y is hydrogen, halogen, alkyl, haloalkyl, alkenyl, haloalkenyl, alkynyl or haloalkynyl.

In various embodiments of the invention, Y is a five-membered ring heteraryl ring having one to four hetero atoms. In another embodiment, Y is a six-membered heteroaryl ring having one to four heteroatoms. In other embodiments, Y is a heterocyclic ring. In still other embodiments of the invention, Y is pyrrolyl, pyrrolinyl, pyrrolidinyl, pyrazolyl, pyrazolinyl, imidazolyl, imidazolinyl, triazolyl, tetrazolyl, thiophene, oxazolyl, oxazolinyl, isothiazolyl, thiadazolyl, pyrazolyl, furyl or tetrahydrofuryl. In still other embodiments, Y is pyridinyl, piperidinyl, morpholinyl, pyridazinyl, pyrimidinyl, pyrazinyl, triazinyl, tetrazinyl, indolyl, benzofuranyl, isoindolyl, benzothiophene, quinolyl, isoquinolyl, quinazolinyl, quinoxalinyl, or phthalazinyl.

In another embodiment, the invention provides compounds of formula (I) wherein:
G is G-1;
$R_1$ is halogen, —CN, alkenyl, haloalkenyl, alkynyl or haloalkynyl;
$A_1$ is oxygen;
X is phenyl, which is unsubstituted or substituted by one or more halogen, $C_1$-$C_4$alkyl or $C_1$-$C_4$haloalkyl; and
Y is Y-1, Y-2 or Y-3; and
$R_{10}$ and $R_{11}$ together form =O.

In another embodiment, the invention provides compounds of formula (I) wherein:
G is G-1;
$R_1$ is halogen, —CN, alkenyl, haloalkenyl, alkynyl or haloalkynyl;
$A_1$ is oxygen;
X is phenyl, which is unsubstituted or substituted by one or more halogen, $C_1$-$C_4$alkyl or $C_1$-$C_4$haloalkyl;
Y is Y-4, Y-5 or Y-6;
$R_{10}$ and $R_{11}$ together form =O; and
$R_{12}$ and $R_{13}$ together form =O.

In another embodiment, the invention provides compounds of formula (I) wherein:
G is G-1;
$R_1$ is halogen, —CN, alkenyl, haloalkenyl, alkynyl or haloalkynyl;
$A_1$ is oxygen;
X is phenyl, which is unsubstituted or substituted by one or more halogen, $C_1$-$C_4$alkyl or $C_1$-$C_4$haloalkyl; and
Y is Y-7, Y-8 or Y-9;
$R_{10}$ and $R_{11}$ together form =O; and
$R_{12}$ and $R_{13}$ together form =O.

In another embodiment, the invention provides compounds of formula (I) wherein:
G is G-1;
$R_1$ is halogen, —CN, alkenyl, haloalkenyl, alkynyl or haloalkynyl;
$A_1$ is oxygen;
X is phenyl, which is unsubstituted or substituted by one or more halogen, $C_1$-$C_4$alkyl or $C_1$-$C_4$haloalkyl; and
Y is Y-10, Y-11, Y-12 or Y-13.

In another embodiment, the invention provides compounds of formula (I) wherein:
G is G-2;
$R_1$ is halogen, —CN, alkenyl, haloalkenyl, alkynyl or haloalkynyl;
$A_1$ is oxygen;
X is phenyl, which is unsubstituted or substituted by one or more halogen, $C_1$-$C_4$alkyl or $C_1$-$C_4$haloalkyl;
Y is Y-1, Y-2 or Y-3; and
$R_{10}$ and $R_{11}$ together form =O.

In another embodiment, the invention provides compounds of formula (I) wherein:
G is G-2;
$R_1$ is halogen, —CN, alkenyl, haloalkenyl, alkynyl or haloalkynyl;
$A_1$ is oxygen;
X is phenyl, which is unsubstituted or substituted by one or more halogen, $C_1$-$C_4$alkyl or $C_1$-$C_4$haloalkyl;
Y is Y-4, Y-5 or Y-6;
$R_{10}$ and $R_{11}$ together form =O; and
$R_{12}$ and $R_{13}$ together form =O.

In another embodiment, the invention provides compounds of formula (I) wherein:
G is G-2;
$R_1$ is halogen, —CN, alkenyl, haloalkenyl, alkynyl or haloalkynyl;
$A_1$ is oxygen;
X is phenyl, which is unsubstituted or substituted by one or more halogen, $C_1$-$C_4$alkyl or $C_1$-$C_4$haloalkyl;
Y is Y-7, Y-8 or Y-9;
$R_{10}$ and $R_{11}$ together form =O; and
$R_{12}$ and $R_{13}$ together form =O.

In another embodiment, the invention provides compounds of formula (I) wherein:
G is G-2;
$R_1$ is halogen, —CN, alkenyl, haloalkenyl, alkynyl or haloalkynyl;
$A_1$ is oxygen;
X is phenyl, which is unsubstituted or substituted by one or more halogen, $C_1$-$C_4$alkyl or $C_1$-$C_4$haloalkyl; and
Y is Y-10, Y-11, Y-12 or Y-13.

In another embodiment, the invention provides compounds of formula (I) wherein:
G is G-1;
$R_1$ is halogen, —CN, alkenyl, haloalkenyl, alkynyl or haloalkynyl;
$A_1$ is oxygen;
X is phenyl, which is unsubstituted or substituted by one or more halogen, $C_1$-$C_4$alkyl or $C_1$-$C_4$haloalkyl;
Y is Y-4, Y-5 or Y-6;
$R_{10}$ and $R_{11}$ are independently hydrogen, $C_1$-$C_4$alkyl or $C_1$-$C_4$haloalkyl; and
$R_{12}$ and $R_{13}$ together form =O.

In another embodiment, the invention provides compounds of formula (I) wherein:
G is G-1;
$R_1$ is halogen, —CN, alkenyl, haloalkenyl, alkynyl or haloalkynyl;
$A_1$ is oxygen;
X is phenyl, which is unsubstituted or substituted by one or more halogen, $C_1$-$C_4$alkyl or $C_1$-$C_4$haloalkyl; and
Y is Y-7, Y-8 or Y-9;
$R_{10}$ and $R_{11}$ are independently hydrogen, $C_1$-$C_4$alkyl or $C_1$-$C_4$haloalkyl; and
$R_{12}$ and $R_{13}$ together form =O.

In another embodiment, the invention provides compounds of formula (I) wherein:
G is G-2;
$R_1$ is halogen, —CN, alkenyl, haloalkenyl, alkynyl or haloalkynyl;
$A_1$ is oxygen;
X is phenyl, which is unsubstituted or substituted by one or more halogen, $C_1$-$C_4$alkyl or $C_1$-$C_4$haloalkyl;
Y is Y-4, Y-5 or Y-6;
$R_{10}$ and $R_{11}$ are independently hydrogen, $C_1$-$C_4$alkyl or $C_1$-$C_4$haloalkyl; and
$R_{12}$ and $R_{13}$ together form =O.

In another embodiment, the invention provides compounds of formula (I) wherein:
G is G-2;
$R_1$ is halogen, —CN, alkenyl, haloalkenyl, alkynyl or haloalkynyl;
$A_1$ is oxygen;
X is phenyl, which is unsubstituted or substituted by one or more halogen, $C_1$-$C_4$alkyl or $C_1$-$C_4$haloalkyl;
Y is Y-7, Y-8 or Y-9;
$R_{10}$ and $R_{11}$ are independently hydrogen, $C_1$-$C_4$alkyl or $C_1$-$C_4$haloalkyl; and
$R_{12}$ and $R_{13}$ together form =O.

In another embodiment, the invention provides compounds of formula (I) wherein:
G is G-1;
$R_1$ is halogen, —CN, alkenyl, haloalkenyl, alkynyl or haloalkynyl;
$A_1$ is oxygen;
X is phenyl, which is unsubstituted or substituted by one or more halogen, $C_1$-$C_4$alkyl or $C_1$-$C_4$haloalkyl;
Y is Y-4, Y-5 or Y-6;
$R_{10}$ and $R_{11}$ together form =O; and
$R_{12}$ and $R_{13}$ are independently hydrogen, $C_1$-$C_4$alkyl or $C_1$-$C_4$haloalkyl.

In another embodiment, the invention provides compounds of formula (I) wherein:
G is G-1;
$R_1$ is halogen, —CN, alkenyl, haloalkenyl, alkynyl or haloalkynyl;
$A_1$ is oxygen;
X is phenyl, which is unsubstituted or substituted by one or more halogen, $C_1$-$C_4$alkyl or $C_1$-$C_4$haloalkyl; and
Y is Y-7, Y-8 or Y-9;
$R_{10}$ and $R_{11}$ together form =O; and
$R_{12}$ and $R_{13}$ are independently hydrogen, $C_1$-$C_4$alkyl or $C_1$-$C_4$haloalkyl.

In another embodiment, the invention provides compounds of formula (I) wherein:
G is G-2;
$R_1$ is halogen, —CN, alkenyl, haloalkenyl, alkynyl or haloalkynyl;
$A_1$ is oxygen;
X is phenyl, which is unsubstituted or substituted by one or more halogen, $C_1$-$C_4$alkyl or $C_1$-$C_4$haloalkyl;
Y is Y-4, Y-5 or Y-6;
$R_{10}$ and $R_{11}$ together form =O; and
$R_{12}$ and $R_{13}$ are independently hydrogen, $C_1$-$C_4$alkyl or $C_1$-$C_4$haloalkyl.

In another embodiment, the invention provides compounds of formula (I) wherein:
G is G-2;
$R_1$ is halogen, —CN, alkenyl, haloalkenyl, alkynyl or haloalkynyl;
$A_1$ is oxygen;
X is phenyl, which is unsubstituted or substituted by one or more halogen, $C_1$-$C_4$alkyl or $C_1$-$C_4$haloalkyl;
Y is Y-7, Y-8 or Y-9;
$R_{10}$ and $R_{11}$ together form =O; and
$R_{12}$ and $R_{13}$ are independently hydrogen, $C_1$-$C_4$alkyl or $C_1$-$C_4$haloalkyl.

In another embodiment of the invention, a compound of formula (I) is provided wherein:
G is G-1;
$B_1$, $B_2$, $B_3$, $B_4$ and $B_5$ are each C—$R_9$;
$R_1$ is $C_1$-$C_4$alkyl or $C_1$-$C_4$haloalkyl;
X is phenyl, which may be unsubstituted or substituted by one or more halogen, $C_1$-$C_4$alkyl or $C_1$-$C_4$haloalkyl;
$A_1$ is oxygen;
$A_2$ is $CR_7R_8$;
Y is Y-1, Y-4, Y-5 or Y-6;
$R_2$ and $R_4$ are independently hydrogen, $C_1$-$C_4$alkyl, $C_1$-$C_4$haloalkyl, $C_1$-$C_4$akoxy-$C_1$-$C_4$alkyl or $C_1$-$C_4$alkylthio-$C_1$-$C_4$alkyl; and
$R_3$ and $R_9$ are independently hydrogen, $C_1$-$C_4$alkyl or $C_1$-$C_4$haloalkyl.

In another embodiment of the invention, a compound of formula (I) is provided wherein:
G is G-2;
$B_1$, $B_2$, $B_4$ and $B_5$ are each C—$R_9$;
$B_3$ is N;
$R_1$ is $C_1$-$C_4$alkyl or $C_1$-$C_4$haloalkyl;
X is phenyl, which may be unsubstituted or substituted by one or more halogen, $C_1$-$C_4$alkyl or $C_1$-$C_4$haloalkyl;
$A_1$ is oxygen;
$A_2$ is $CR_7R_8$;
Y is Y-1, Y-4, Y-5 or Y-6;
$R_2$ and $R_4$ are independently hydrogen, $C_1$-$C_4$alkyl, $C_1$-$C_4$haloalkyl, $C_1$-$C_4$akoxy-$C_1$-$C_4$alkyl or $C_1$-$C_4$alkylthio-$C_1$-$C_4$alkyl; and
$R_3$ and $R_9$ are independently hydrogen, $C_1$-$C_4$alkyl or $C_1$-$C_4$haloalkyl.

In another embodiment of the invention, a compound of formula (I) is provided wherein:
G is G-2;
$B_1$ is N;
$B_2$, $B_3$, $B_4$ and $B_5$ are each C—$R_9$;
$R_1$ is $C_1$-$C_4$alkyl or $C_1$-$C_4$haloalkyl;
X is phenyl, which may be unsubstituted or substituted by one or more halogen, $C_1$-$C_4$alkyl or $C_1$-$C_4$haloalkyl;
$A_1$ is oxygen;
$A_2$ is $CR_7R_8$;
Y is Y-1, Y-4, Y-5 or Y-6;
$R_2$ and $R_4$ are independently hydrogen, $C_1$-$C_4$alkyl, $C_1$-$C_4$haloalkyl, $C_1$-$C_4$akoxy-$C_1$-$C_4$alkyl or $C_1$-$C_4$alkylthio-$C_1$-$C_4$alkyl; and
$R_3$ and $R_9$ are independently hydrogen, $C_1$-$C_4$alkyl or $C_1$-$C_4$haloalkyl.

In another embodiment of the invention, a compound of formula (I) is provided wherein:
G is G-1;
$B_1$, $B_2$, $B_3$, $B_4$ and $B_5$ are each C—$R_9$;
$R_1$ is $C_1$-$C_4$haloalkyl;
X is phenyl, which may be unsubstituted or substituted by one or more halogen, $C_1$-$C_4$alkyl or $C_1$-$C_4$haloalkyl;
$A_1$ is oxygen;
$A_2$ is $CH_2$;
Y is Y-4 or Y-6;
$R_{10}$ and $R_{11}$ together form =O;
$R_{12}$ and $R_{13}$ together form =O;
$R_2$ is hydrogen, $C_1$-$C_4$alkyl, $C_1$-$C_4$haloalkyl, $C_1$-$C_4$akoxy-$C_1$-$C_4$alkyl or $C_1$-$C_4$alkylthio-$C_1$-$C_4$alkyl;
$R_3$ and $R_9$ are independently hydrogen, $C_1$-$C_4$alkyl or $C_1$-$C_4$haloalkyl;
$R_7$ and $R_8$ are independently hydrogen or $C_{1-4}$alkyl; and
n is 1, 2 or 3.

In another embodiment of the invention, a compound of formula (I) is provided wherein:
G is G-2;
$B_1$, $B_2$, $B_3$, $B_4$ and $B_5$ are each C—$R_9$;
$R_1$ is $C_1$-$C_4$haloalkyl;

X is phenyl, which may be unsubstituted or substituted by one or more halogen, $C_1$-$C_4$alkyl or $C_1$-$C_4$haloalkyl;
$A_1$ is oxygen;
$A_2$ is $CH_2$;
Y is Y-4 or Y-6;
$R_{10}$ and $R_{11}$ together form =O;
$R_{12}$ and $R_{13}$ together form =O;
$R_2$ is hydrogen, $C_1$-$C_4$alkyl, $C_1$-$C_4$haloalkyl, $C_1$-$C_4$akoxy-$C_1$-$C_4$alkyl or $C_1$-$C_4$alkylthio-$C_1$-$C_4$alkyl;
$R_3$ and $R_9$ are independently hydrogen, $C_1$-$C_4$alkyl or $C_1$-$C_4$haloalkyl;
$R_7$ and $R_8$ are independently hydrogen or $C_{1-4}$alkyl; and
n is 1, 2 or 3.

In another embodiment of the invention, a compound of formula (I) is provided wherein:
G is G-1;
$B_3$ is N;
$B_1$, $B_2$, $B_4$ and $B_5$ are each C—$R_9$;
$R_1$ is $C_1$-$C_4$haloalkyl;
X is phenyl, which may be unsubstituted or substituted by one or more halogen, $C_1$-$C_4$alkyl or $C_1$-$C_4$haloalkyl;
$A_1$ is oxygen;
$A_2$ is $CH_2$;
Y is Y-4 or Y-6;
$R_{10}$ and $R_{11}$ together form =O;
$R_{12}$ and $R_{13}$ together form =O;
$R_2$ is hydrogen, $C_1$-$C_4$alkyl, $C_1$-$C_4$haloalkyl, $C_1$-$C_4$akoxy-$C_1$-$C_4$alkyl or $C_1$-$C_4$alkylthio-$C_1$-$C_4$alkyl;
$R_3$ and $R_9$ are independently hydrogen, $C_1$-$C_4$alkyl or $C_1$-$C_4$haloalkyl;
$R_7$ and $R_8$ are independently hydrogen or $C_{1-4}$alkyl; and
n is 1, 2 or 3.

In another embodiment of the invention, a compound of formula (I) is provided wherein:
G is G-2;
$B_1$ is N;
$B_2$, $B_3$, $B_4$ and $B_5$ are each C—$R_9$;
$R_1$ is $C_1$-$C_4$haloalkyl;
X is phenyl, which may be unsubstituted or substituted by one or more halogen, $C_1$-$C_4$alkyl or $C_1$-$C_4$haloalkyl;
$A_1$ is oxygen;
$A_2$ is $CH_2$;
Y is Y-4 or Y-6;
$R_{10}$ and $R_{11}$ together form =O;
$R_{12}$ and $R_{13}$ together form =O;
$R_2$ is hydrogen, $C_1$-$C_4$alkyl, $C_1$-$C_4$haloalkyl, $C_1$-$C_4$akoxy-$C_1$-$C_4$alkyl or $C_1$-$C_4$alkylthio-$C_1$-$C_4$alkyl;
$R_3$ and $R_9$ are independently hydrogen, $C_1$-$C_4$alkyl or $C_1$-$C_4$haloalkyl;
$R_7$ and $R_8$ are independently hydrogen or $C_{1-4}$alkyl; and
n is 1, 2 or 3.

In another embodiment of the invention, a compound of formula (I) is provided wherein:
G is G-1;
$B_1$, $B_2$, $B_3$, $B_4$ and $B_5$ are each C—$R_9$;
$R_1$ is $CF_3$;
X is phenyl, which may be unsubstituted or substituted by one or more chloro, fluoro, methyl or trifluoromethyl;
$A_1$ is oxygen;
$A_2$ is $CH_2$;
Y is Y-4 or Y-6;
$R_{10}$ and $R_{11}$ together form =O;
$R_{12}$ and $R_{13}$ together form =O;
$R_2$ is hydrogen, $C_1$-$C_4$alkyl, $C_1$-$C_4$haloalkyl, $C_1$-$C_4$akoxy-$C_1$-$C_4$alkyl or $C_1$-$C_4$alkylthio-$C_1$-$C_4$alkyl;
$R_3$ and $R_9$ are independently hydrogen, $C_1$-$C_4$alkyl or $C_1$-$C_4$haloalkyl;
$R_7$ and $R_8$ are independently hydrogen or $C_{1-4}$alkyl; and
n is 1, 2 or 3.

In another embodiment of the invention, a compound of formula (I) is provided wherein:
G is G-2;
$B_1$, $B_2$, $B_3$, $B_4$ and $B_5$ are each C—$R_9$;
$R_1$ is $CF_3$;
X is phenyl, which may be unsubstituted or substituted by one or more chloro, fluoro, methyl or trifluoromethyl;
$A_1$ is oxygen;
$A_2$ is $CH_2$;
Y is Y-4 or Y-6;
$R_{10}$ and $R_{11}$ together form =O;
$R_{12}$ and $R_{13}$ together form =O;
$R_2$ is hydrogen, $C_1$-$C_4$alkyl, $C_1$-$C_4$haloalkyl, $C_1$-$C_4$akoxy-$C_1$-$C_4$alkyl or $C_1$-$C_4$alkylthio-$C_1$-$C_4$alkyl;
$R_3$ and $R_9$ are independently hydrogen, $C_1$-$C_4$alkyl or $C_1$-$C_4$haloalkyl;
$R_7$ and $R_8$ are independently hydrogen or $C_{1-4}$alkyl; and
n is 1, 2 or 3.

In another embodiment of the invention, a compound of formula (I) is provided wherein:
G is G-1;
$B_3$ is N;
$B_1$, $B_2$, $B_4$ and $B_5$ are each C—$R_9$;
$R_1$ is $CF_3$;
X is phenyl, which may be unsubstituted or substituted by one or more chloro, fluoro, methyl or trifluoromethyl;
$A_1$ is oxygen;
$A_2$ is $CH_2$;
Y is Y-4 or Y-6;
$R_{10}$ and $R_{11}$ together form =O;
$R_{12}$ and $R_{13}$ together form =O;
$R_2$ is hydrogen, $C_1$-$C_4$alkyl, $C_1$-$C_4$haloalkyl, $C_1$-$C_4$akoxy-$C_1$-$C_4$alkyl or $C_1$-$C_4$alkylthio-$C_1$-$C_4$alkyl;
$R_3$ and $R_9$ are independently hydrogen, $C_1$-$C_4$alkyl or $C_1$-$C_4$haloalkyl;
$R_7$ and $R_8$ are independently hydrogen or $C_{1-4}$alkyl; and
n is 1, 2 or 3.

In another embodiment of the invention, a compound of formula (I) is provided wherein:
G is G-2;
$B_1$ is N;
$B_2$, $B_3$, $B_4$ and $B_5$ are each C—$R_9$;
$R_1$ is $CF_3$;
X is phenyl, which may be unsubstituted or substituted by one or more chloro, fluoro, methyl or trifluoromethyl;
$A_1$ is oxygen;
$A_2$ is $CH_2$;
Y is Y-4 or Y-6;
$R_{10}$ and $R_{11}$ together form =O;
$R_{12}$ and $R_{13}$ together form =O;
$R_2$ is hydrogen, $C_1$-$C_4$alkyl, $C_1$-$C_4$haloalkyl, $C_1$-$C_4$akoxy-$C_1$-$C_4$alkyl or $C_1$-$C_4$alkylthio-$C_1$-$C_4$alkyl;
$R_3$ and $R_9$ are independently hydrogen, $C_1$-$C_4$alkyl or $C_1$-$C_4$haloalkyl;
$R_7$ and $R_8$ are independently hydrogen or $C_{1-4}$alkyl; and
n is 1, 2 or 3.

In another embodiment of the invention, a compound of formula (I) is provided wherein:
G is G-1;
$B_1$, $B_2$, $B_3$, $B_4$ and $B_5$ are each C—H;
$R_1$ is $CF_3$;
X is phenyl, which may be unsubstituted or substituted by one or more chloro, fluoro, methyl or trifluoromethyl;
$A_1$ is oxygen;
$A_2$ is $CH_2$;

Y is Y-4 or Y-6;
$R_{10}$ and $R_{11}$ together form =O;
$R_{12}$ and $R_{13}$ together form =O;
$R_2$ is hydrogen or methyl;
$R_3$ is hydrogen, $C_1$-$C_4$alkyl or $C_1$-$C_4$haloalkyl;
$R_7$ and $R_8$ are hydrogen; and
n is 1, 2 or 3.

In another embodiment of the invention, a compound of formula (I) is provided wherein:
G is G-2;
$B_1$, $B_2$, $B_3$, $B_4$ and $B_5$ are each C—H;
$R_1$ is $CF_3$;
X is phenyl, which may be unsubstituted or substituted by one or more chloro, fluoro, methyl or trifluoromethyl;
$A_1$ is oxygen;
$A_2$ is $CH_2$;
Y is Y-4 or Y-6;
$R_{10}$ and $R_{11}$ together form =O;
$R_{12}$ and $R_{13}$ together form =O;
$R_2$ is hydrogen or methyl;
$R_3$ is hydrogen, $C_1$-$C_4$alkyl or $C_1$-$C_4$haloalkyl;
$R_7$ and $R_8$ are hydrogen; and
n is 1, 2 or 3.

In another embodiment of the invention, a compound of formula (I) is provided wherein:
G is G-1;
$B_3$ is N;
$B_1$, $B_2$, $B_4$ and $B_5$ are each C—H;
$R_1$ is $CF_3$;
X is phenyl, which may be unsubstituted or substituted by one or more chloro, fluoro, methyl or trifluoromethyl;
$A_1$ is oxygen;
$A_2$ is $CH_2$;
Y is Y-4 or Y-6;
$R_{10}$ and $R_{11}$ together form =O;
$R_{12}$ and $R_{13}$ together form =O;
$R_2$ is hydrogen or methyl;
$R_3$ is hydrogen, $C_1$-$C_4$alkyl or $C_1$-$C_4$haloalkyl;
$R_7$ and $R_8$ are hydrogen; and
n is 1, 2 or 3.

In another embodiment of the invention, a compound of formula (I) is provided wherein:
G is G-2;
$B_1$ is N;
$B_2$, $B_3$, $B_4$ and $B_5$ are each C—H;
$R_1$ is $CF_3$;
X is phenyl, which may be unsubstituted or substituted by one or more chloro, fluoro, methyl or trifluoromethyl;
$A_1$ is oxygen;
$A_2$ is $CH_2$;
Y is Y-4 or Y-6;
$R_{10}$ and $R_{11}$ together form =O;
$R_{12}$ and $R_{13}$ together form =O;
$R_2$ is hydrogen or methyl;
$R_3$ is hydrogen, $C_1$-$C_4$alkyl or $C_1$-$C_4$haloalkyl;
$R_7$ and $R_8$ are hydrogen; and
n is 1, 2 or 3.

Stereoisomers and Polymorphic Forms

It will be appreciated by those of skill in the art that the compounds of the invention may exist and be isolated as optically active and racemic forms. Compounds having one or more chiral centers, including that at a sulfur atom, may be present as single enantiomers or diastereomers or as mixtures of enantiomers and/or diastereomers. For example, it is well known in the art that sulfoxide compounds may be optically active and may exist as single enantiomers or racemic mixtures. In addition, compounds of the invention may include one or more chiral centers, which results in a theoretical number of optically active isomers. Where compounds of the invention include n chiral centers, the compounds may comprise up to $2^n$ optical isomers. The present invention encompasses the specific enantiomers or diastereomers of each compound as well as mixtures of different enantiomers and/or diastereomers of the compounds of the invention that possess the useful properties described herein. The optically active forms can be prepared by, for example, resolution of the racemic forms by selective crystallization techniques, by synthesis from optically active precursors, by chiral synthesis, by chromatographic separation using a chiral stationary phase or by enzymatic resolution.

The compounds of present invention may also be present in different solid forms such as different crystalline forms or in the form of an amorphous solid. The present invention encompasses different crystalline forms as well as amorphous forms of the inventive compounds.

In addition, the compounds of the invention may exist as hydrates or solvates, in which a certain stoichiometric amount of water or a solvent is associated with the molecule in the crystalline form. The hydrates and solvates of the compounds of formula (I) or (II) are also the subject of the invention.

Salts

In addition to the neutral compounds of formula (I), salt forms of the compounds are also active against animal pests. The terms "veterinarily acceptable salt" and "agriculturally acceptable salt" are used throughout the specification to describe any salts of the compounds that are acceptable for administration for veterinary and agricultural applications, and which provides the active compound upon administration.

In cases where compounds are sufficiently basic or acidic to form stable non-toxic acid or base salts, the compounds may be in the form of a veterinarily or agriculturally acceptable salt. Veterinarily or agriculturally acceptable salts include those derived from veterinarily or agriculturally acceptable inorganic or organic bases and acids. Suitable salts include those comprising alkali metals such as lithium, sodium or potassium, alkaline earth metals such as calcium, magnesium and barium. Salts comprising transition metals including, but not limited to, manganese, copper, zinc and iron are also suitable. In addition, salts comprising ammonium cations ($NH_4^+$) as well as substituted ammonium cations, in which one or more of the hydrogen atoms are replaced by alkyl or aryl groups are encompassed by the invention.

Salts derived from inorganic acids including, but not limited to, hydrohalide acids (HCl, HBr, HF, HI), sulfuric acid, nitric acid, phosphoric acid, and the like are particularly suitable. Suitable inorganic salts also include, but not limited to, bicarbonate, and carbonate salts. In some embodiments, examples of veterinarily and agriculturally acceptable salts are organic acid addition salts formed with organic acids including, but not limited to, maleate, dimaleate, fumarate, tosylate, methanesulfonate, acetate, citrate, malonate, tartarate, succinate, benzoate, ascorbate, α-ketoglutarate, and α-glycerophosphate. Of course, other acceptable organic acids may be used.

Alkali metal (for example, sodium, potassium or lithium) or alkaline earth metal (for example calcium) salts of the compounds can also be made by reacting a sufficiently acidic residue on the compounds with a hydroxide of the alkali metal or alkaline earth metal.

Veterinarily and agriculturally acceptable salts may be obtained using standard procedures well known in the art, for example by reacting a sufficiently basic compound such as an amine with a suitably acid functional group present in the compound, or by reacting a suitable acid with a suitably basic functional group on the compound of the invention.

Definitions

For the purposes of this application, unless otherwise stated in the specification, the following terms have the terminology cited below:

(1) Alkyl refers to both straight, branched carbon chains and cyclic hydrocarbon groups. In one embodiment of alkyl, the number of carbons atoms is 1-20, in other embodiments of alkyl, the number of carbon atoms is 1-12, 1-10 or 1-8 carbon atoms. In yet another embodiment of alkyl, the number of carbon atoms is 1-6 or 1-4 carbon atoms. Other ranges of carbon numbers are also contemplated depending on the location of the alkyl moiety on the molecule;

Examples of $C_1$-$C_{10}$ alkyl include, but are not limited to, methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, heptyl, octyl, 2-ethylhexyl, nonyl and decyl and their isomers. $C_1$-$C_4$-alkyl means for example methyl, ethyl, propyl, 1-methylethyl, butyl, 1-methylpropyl, 2-methylpropyl or 1,1-dimethylethyl.

Cyclic alkyl groups, which are encompassed by the term "alkyl", may be referred to as "cycloalkyl" and include those with 3 to 10 carbon atoms having single or multiple fused rings. Non-limiting examples of cycloalkyl groups include adamantyl, cyclopropyl, cyclobutyl, cyclopentyl, cyclohexyl, cycloheptyl, cyclooctyl and the like.

The alkyl and cycloalkyl groups described herein can be unsubstituted or substituted with one or more moieties selected from the group consisting of alkyl, halo, haloalkyl, hydroxyl, carboxyl, acyl, acyloxy, amino, alkyl- or dialkylamino, amido, arylamino, alkoxy, aryloxy, nitro, cyano, azido, thiol, imino, sulfonic acid, sulfate, sulfonyl, sulfanyl, sulfinyl, sulfamonyl, ester, phosphonyl, phosphinyl, phosphoryl, phosphine, thioester, thioether, acid halide, anhydride, oxime, hydrozine, carbamate, phosphonic acid, phosphate, phosphonate, or any other viable functional group that does not inhibit the biological activity of the compounds of the invention, either unprotected, or protected as necessary, as known to those skilled in the art, for example, as taught in Greene, et al., *Protective Groups in Organic Synthesis*, John Wiley and Sons, Fourth Edition, 2007, hereby incorporated by reference.

(2) Alkenyl refers to both straight and branched carbon chains which have at least one carbon-carbon double bond. In one embodiment of alkenyl, the number of double bonds is 1-3, in another embodiment of alkenyl, the number of double bonds is one. In one embodiment of alkenyl, the number of carbons atoms is 2-20, in other embodiments of alkenyl, the number of carbon atoms is 2-12, 2-10, 2-8 or 2-6. In yet another embodiment of alkenyl, the number of carbon atoms is 2-4. Other ranges of carbon-carbon double bonds and carbon numbers are also contemplated depending on the location of the alkenyl moiety on the molecule;

"$C_2$-$C_{10}$-alkenyl" groups may include more than one double bond in the chain. Examples include, but are not limited to, ethenyl, 1-propenyl, 2-propenyl, 1-methyl-ethenyl, 1-butenyl, 2-butenyl, 3-butenyl, 1-methyl-1-propenyl, 2-methyl-1-propenyl, 1-methyl-2-propenyl, 2-methyl-2-propenyl; 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, i,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl.

(3) Alkynyl refers to both straight and branched carbon chains which have at least one carbon-carbon triple bond. In one embodiment of alkynyl, the number of triple bonds is 1-3; in another embodiment of alkynyl, the number of triple bonds is one. In one embodiment of alkynyl, the number of carbons atoms is 2-20, in other embodiments of alkynyl, the number of carbon atoms is 2-12, 2-10, 2-8 or 2-6. In yet another embodiment of alkynyl, the number of carbon atoms is 2-4. Other ranges of carbon-carbon double bonds and carbon numbers are also contemplated depending on the location of the alkenyl moiety on the molecule;

For example, the term "$C_2$-$C_{10}$-alkynyl" as used herein refers to a straight-chain or branched unsaturated hydrocarbon group having 2 to 10 carbon atoms and containing at least one triple bond, such as ethynyl, prop-1-yn-1-yl, prop-2-yn-1-yl, n-but-1-yn-1-yl, n-but-1-yn-3-yl, n-but-1-yn-4-yl, n-but-2-yn-1-yl, n-pent-1-yn-1-yl, n-pent- 1-yn-3-yl, n-pent-1-yn-4-yl, n-pent-1-yn-5-yl, n-pent-2-yn-1-yl, n-pent-2-yn-4-yl, n-pent-2-yn-5-yl, 3-methylbut-1-yn-3-yl, 3-methylbut-1-yn-4-yl, n-hex-1-yn-1-yl, n-hex-1-yn-3-yl, n-hex-1-yn-4-yl, n-hex-1-yn-5-yl, n-hex-1-yn-6-yl, n-hex-2-yn-1-yl, n-hex-2-yn-4-yl, n-hex-2-yn-5-yl, n-hex-2-yn-6-yl, n-hex-3-yn-1-yl, n-hex-3-yn-2-yl, 3-methylpent-1-yn- 1-yl, 3-methylpent-1-yn-3-yl, 3-methylpent-1-yn-4-yl, 3-methylpent-1-yn-5-yl, 4-methylpent-1-yn-1-yl, 4-methylpent-2-yn-4-yl or 4-methylpent-2-yn-5-yl and the like.

(4) Aryl refers to a $C_6$-$C_{14}$ aromatic carbocyclic ring structure having a single ring or multiple fused rings. In some embodiments, the aryl ring may be fused to a non-aromatic ring, as long as the point of attachment to the core structure is through the aromatic ring. Aryl groups include, but are not limited to, phenyl, biphenyl, and naphthyl. In some embodiments aryl includes tetrahydronapthyl and indanyl. Aryl groups may be unsubstituted or substituted by one or more moieties selected from halogen, cyano, nitro, hydroxy, mercapto, amino, alkyl, alkenyl, alkynyl, cycloalkyl, cycloalkenyl, haloalkyl, haloalkenyl, haloalkynyl, halocycloalkyl, halocycloalkenyl, alkoxy, alkenyloxy, alkynyloxy, haloalkoxy, haloalkenyl oxy, haloalkynyloxy, cycloalkoxy, cycloalkenyloxy, halocycloalkoxy, halocycloalkenyloxy, alkylthio, haloalkylthio, arylthio, cycloalkylthio, halocycloalkylthio, alkyl sulfinyl, alkenyl sulfinyl, alkynylsulfinyl, haloalkyl sulfinyl, haloalkenyl sulfinyl, haloalkynyl sulfinyl, alkyl sulfonyl, alkenyl sulfonyl, alkynyl sulfonyl, haloalkyl-sulfonyl, haloalkenyl sulfonyl, haloalkynyl sulfonyl, alkylcarbonyl, haloalkylcarbonyl, alkylamino, alkenylamino, alkynylamino, di(alkyl)amino, di(alkenyl)-amino, di(alkynyl)amino, or $SF_5$. In one embodiment of aryl, the moiety is phenyl, naphthyl, tetrahydronapthyl, phenylcyclopropyl and indanyl; in another embodiment of aryl, the moiety is phenyl.

(5) Alkoxy refers to —O-alkyl, wherein alkyl is as defined in (1);

(6) Alkoxycarbonyl refers to —C(=O)—O-alkyl, wherein alkoxy is as defined in (5);

(7) Cyclo as a prefix (e.g. cycloalkyl, cycloalkenyl, cycloalkynyl) refers to a saturated or unsaturated cyclic ring structure having from three to eight carbon atoms in the ring the scope of which is intended to be separate and distinct from the definition of aryl above. In one embodiment of cyclo, the range of ring sizes is 4-7 carbon atoms; in another embodiment of cyclo the range of ring sizes is 3-4. Other ranges of carbon numbers are also contemplated depending on the location of the cyclo- moiety on the molecule;

(8) Halogen means the atoms fluorine, chlorine, bromine and iodine. The designation of "halo" (e.g. as illustrated in the term haloalkyl) refers to all degrees of substitutions from a single substitution to a perhalo substitution (e.g. as illustrated with methyl as chloromethyl (—$CH_2Cl$), dichloromethyl (—$CHCl_2$), trichloromethyl (—$CCl_3$));

(9) Heterocycle, heterocyclic or heterocyclo refers to fully saturated or unsaturated cyclic groups, for example, 4 to 7 membered monocyclic, 7 to 11 membered bicyclic, or 10 to 15 membered tricyclic ring systems, which have at least one heteroatom in at least one carbon atom-containing ring. Each ring of the heterocyclic group containing a heteroatom may have 1, 2, 3 or 4 heteroatoms selected from nitrogen atoms, oxygen atoms and/or sulfur atoms, where the nitrogen and sulfur heteroatoms may optionally be oxidized and the nitrogen heteroatoms may optionally be quaternized. The heterocyclic group may be attached at any heteroatom or carbon atom of the ring or ring system.

(10) Heteroaryl refers to a monovalent aromatic group of from 1 to 15 carbon atoms, preferably from 1 to 10 carbon atoms, having one or more oxygen, nitrogen, and sulfur heteroatoms within the ring, preferably 1 to 4 heteroatoms, or 1 to 3 heteroatoms. The nitrogen and sulfur heteroatoms may optionally be oxidized. Such heteroaryl groups can have a single ring (e.g., pyridyl or furyl) or multiple fused rings provided that the point of attachment is through a heteroaryl ring atom. Preferred heteroaryls include pyridyl, piridazinyl, pyrimidinyl, triazinyl, pyrrolyl, quinolinyl, isoquinolinyl, quinazolinyl, quinoxalinnyl, furanyl, thienyl, furyl, imidazolyl, oxazolyl, isoxazolyl, isothiazolyl, pyrazolyl, benzofuranyl, and benzothienyl. Heteroaryl rings may be unsubstituted or substituted by one or more moieties as described for aryl above.

Exemplary monocyclic heterocyclic or heteroaryl groups also include, but are not limited to, pyrrolidinyl, oxetanyl, pyrazolinyl, imidazolinyl, imidazolidinyl, oxazolidinyl, isoxazolinyl, thiazolyl, thiadiazolyl, thiazolidinyl, isothiazolidinyl, tetrahydrofuryl, thienyl, oxadiazolyl, piperidinyl, piperazinyl, 2-oxopiperazinyl, 2-oxopiperidinyl, 2-oxopyrrolodinyl, 2-oxoazepinyl, azepinyl, 4-piperidonyl, pyridinyl, pyrazinyl, pyridazinyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl, triazolyl, and the like.

Exemplary bicyclic heterocyclic groups include, but are not limited to, indolyl, benzothiazolyl, benzoxazolyl, benzodioxolyl, benzothienyl, quinuclidinyl, tetra-hydroisoquinolinyl, benzimidazolyl, benzopyranyl, indolizinyl, benzofuryl, chromonyl, coumarinyl, benzopyranyl, cinnolinyl, quinoxalinyl, indazolyl, pyrrolopyridyl, furopyridinyl (such as furo[2,3-c]pyridinyl, furo[3,2-b]pyridinyl] or furo[2,3-b]pyridinyl), dihydroisoindolyl, dihydroquinazolinyl (such as 3,4-dihydro-4-oxo-quinazolinyl), tetrahydroquinolinyl and the like.

Exemplary tricyclic heterocyclic groups include, but are not limited to, carbazolyl, benzidolyl, phenanthrolinyl, acridinyl, phenanthridinyl, xanthenyl and the like.

Unless otherwise specifically noted or apparent by context, "active agent" or "active ingredient" or "therapeutic agent" as used in this specification, means a dihydroazole compound of the invention.

The term "locus" is intended to mean a habitat, breeding ground, area, material or environment in which a parasite is growing or may grow, including in or on an animal.

Synthesis of Compounds

The dihydroazole compounds of formula (I) may be prepared by processes described herein or by adaptation of these processes or process known in the art to prepare compounds with different substitution patterns.

For example, Scheme 1 below depicts the preparation of compounds of formula (I) where G is G-2, $B_1$ and $B_2$ are C—H, $B_3$, is C—H or C—$R^9$, $A_1$ is oxygen, $A_2$ is $CH_2$, $R_1$ is $CF_3$, X is an optionally substituted phenyl group, and Y may be Y-1, Y-2, Y-4, Y-5, Y-6, Y-7, Y-8 or Y-9, where $R_{10}$ and $R_{11}$ together form C=O, and $R_2$, $R_3$, $R_4$, $R_7$, $R_8$, $R_{12}$, $R_{13}$ and n are as defined above. It will be apparent to those of skill in the art that certain functional groups present in compounds used in the synthesis may be protected, if necessary, by a suitable protecting group such as an alkyl ester, as described in "*Protective Groups in Organic Synthesis* (Fourth Edition)", eds. Peter G. M. Wuts and Theodora W. Greene, Wiley-Interscience Publishers, (2007). Furthermore, it will be apparent to those of skill in the art that the reactions described may be run in suitable solvents depending on the conditions of the reaction. Reaction times and temperatures may be optimized to produce the desired product in good yield and purity. Furthermore, the final products and intermediates may be isolated and purified, if appropriate, or carried forward to the next step without isolation and/or purification when possible. Purification of intermediates and products may be conducted by suitable methods including chromatographic methods such as flash column chromatography, HPLC, and the like. Purification of intermediates and products may also be achieved by crystallization of the intermediates and products from a suitable solvent or solvent mixture, or a combination of crystallization and chromatography.

Scheme 1
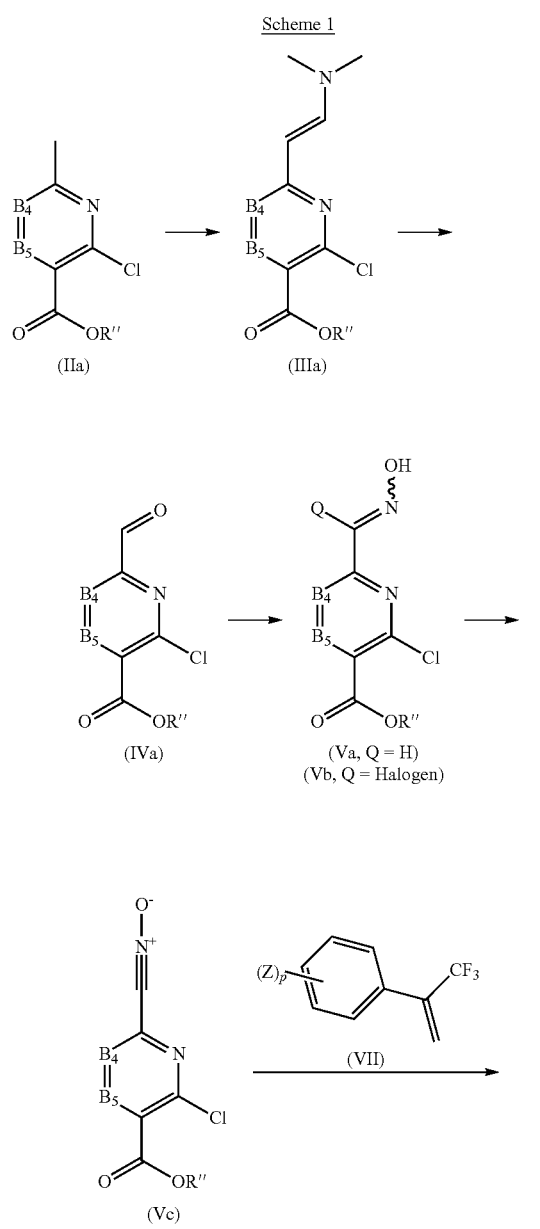
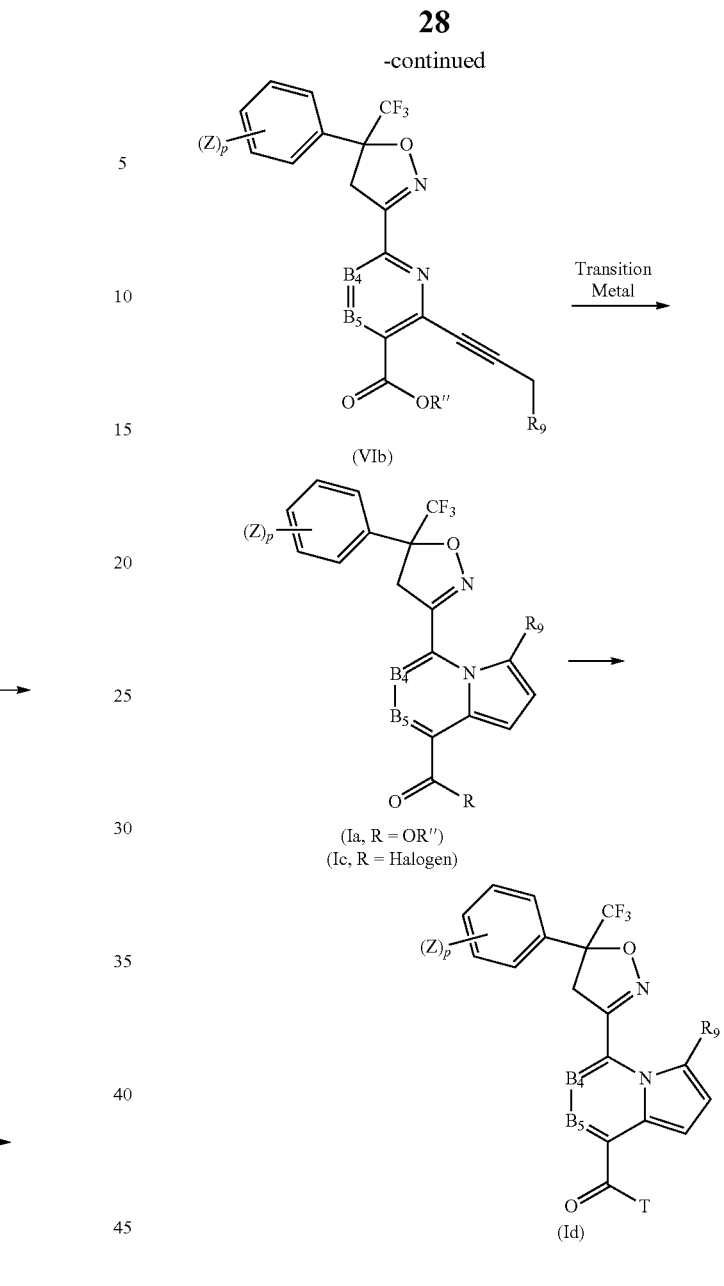
Where R″ is H, alkyl or PG:
Where T is NR$_2$R$_3$,
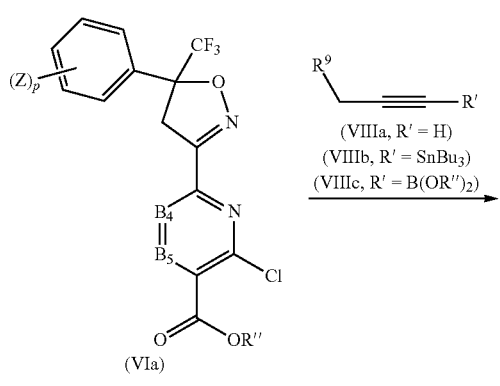
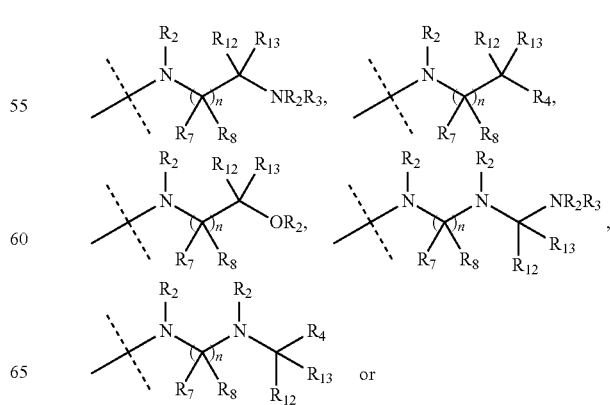

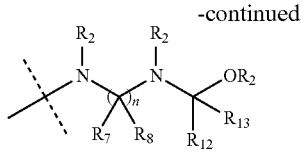

where $R_2$, $R_3$, $R_4$, $R_7$, $R_8$, $R_{12}$, $R_{13}$ and n are as defined above.

Reaction of a 2-halo-6-methyl nicotinic acid derivative of formula (IIa) where R" is H or a hydroxy protecting group (PG) including, but not limited to, 2-chloro-6-methyl nicotinic acid compound, with a dialkylformamide dialkylacetal, including dimethylformamide dimethyl acetal, produces a 2-halo-6-(2-dialkylaminovinyl)-niconitic acid derivative of formula (IIIa). Other suitable protecting groups for hydroxy groups that may be used are described in "*Protective Groups in Organic Synthesis* (Fourth Edition)", eds. Peter G. M. Wuts and Theodora W. Greene, Wiley-Interscience Publishers, (2007). Example of such a transformation can be found in the literature such as Tetrahedron Letters, 1994, 35, 219-222 ("A mild method for the conversion of activated aryl methyl groups to carboxaldehydes via the uncatalyzed periodate cleavage of enamines" by M. G. Vetelino and J. W. Coe). If necessary the carboxyl group of the nicotinic acid derivative may be protected prior to the reaction including, but not limited to, as an ester such as 2-chloro-6-methyl-nicotinic acid methyl ester.

The aldehydes of formula (IVa) can be prepared by oxidative cleavage of the alkene moiety of compound of formula (IIIa). Such a transformation is well known to those skilled in the art and can be realized for example with ozone, potassium permanganate and sodium metaperiodate. The process may be carried out optionally in a solvent such as methylene chloride, diethylether, chloroform, and generally at temperatures between about −100° C. and about 100° C. A summary of such methods is found in "Comprehensive Organic Transformations", VCH Publishers, (1989), R. C. Larock, pp. 595-596.

Reaction of the formyl nicotonic acid derivative of formula (IVa) with hydroxylamine provides the 2-halo-6-hydroxyiminomethyl pyridine derivative of formula (Va).

Treatment of the 2-halo-6-hydroxyiminomethyl pyridine derivative of formula (Va) with a halogenating reagent to yield chlorooxime intermediate of formula (Yb) followed by treatment with a vinylbenzene derivative of formula (VII) including, but not limited to, 1,3-bisfluoromethyl-5-(1-trifluoromethylvinyl)-benzene or 1,3-dichloro-5-(1-trifluoromethylvinyl)-benzene, provides the isoxazoline ring in the compound of formula (VIa). The reaction proceeds via a 1,3-dipolar [3+2]-cycloaddition reaction of the vinylbenzene derivative of formula (VII) with an intermediate nitrile oxide of formula (Vc), which is produced from dehydrohalogenation of the chlorooxime intermediate of formula (Yb). In some embodiments, the reaction may be conducted in the presence of a suitable base, including an amine base such as a triethylamine, diisopropylethylamine, N-ethylmorpholine, pyridine, and the like, to facilitate the formation of the nitrile oxide compound of formula (Vc). Suitable halogenating reagents include, but are not limited to, N-chlorosuccinimide, N-bromosuccinimide, sodium hypochlorite, chloramine-T, and the like.

An overview of such 1,3-dipolar [3+2]-cycloaddition reactions is available in "*March's Advanced Organic Chemistry: Reactions, Mechanisms, and Structure* (Sixth Edition)", Michael B. Smith and Jerry March, Wiley-Interscience Publishers, (2007), pp 1187-1192 and references cited therein.

Formation of the bicyclic group G-2 in compounds of formula (Ia-d), may be achieved by treatment of a 2-alkynyl-substituted pyridine derivative of formula (VIb) with a transition metal-catalyst, such as, but not limited to, copper (I), platinium(II), silver or gold, in a suitable solvent. Examples of such transition metal-catalyzed cycloisomerization to form heterocyclic framework are described in the literature (V. Gevorgyan et al, *Organic Letters*, 2008, 10, 2307-2310; 2007, 9, pages 3433-3436; *J. Am. Chem. Soc.*, 2001, 123, 2074-2075; *J. Am. Chem. Soc.*, 2006, 128, 12050-12051; *J. Am. Chem. Soc.*, 2007, 129, 9868-9878; Y. Liu et al, *Organic Letters*, 2007, 9, 409-412 & 4323-4326; *J. Org. Chem.*, 2007, 72, 7783-7786; A. Hayford et al, *Organic Letters*, 2005, 7, 4305-4308; R. Sarpong et al, *Organic Letters*, 2007, 9, 1169-1171 & 4547-4550; 2007, 9, 1169-1171M-M. Cid et al, *Organic Letters*, 2009, 11, 4802-4805; L. Sun et al, *Organic Process Research & Development*, 2007, 11, 1246-250).

The 2-alkynyl-substituted compound of formula (VIb) may be prepared by coupling reaction of a 2-halo-nicotinic acid derivative of formula (VIa) with an optionally substituted alkyne compound of formula (VIIIa-c) and a palladium catalyst. Those skilled in the art will recognize this coupling reaction when the substituted alkyne is a compound of formula (VIIIa) as a Sonogashira coupling reaction. See for example K. Sonogashira, Y. Tohda, N. Hagihara, "A convenient synthesis of acetylenes: catalytic substitutions of acetylenic hydrogen with bromoalkenes, iodoarenes and bromopyridines". *Tetrahedron Letters*, 1975, 16, 4467-4470. When the substituted alkyne is a compound of formula (VIIIb), including alkynyl stannane compound, this coupling reaction is known as a Stille coupling reaction. See for example D. Milstein, J. K. Stille, *J. Am. Chem. Soc.*, 1978, 100, 3636 and J. K. Stille, *Angew. Chem. Int. Ed. Engl.* 1986, 25, 508-524. A description of such methods is also found in "March's Advanced Organic Chemistry: Reactions, Mechanisms, and Structure (Sixth Edition)", Michael B. Smith and Jerry March, Wiley-Interscience Publishers, (2007) pp. 792-795. When the substituted alkyne is a compound of formula (VIIIc), including, but not limited to, alkynyl boronate ester or boronic acid compound, this coupling reaction is known as a Suzuki-Miyaura coupling reaction. Examples of such reaction can be found in A. Coehlo et al, *Synlett*, 2002, 12, 2062-2064. and an overview of Suzuki-Miyaura coupling reactions is described in N. Miyaura, A. Suzuki, *Chem. Rev.*, 1995, 95, 2457-2483. The solvent to be used in the reaction includes, for example but not limited to, ethers such as tetrahydrofuran, dioxane and the like, halogenated hydrocarbons such as such as 1,2-dichloroethane and the like, aromatic solvent such as benzene, toluene, xylene and the like. The reaction temperature is usually in the range of 0° C. to 200° C., preferably in the range of 20° C. to 120° C. and the reaction time is usually in the range of about 0.5 to 72 hours.

If desired, the carboxyl group present in the compound of formula (Ia) may be deprotected and coupled with a suitable amine using well known coupling conditions to provide the desired compound of formula (Id). Many procedures are available for forming amide bonds between a carboxylic acid derivative of formula (Ib) and an amine with the use of coupling agents. Procedures have been developed which use reagents such as carbodiimides as amide coupling agents. These carbodiimides include for example dicyclohexylcarbodiimide (DCC), diisopropylcarbodiimide (DIC), 1-(3-dimethylaminopropyl)-3-ethylcarbodiimide hydrochloride (EDC) and the like. Other amide coupling agents known in the art such as 1-ethoxycarbonyl-2-dihydroquinoline (EEDQ), phosphonium (e.g. phosphonium hexafluorophosphate (BOP), and others) or uronium-based reagents (e.g. TBTU, HATU and others) may also be used to form the amide bonds. In addition, anhydrides may also be utilized to form the desired amide bond. Catalysts such as 1-hydroxybenzotriazole (HOBT) and derivatives thereof have also been used. A summary of such methods is found in "*Comprehensive Organic Transformations*", R. C. Larock, VCH Publishers (1989) pp. 972-972. An overview of such transformations is also available in "*March's Advanced Organic Chemistry: Reactions, Mechanisms, and Structure* (Sixth Edition)", Michael B. Smith and Jerry March, Wiley-Interscience Publishers, (2007), pp 1431-1434.

Another general reaction for the preparation of amide derivatives such as compound of formula (Id) is the treatment of acyl halides such as compound of formula (Ic) with an amine. Such a transformations are well known to those skilled in the art and an overview of such transformations is available in "March's Advanced Organic Chemistry: Reactions, Mechanisms, and Structure (Sixth Edition)", Michael B. Smith and Jerry March, Wiley-Interscience Publishers, (2007), pp. 1427-1429.

Compounds of formula (I) where G is G-2, $B_1$ is N, $B_3$ is C—H, $B_2$, is C—H or C—$R^{17}$, $A_1$ is oxygen, $A_2$ is $CH_2$, $R_1$ is $CF_3$, X is an optionally substituted phenyl group, and Y may be Y-1, Y-2, Y-4, Y-5, Y-6, Y-7, Y-8 or Y-9, where $R_{10}$ and $R_{11}$ together form C=O, and $R_2$, $R_3$, $R_4$, $R_7$, $R_8$, $R_{12}$, $R_{13}$ and n are as defined above, may be prepared by the process shown in Scheme 2 below.

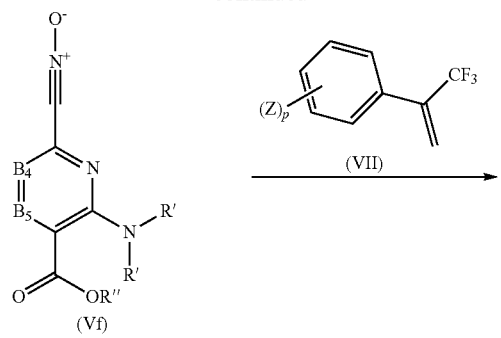

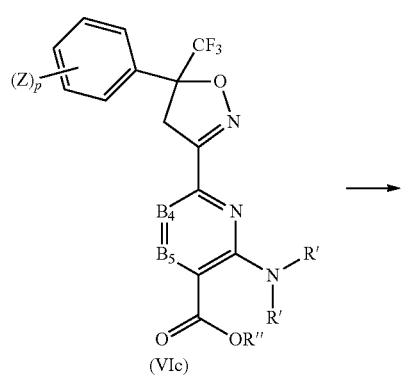

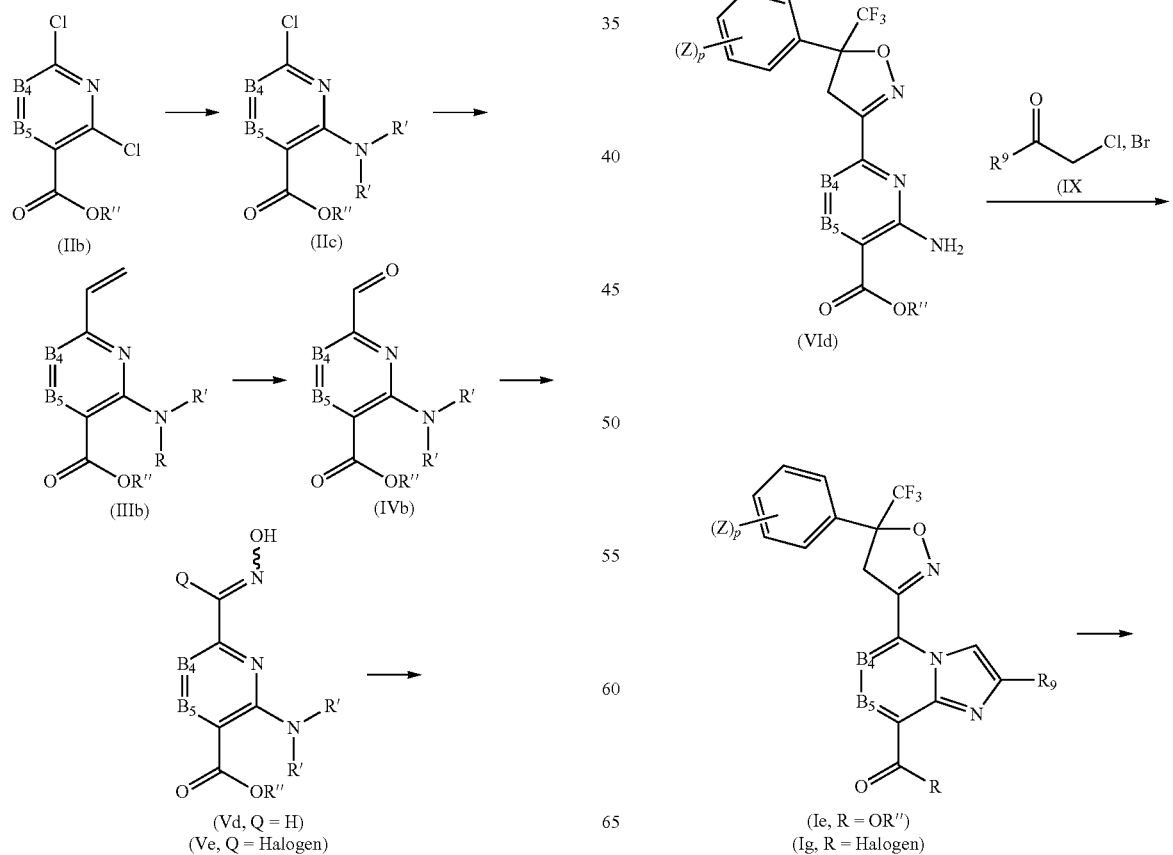

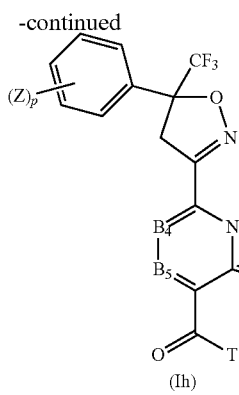

(Ih)

Where R is H or PG;
Where R" is H, alkyl or PG;
Where T is $NR_2R_3$,

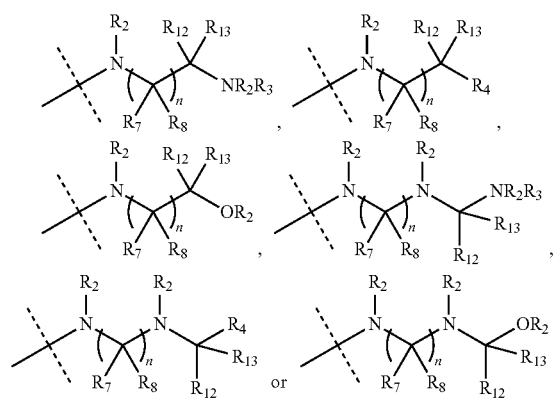

where $R_2$, $R_3$, $R_4$, $R_7$, $R_8$, $R_{12}$, $R_{13}$ and n are as defined above.

A 2,6-dihalonicotinic acid derivative of formula (IIb) where R" is H or a hydroxy protecting group (PG) including, but not limited to, 2,6-dichloronicotinic acid, which may be protected if necessary, is reacted with ammonium hydroxide or another suitable amine equivalent in a suitable solvent to provide a 2-amino-6-halo nicotinic acid derivative of formula (IIc) such as 2-amino-6-chloro nicotinic acid where R' is H or a protected derivative thereof. Suitable protecting groups for hydroxy groups that may be used are described in "*Protective Groups in Organic Synthesis* (Fourth Edition)", eds. Peter G. M. Wuts and Theodora W. Greene, Wiley-Interscience Publishers, (2007). See for examples of such transformations Y. Wensheng et al, Schering Corp. and Pharmacopeia Drug Discovery, WO2006088836.

The product of formula (IIc) is coupled with a vinylic metal reagent in the presence of a suitable catalyst such as a palladium catalyst to produce a compound of formula (IIIb) such as 2-amino-6-vinylic nicotinic acid where R' and R" are H or a protected derivative thereof where R' and/or R" is PG. When vinyl stannane reagents are used, this coupling reaction is known as a Stille coupling reaction with literature references previously cited above. The 2-amino group may be protected if required, where R' are amino protecting groups (PG) as defined in "*Protective Groups in Organic Synthesis* (Fourth Edition)", eds. Peter G. M. Wuts and Theodora W. Greene, Wiley-Interscience Publishers, (2007), pp. 696-926. The aldehydes of formula (IVb) can be prepared as in scheme 1 by oxidative cleavage of the alkene moiety of compound of formula (IIIb).

Reaction of the formyl nicotonic acid derivative of formula (IVb) with hydroxylamine or a hydroxylamine equivalent provides the hydroxyiminomethyl pyridine derivative of formula (Vd). Similar treatment of the hydroxyiminomethyl pyridine derivative of formula (Vd) as in scheme 1 with a halogenating reagent to yield chlorooxime intermediate of formula (Ve) followed by treatment with a vinylbenzene derivative of formula (VII) provides the isoxazoline ring in compound of formula (VIc) via a 1,3-dipolar [3+2]-cycloaddition reaction of the vinylbenzene derivative of formula (VII) with an intermediate nitrile oxide of formula (Vf).

Removal of any amine protecting group if required can be achieved by standard methods known by those skilled in the art as described in "*Protective Groups in Organic Synthesis* (Fourth Edition)", eds. Peter G. M. Wuts and Theodora W. Greene, Wiley-Interscience Publishers, (2007), pp. 696-926. Treatment of the amino pyridine compound of formula (VId) with an α-halocarbonyl compound, including, but not limited to, α-chloroacetaldehyde, provides the bicyclic aromatic group G-2 where $B_1$ is nitrogen present in compound of formula (Ie-g). Deprotection of the carbocylic acid group, if required, followed by coupling with a desired amino group similarly to method described in scheme 1 produces the compounds of formula (Ih).

Compounds of formula (I) where G is G-1, $B_1$ is C—H or C—$R_{14}$, $B_2$ and $B_3$, are C—H, Al is oxygen, $A_2$ is $CH_2$, $R_1$ is $CF_3$, X is an optionally substituted phenyl group, and Y may be Y-1, Y-2, Y-4, Y-5, Y-6, Y-7, Y-8 or Y-9, where $R_{10}$ and $R_{11}$ together form C=O, and $R_2$, $R_3$, $R_4$, $R_7$, $R_8$, $R_{12}$, $R_{13}$ and n are as defined above, may be prepared by the process shown in Scheme 3 below.

Scheme 3

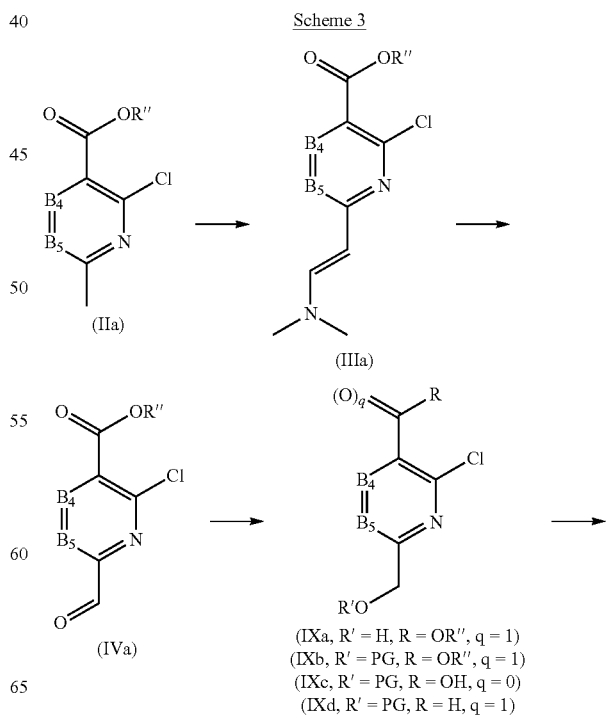

(IXa, R' = H, R = OR", q = 1)
(IXb, R' = PG, R = OR", q = 1)
(IXc, R' = PG, R = OH, q = 0)
(IXd, R' = PG, R = H, q = 1)

35
-continued
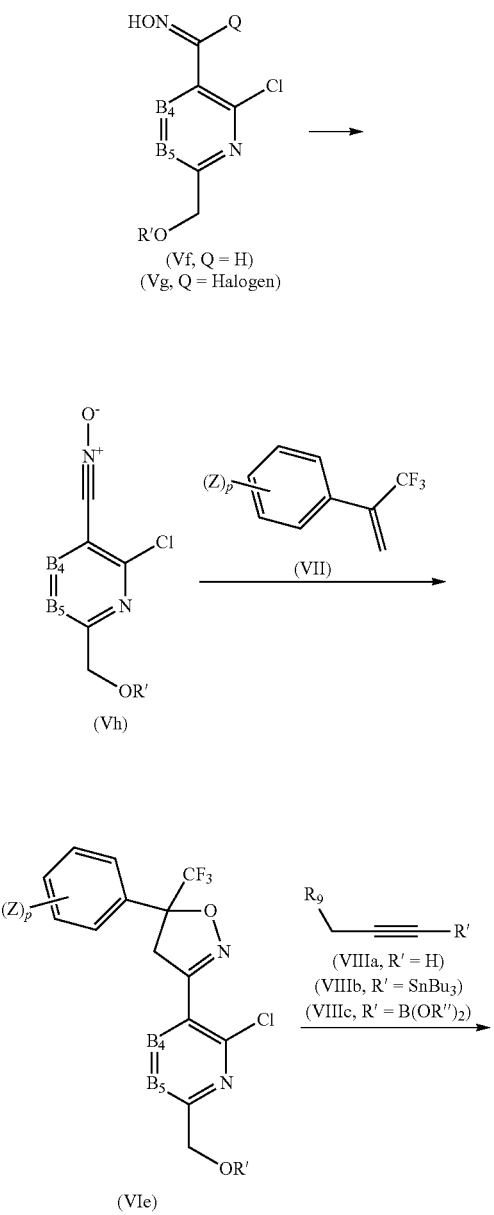
(Vf, Q = H)
(Vg, Q = Halogen)
(Vh)
(VIe)
(VIf)
36
-continued
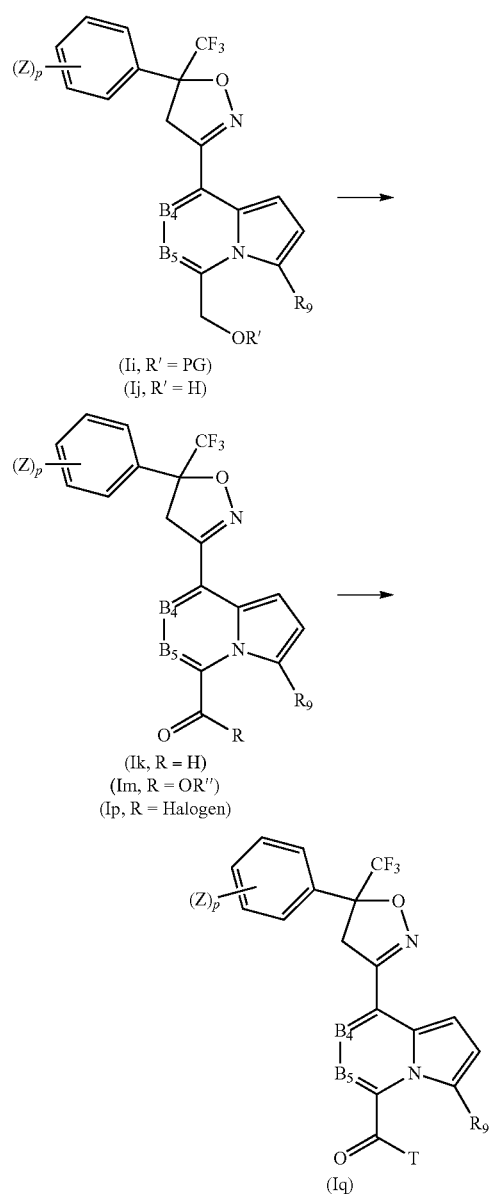
(Ii, R' = PG)
(Ij, R' = H)
(Ik, R = H)
(Im, R = OR'')
(Ip, R = Halogen)
(Iq)
Where R' is H or PG;
Where R'' is H, alkyl or PG;
Where T is $NR_2R_3$,
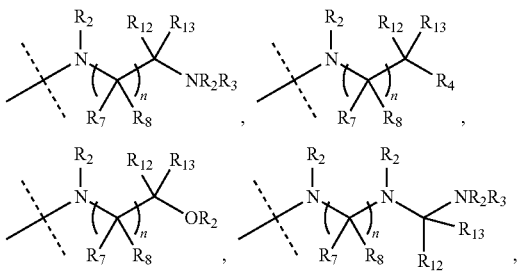

-continued

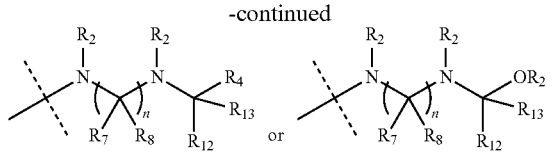

where $R_2$, $R_3$, $R_4$, $R_7$, $R_8$, $R_{12}$, $R_{13}$ and n are as defined above.

The aldehydes of formula (IVa) can be prepared following similar methods described in Scheme 1. Selective reduction of the aldehyde of formula (IVa) can be accomplished by treatment with a reducing agent such as, but not limited to, sodium cyanoborohydride, sodium borohydride, sodium triacetoxyborohydride, L-SELECTRIDE® (lithium tri-sec-butyl(hydrido)borate), decaborane and the like to produce alcohol derivatives of formula (IXa). A summary of such methods is found in "Comprehensive Organic Transformations", VCH Publishers, (1989), R. C. Larock, pp. 527-536. The solvent to be used in the reaction includes, for example but not limited to, ethers such as diethylether, tetrahydrofuran and the like, halogenated hydrocarbon such as such as methylene chloride, chloroform, 1,2-dichloroethane and the like. The reaction temperature is usually in the range of −78° C. to 150° C., preferably in the range of 0° C. to 80° C. and the reaction time is usually in the range of 1 to 72 hours.

The hydroxyl group present in alcohol derivatives of formula (IXa) can be protected to yield compounds of formula (IXb) with an appropriate protecting group (PG) such as, but not limited to, silyl ethers like tert-butyldimethylsilyl (tBDMS) and the like. An overview of methods available to protect the hydroxyl group is given in "Protective Groups in Organic Synthesis (Fourth Edition)", eds. Peter G. M. Wuts and Theodora W. Greene, Wiley-Interscience Publishers, (2007), pp. 16-299.

The acid or ester group present in compounds of formula (IXb) can be reduced by treatment with a reducing agent such as, but not limited to, lithium aluminum hydride, lithium borohydride, sodium borohydride and the like to yield alcohol derivatives of formula (IXc) or to yield directly aldehydes derivatives of formula (IXd) with a reducing agent such as, but not limited to, diisobutyl aluminum hydride (DIBAL-H). The reaction is usually performed in a solvent such as dialkyl ether (e.g. diethyl ether), tetrahydrofuran (THF) and generally at temperatures between about −100° C. and about 40° C. A summary of such methods is found in "Comprehensive Organic Transformations", VCH Publishers, (1989), R. C. Larock, pp. 548-552.

The hydroxyl group present in derivatives of formula (IXc) can be oxidized to yield aldehydes of formula (IXd) by treatment with oxidizing agents such as, but not limited to, dimethylsulfoxide (DMSO) based reagents, nitroxyl radical reagents like 2,2,6,6-tetramethylpiperidine-1-oxyl (TEMPO), hypervalent iodine reagents like 1,1,1-triacetoxy-1,1-dihydro-1,2-benziodoxol-3(1H)-one (the so called Dess-Martin periodinane reagent) and the like. An overview of such transformations is available in "March's Advanced Organic Chemistry: Reactions, Mechanisms, and Structure (Sixth Edition)", Michael B. Smith and Jerry March, Wiley-Interscience Publishers, (2007), section 19-3 "Oxidation or Dehydrogenation of Alcohols to Aldehydes and Ketones" pp. 1715-1728.

Reaction of the aldehyde derivatives of formula (IXd) with hydroxylamine or an hydroxylamine equivalent provides the hydroxyiminomethyl pyridine derivatives of formula (Vf). Similar treatment of the hydroxyiminomethyl pyridine derivative of formula (Vf) as in scheme 1 with a halogenating reagent to yield chlorooxime intermediate of formula (Vg) followed by treatment with a vinylbenzene derivative of formula (VII) provides the isoxazoline ring in compound of formula (VIe) via a 1,3-dipolar [3+2]-cycloaddition reaction of the vinylbenzene derivative of formula (VII) with an intermediate nitrile oxide of formula (Vh).

The alkynyl-substituted compound of formula (VII) may be prepared by coupling reaction of a halo-derivative of formula (VIe) with an optionally substituted alkyne compound of formula (VIIIa-c) and a palladium catalyst using similar methodology described in scheme 1.

Formation of the bicyclic group G-1 in compounds of formula (Ii-j), may be achieved by treatment of a alkynyl-substituted pyridine derivative of formula (VIf) with a transition metal-catalyst, such as, but not limited to, copper (I), platinium(II), silver or gold, in a suitable solvent using similar methodology described in scheme 1.

Removal of the hydroxyl protecting group present in compounds of formula (Ii) to yield alcohol derivatives of formula (Ij) can be achieved by standard methods known by those skilled in the art. A summary of such methods can be found in "Protective Groups in Organic Synthesis (Fourth Edition)", eds. Peter G. M. Wuts and Theodora W. Greene, Wiley-Interscience Publishers, (2007), pp. 16-299.

The hydroxyl group present in derivatives of formula (Ij) can be oxidized to yield aldehyde derivatives of formula (Ik) by treatment with oxidizing agents such as, but not limited to, those described above to yield compounds of formula (IXd). The hydroxyl group present in derivatives of formula (Ij) or the aldehyde derivatives of formula (Ik) can be oxidized to yield acid of formula (In) by treatment with oxidizing agents such as, but not limited to, potassium permanganate, chromic acid, a combination of tetramethylpiperidine-1-oxyl (TEMPO) and sodium chlorite. An overview of such transformations is available in "March's Advanced Organic Chemistry: Reactions, Mechanisms, and Structure (Sixth Edition)", Michael B. Smith and Jerry March, Wiley-Interscience Publishers, (2007), section 19-22 "Oxidation of Primary Alcohols to Carboxylic Acids or Carboxylic Esters" pp. 1768-1769 and section 19-23 "Oxidation of Aldehydes to Carboxylic Acids" pp. 1769-1773.

Coupling of the acid derivative of formula (In) or of the acyl derivative of formula (Ip) with a desired amino group similarly to method described in scheme 1 produces the compound of formula (Iq)

It will be appreciated by those of skill in the art that alternate reagents and conditions may be used to produce compounds with different substitution patterns.

The invention further contemplates separating the enantiomers in whole or in part of the present invention or synthesizing enantiomerically enriched compounds of the invention. The composition may be prepared by separating the enantiomers in whole or in part by standard methods, for example by chemical resolution using optically active acid or by use of column chromatography or reverse-phase column chromatography using a substantially optically active (or "chiral") stationary phase as known to those skilled in the art. The formation and/or isolation of specific enantiomers of a compound is not routine, and there are no general methods that may be used to obtain specific enantiomers of all compounds. The methods and conditions used to obtain specific enantiomers of a compound must be determined for each specific compound. Enantiomerically enriched compounds of the invention can also be obtained from enantiomerically enriched precursors.

Veterinary Compositions

Another aspect of the invention is the formation of parasiticidal compositions which comprise the dihydroazole compounds of the invention. The composition of the invention can also be in a variety of forms which include, but are not limited to, oral formulations, injectable formulations, and topical, dermal or subdermal formulations. The formulations are intended to be administered to an animal which includes but is not limited to mammals, birds and fish. Examples of mammals include but are not limited to humans, cattle, sheep, goats, llamas, alpacas, pigs, horses, donkeys, dogs, cats and other livestock or domestic mammals. Examples of birds include turkeys, chickens, ostriches and other livestock or domestic birds.

The composition of the invention may be in a form suitable for oral use, for example, as baits (see, e.g., U.S. Pat. No. 4,564,631, incorporated herein by reference), dietary supplements, troches, lozenges, chewables, tablets, hard or soft capsules, emulsions, aqueous or oily suspensions, aqueous or oily solutions, oral drench formulations, dispersible powders or granules, premixes, syrups or elixirs, enteric formulations or pastes. Compositions intended for oral use may be prepared according to any method known in the art for the manufacture of pharmaceutical compositions and such compositions may contain one or more agents selected from the group consisting of sweetening agents, bittering agents, flavoring agents, coloring agents and preserving agents in order to provide pharmaceutically elegant and palatable preparations.

Tablets may contain the active ingredient in admixture with non-toxic, pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example, magnesium stearate, stearic acid or talc, the tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in U.S. Pat. Nos. 4,256,108; 4,166,452; and 4,265,874 (incorporated herein by reference) to form osmotic therapeutic tablets for controlled release.

Formulations for oral use may be hard gelatin capsules, wherein the active ingredient is mixed with an inert solid diluent, for example, calcium carbonate, calcium phosphate or kaolin. Capsules may also be soft gelatin capsules, wherein the active ingredient is mixed with water or miscible solvents such as propylene glycol, polyethylene glycols (PEGs) and ethanol, or an oil medium, for example peanut oil, liquid paraffin, or olive oil.

The compositions of the invention may also be in the form of oil-in-water or water-in-oil emulsions. The oily phase may be a vegetable oil, for example, olive oil or arachis oil, or a mineral oil, for example, liquid paraffin or mixtures of these. Suitable emulsifying agents may be naturally-occurring phosphatides, for example, soybean, lecithin, and esters or partial esters derived from fatty acids and hexitol anhydrides, for example, sorbitan monoleate, and condensation products of the said partial esters with ethylene oxide, for example, polyoxyethylene sorbitan monooleate. The emulsions may also contain sweetening agents, bittering agents, flavoring agents, and/or preservatives.

In one embodiment of the formulation, the composition of the invention is in the form of a microemulsion. Microemulsions are well suited as the liquid carrier vehicle. Microemulsions are quaternary systems comprising an aqueous phase, an oily phase, a surfactant and a cosurfactant. They are translucent and isotropic liquids.

Microemulsions are composed of stable dispersions of microdroplets of the aqueous phase in the oily phase or conversely of microdroplets of the oily phase in the aqueous phase. The size of these microdroplets is less than 200 nm (1000 to 100,000 nm for emulsions). The interfacial film is composed of an alternation of surface-active (SA) and co-surface-active (Co-SA) molecules which, by lowering the interfacial tension, allows the microemulsion to be formed spontaneously.

In one embodiment of the oily phase, the oily phase can be formed from mineral or vegetable oils, from unsaturated polyglycosylated glycerides or from triglycerides, or alternatively from mixtures of such compounds. In one embodiment of the oily phase, the oily phase comprises of triglycerides; in another embodiment of the oily phase, the triglycerides are medium-chain triglycerides, for example $C_8$-$C_{10}$ caprylic/capric triglyceride. In another embodiment of the oily phase will represent a % v/v range selected from the group consisting of about 2 to about 15%; about 7 to about 10%; and about 8 to about 9% v/v of the microemulsion.

The aqueous phase includes, for example water or glycol derivatives, such as propylene glycol, glycol ethers, polyethylene glycols or glycerol. In one embodiment of the glycol derivatives, the glycol is selected from the group consisting of propylene glycol, diethylene glycol monoethyl ether, dipropylene glycol monoethyl ether and mixtures thereof. Generally, the aqueous phase will represent a proportion from about 1 to about 4% v/v in the microemulsion.

Surfactants for the microemulsion include diethylene glycol monoethyl ether, dipropyelene glycol monomethyl ether, polyglycolyzed $C_8$-$C_{10}$ glycerides or polyglyceryl-6 dioleate. In addition to these surfactants, the cosurfactants include short-chain alcohols, such as ethanol and propanol.

Some compounds are common to the three components discussed above, i.e., aqueous phase, surfactant and cosurfactant. However, it is well within the skill level of the practitioner to use different compounds for each component of the same formulation. In one embodiment for the amount of surfactant/cosurfactant, the cosurfactant to surfactant ratio will be from about 1/7 to about 1/2. In another embodiment for the amount of cosurfactant, there will be from about 25 to about 75% v/v of surfactant and from about 10 to about 55% v/v of cosurfactant in the microemulsion.

Oily suspensions may be formulated by suspending the active ingredient in a vegetable oil, for example, atachis oil, olive oil, sesame oil or coconut oil, or in mineral oil such as liquid paraffin. The oily suspensions may contain a thickening agent, for example, beeswax, hard paraffin or cetyl alcohol. Sweetening agents such as sucrose, saccharin or aspartame, bittering agents, and flavoring agents may be added to provide a palatable oral preparation. These compositions may be preserved by the addition of an antioxidant such as ascorbic acid, or other known preservatives.

Aqueous suspensions may contain the active material in admixture with excipients suitable for the manufacture of aqueous suspensions. Such excipients are suspending agents, for example, sodium carboxymethylcellulose, methylcellulose, hydroxy-propylmethylcellulose, sodium alginate, polvinylpyrrolidone, gum tragacanth and gum acacia; dispersing or wetting agents may be a naturally-ocurring phosphatide, for example lecithin, or condensation products of an alkylene oxide with fatty acids, for example polyoxyethylene stearate, or condensation products of ethylene oxide with long chain aliphatic alcohols, for example, heptadecaethyleneoxycetanol, or condensation products of ethylene oxide with partial esters derived from fatty acids and a hexitol such as polyoxyethylene sorbitol monooleate, or condensation products of ethylene oxide, with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents and/or bittering agents, such as those set forth above.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example, sweetening, bittering, flavoring and coloring agents, may also be present. Syrups and elixirs may be formulated with sweetening agents, for example, glycerol, propylene glycol, sorbitol or sucrose. Such formulations may also contain a demulcent, a preservative, flavoring agent(s) and/or coloring agent(s).

In another embodiment of the invention, the composition can be in paste form. Examples of embodiments in a paste form include but are not limited to those described in U.S. Pat. Nos. 6,787,342 and 7,001,889 (each of which are incorporated herein by reference). In addition to the dihydroazole compound of the invention, the paste can also contain fumed silica; a viscosity modifier; a carrier; optionally, an absorbent; and optionally, a colorant, stabilizer, surfactant, or preservative.

The process for preparing a paste formulation comprises the steps of:
(a) dissolving or dispersing the dihydroazole compound into the carrier by mixing;
(b) adding the fumed silica to the carrier containing the dissolved dihydroazole compound and mixing until the silica is dispersed in the carrier;
(c) allowing the intermediate formed in (b) to settle for a time sufficient in order to allow the air entrapped during step (b) to escape; and
(d) adding the viscosity modifier to the intermediate with mixing to produce a uniform paste.

The above steps are illustrative, but not limiting. For example, step (a) can be the last step.

In one embodiment of the formulation, the formulation is a paste containing dihydroazole compound, fumed silica, a viscosity modifier, an absorbent, a colorant; and a hydrophilic carrier which is triacetin, a monoglyceride, a diglyceride, or a triglyceride.

The paste may also include, but is not limited to, a viscosity modifier including PEG 200, PEG 300, PEG 400, PEG 600, monoethanolamine, triethanolamine, glycerol, propylene glycol, polyoxyethylene (20) sorbitan monooleate (POLYSORBATE 80 or TWEEN 80), and polyoxamers (e.g., PLURONIC L 81); an absorbent including magnesium carbonate, calcium carbonate, starch, and cellulose and its derivatives; and a colorant selected from the group consisting of titanium dioxide iron oxide, and FD&C Blue #1 ALUMINUM LAKE.

The compositions may be in the form of a sterile injectable aqueous or oleagenous suspension or an injectable solution. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example, as a solution in 1,3-butane diol. Among the acceptable vehicles and solvents that may be employed are water, Ringer's solution and isotonic sodium chloride solution. Cosolvents such as ethanol, propylene glycol glycerol formal or polyethylene glycols may also be used. Preservatives, such as phenol or benzyl alcohol, may be used.

In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Topical, dermal and subdermal formulations can include emulsions, creams, ointments, gels, pastes, powders, shampoos, pour-on formulations, spot-on solutions and suspensions, dips and sprays. Topical application of an inventive compound or of a composition including at least one inventive compound among active agent(s) therein, in the form of a spot-on or pour-on composition, can allow for the inventive compound to be absorbed through the skin to achieve systemic levels, distributed through the sebaceous glands or on the surface of the skin achieving levels throughout the haircoat. When the compound is distributed through the sebaceous glands, they can act as a reservoir, whereby there can be a long-lasting effect (up to several months) effect. Spot-on formulations are typically applied in a localized region which refers to a relatively small area on the animal rather than to a large portion of the surface of the animal. In one embodiment of a localized region, the location is between the shoulders. In another embodiment of a localized region it is a stripe, e.g. a stripe from head to tail of the animal.

Pour-on formulations are described in U.S. Pat. No. 6,010,710, incorporated herein by reference. In some embodiments, the pour-on formulations may be oily, and generally comprise a diluent or vehicle and also a solvent (e.g. an organic solvent) for the active ingredient if the latter is not soluble in the diluent. In other embodiments, the pour-on formulations may be non-oily, including alcohol-based formulations.

Organic solvents that can be used in the invention include but are not limited to: acetyltributyl citrate, fatty acid esters such as the dimethyl ester, acetone, acetonitrile, benzyl alcohol, butyl diglycol, dimethylacetamide, dimethylformamide, dipropylene glycol n-butyl ether, ethanol, isopropanol, methanol, ethylene glycol monoethyl ether, ethylene glycol monomethyl ether, monomethylacetamide, dipropylene glycol monomethyl ether, liquid polyoxyethylene glycols, propylene glycol, 2-pyrrolidone including N-methylpyrrolidone, diethylene glycol monoethyl ether, propylene glycol monomethyl ether, propylene glycol monoethyl ether, ethylene glycol, diisobutyl adipate, diisopropyl adipate (also known as CERAPHYL 230), triacetin, butyl acetate, octyl acetate, propylene carbonate, butylene carbonate, dimethylsufoxide, organic amides including dimethylformamide and dimethylacetamide, and diethyl phthalate, or a mixture of at least two of these solvents.

In one embodiment of the invention, the pharmaceutically or veterinarily acceptable carrier of the formulation comprises $C_1$-$C_{10}$ alcohols or esters thereof (including acetates, such as ethyl acetate, butyl acetate and the like), $C_{10}$-$C_{18}$ saturated fatty acids or esters thereof, $C_{10}$-$C_{18}$ monounsaturated fatty acids or esters thereof, monoesters or diesters of aliphatic diacids, glycerol monoesters (e.g. monoglycerides), glycerol diesters (e.g. diglycerides), glycerol triesters (e.g. triglycerides such as triacetin), glycols, glycol ethers, glycol esters or glycol carbonates, polyethylene glycols of various grades (PEGs) or monoethers, diethers, monoesters or diesters thereof (e.g. diethylene glycol monoethyl ether), or mixtures thereof.

As vehicle or diluent, mention may be made of plant oils such as, but not limited to soybean oil, groundnut oil, castor oil, corn oil, cotton oil, olive oil, grape seed oil, sunflower oil, coconut oils etc.; mineral oils such as, but not limited to, petrolatum, paraffin, silicone, etc.; aliphatic or cyclic hydrocarbons or alternatively, for example, medium-chain (such as C8 to C12) triglycerides.

In another embodiment of the invention, an emollient and/or spreading and/or film-forming agent can be added. In one embodiment, the emollient and/or spreading and/or film-forming agent are those agents selected from the group consisting of:

(a) polyvinylpyrrolidone, polyvinyl alcohols, copolymers of vinyl acetate and vinylpyrrolidone, polyethylene glycols, benzyl alcohol, 2-pyrrolidones including, but not limited to N-methylpyrrolidone, mannitol, glycerol, sorbitol, polyoxyethylenated sorbitan esters; lecithin, sodium carboxymethylcellulose, silicone oils, polydiorganosiloxane oils (such as polydimethylsiloxane (PDMS) oils), for example those containing silanol functionalities, or a 45V2 oil, (b) anionic surfactants such as alkaline stearates, sodium, potassium or ammonium stearates; calcium stearate, triethanolamine stearate; sodium abietate; alkyl sulphates (e.g. sodium lauryl sulphate and sodium cetyl sulphate); sodium dodecylbenzenesulphonate, sodium dioctylsulphosuccinate; fatty acids (e.g. those derived from coconut oil), (c) cationic surfactants such as water-soluble quaternary ammonium salts of formula $N^+R'R''R'''R''''$, $Y^-$ in which the radicals R are optionally hydroxylated hydrocarbon radicals and $Y^-$ is an anion of a strong acid such as the halide, sulphate and sulphonate anions; cetyltrimethylammonium bromide is among the cationic surfactants which can be used, (d) amine salts of formula $N^+HR'R''R'''$ in which the radicals R are optionally hydroxylated hydrocarbon radicals; octadecyl amine hydrochloride is among the cationic surfactants which can be used, (e) nonionic surfactants such as sorbitan esters, which are optionally polyoxyethylenated (e.g. POLYSORBATE 80), polyoxyethylenated alkyl ethers; polyoxypropylated fatty alcohols such as polyoxypropylene-styrol ether; polyethylene glycol stearate, polyoxyethylenated derivatives of castor oil, polyglycerol esters, polyoxyethylenated fatty alcohols, polyoxyethylenated fatty acids, copolymers of ethylene oxide and propylene oxide, (f) amphoteric surfactants such as the substituted lauryl compounds of betaine; or (g) a mixture of at least two of these agents.

The solvent will be used in proportion with the concentration of the dihydroazole compound and its solubility in this solvent. It will be sought to have the lowest possible volume. The vehicle makes up the difference to 100%.

In one embodiment of the amount of emollient, the emollient is used in a proportion of from 0.1 to 50% and 0.25 to 5%, by volume.

In another embodiment of the invention, the composition can be in ready-to-use solution for localized topical application, including a spot-on formulation, as is described in U.S. Pat. No. 6,395,765, incorporated herein by reference. In addition to the dihydroazole compound, the solution may contain a crystallization inhibitor, an organic solvent and an organic co-solvent. In one embodiment of the amount of crystallization inhibitor, the crystallization inhibitor can be present in a proportion of about 1 to about 30% (w/v) in the composition. In other embodiments, the crystallization inhibitor may be present in a proportion of about 1 to about 20% (w/v) and about 5 to about 15%. Acceptable inhibitors are those whose addition to the formulation inhibits the formation of crystals when the formulation is applied. In some embodiments, formulations may include compounds that function as crystallization inhibitors other than those listed herein. In these embodiments, the suitability of a crystallization inhibitor may be determined by a the test in which 0.3 ml of a solution comprising 10% (w/v) of dihydroazole compound in the liquid carrier and 10% of the inhibitor are deposited on a glass slide at 20° C. and allowed to stand for 24 hours. The slide is then observed with the naked eye. Acceptable inhibitors are those whose addition provides for few (e.g. less than ten crystals) or no crystals.

In one embodiment, the organic solvent has a dielectric constant of about 2 to about 35, about 10 to about 35 or about 20 to about 30. In other embodiments, the solvent will have a dielectric constant of between about 2 and about 20, or between about 2 and about 10. The content of this organic solvent in the overall composition will complement to 100% of the composition.

As discussed above, the solvent may comprise a mixture of solvents including a mixture of an organic solvent and an organic co-solvent. In one embodiment, and the organic co-solvent has a boiling point of less than about 300° C. or less than about 250° C. In other embodiments, the co-solvent has a boiling point of below about 200° C., or below about 130° C. In still another embodiment of the invention, the organic co-solvent has a boiling point of below about 100° C., or below about 80° C. In still other embodiments, the organic co-solvent will have a dielectric constant of a range selected from the group consisting of about 2 to about 40, about 10 to about 40, or typically about 20 to about 30. In some embodiments of the invention, the co-solvent may be present in the composition in an organic co-solvent/organic solvent weight/weight (W/W) ratio of about 1/15 to about 1/2. In some embodiments, the co-solvent is volatile so as to act as a drying promoter, and is miscible with water and/or with the organic solvent.

The formulation can also comprise an antioxidizing agent intended to inhibit oxidation in air, this agent being present in a proportion selected from a range consisting of about 0.005 to about 1% (w/v) and about 0.01 to about 0.05%.

Crystallization inhibitors which are useful for the invention include but are not limited to:

(a) polyvinylpyrrolidone, polyvinyl alcohols, copolymers of vinyl acetate and of vinylpyrrolidone, polyethylene glycols of various grades, benzyl alcohol, 2-pyrrolidones including, but not limited to N-methylpyrrolidone, dimethylsufoxide, mannitol, glycerol, sorbitol or polyoxyethylenated esters of sorbitan; lecithin or sodium carboxymethylcellulose; a solvent as described herein that is capable of inhibiting crystal formation; acrylic derivatives, such as acrylates and methacrylates or other polymers derived from acrylic monomers, and others;

(b) anionic surfactants, such as alkaline stearates (e.g. sodium, potassium or ammonium stearate); calcium stearate or triethanolamine stearate; sodium abietate; alkyl sulphates, which include but are not limited to sodium lauryl sulphate and sodium cetyl sulphate; sodium dodecylbenzenesulphonate or sodium dioctyl sulphosuccinate; or fatty acids (e.g. coconut oil);
(c) cationic surfactants, such as water-soluble quaternary ammonium salts of formula $N^+R'R''R'''R''''Y^-$, in which the R radicals are identical or different optionally hydroxylated hydrocarbon radicals and Y is an anion of a strong acid, such as halide, sulphate and sulphonate anions; cetyltrimethylammonium bromide is one of the cationic surfactants which can be used;
(d) amine salts of formula $N^+HR'R''R'''$, in which the R radicals are identical or different optionally hydroxylated hydrocarbon radicals; octadecylamine hydrochloride is one of the cationic surfactants which can be used;
(e) non-ionic surfactants, such as optionally polyoxyethylenated esters of sorbitan, e.g. POLYSORBATE 80, or polyoxyethylenated alkyl ethers; polyethylene glycol stearate, polyoxyethylenated derivatives of castor oil, polyglycerol esters, polyoxyethylenated fatty alcohols, polyoxyethylenated fatty acids or copolymers of ethylene oxide and of propylene oxide;
(f) amphoteric surfactants, such as substituted lauryl compounds of betaine; or
(g) a mixture of at least two of the compounds listed in (a)-(f) above.

In one embodiment of the crystallization inhibitor, a crystallization inhibitor pair will be used. Such pairs include, for example, the combination of a film-forming agent of polymeric type and of a surface-active agent. These agents will be selected from the compounds mentioned above as crystallization inhibitor.

In one embodiment of the film-forming agent, the agents are of the polymeric type which include but are not limited to the various grades of polyvinylpyrrolidone, polyvinyl alcohols, and copolymers of vinyl acetate and of vinylpyrrolidone.

In one embodiment of the surface-active agents, the agents include but are not limited to those made of non-ionic surfactants; in another embodiment of the surface active agents, the agent is a polyoxyethylenated esters of sorbitan and in yet another embodiment of the surface-active agent, the agents include the various grades of POLYSORBATE, for example POLYSORBATE 80.

In another embodiment of the invention, the film-forming agent and the surface-active agent can be incorporated in similar or identical amounts within the limit of the total amounts of crystallization inhibitor mentioned elsewhere.

In one embodiment of the antioxidizing agents, the agents are those conventional in the art and include but is not limited to butylated hydroxyanisole, butylated hydroxytoluene, ascorbic acid, sodium metabisulphite, propyl gallate, sodium thiosulphate or a mixture of not more than two of them.

The non-active formulation components discussed above are well known to the practitioner in this art and may be obtained commercially or through known techniques. These concentrated compositions are generally prepared by simple mixing of the constituents as defined above; advantageously, the starting point is to mix the active material in the main solvent and then the other ingredients are added.

The volume of the topical formulations applied is not restricted as long as the amount of substance administered is shown to be safe and efficacious. Typically, the volume applied depends on the size and weight of the animal as well as the concentration of active, the extent of infestation by parasites and the type of administration. In some embodiments, the volume applied can be of the order of about 0.3 to about 5 ml or about 0.3 ml to about 1 ml. In one embodiment for the volume, the volume is on the order of about 0.5 ml, for cats and on the order of about 0.3 to about 3 ml for dogs, depending on the weight of the animal. In other embodiments, the volume applied may be about 5 ml to about 10 ml, about 5 ml to about 15 ml, about 10 ml to about 20 ml, or about 20 ml to about 30 ml, depending on the size of the animal treated and the concentration of the active agent in the formulation, among other factors.

In another embodiment of the invention, application of a spot-on formulation according to the present invention can also provide long-lasting and broad-spectrum efficacy when the solution is applied to the mammal or bird. The spot-on formulations provide for topical administration of a concentrated solution, suspension, microemulsion or emulsion for intermittent application to a spot on the animal, generally between the two shoulders (solution of spot-on type).

For spot-on formulations, the carrier can be a liquid carrier vehicle as described in U.S. Pat. No. 6,426,333 (incorporated herein by reference). In one embodiment, the spot-on formulation comprises a solvent and a cosolvent wherein the solvent may be acetone, acetonitrile, benzyl alcohol, butyl diglycol, dimethylacetamide, dimethylformamide, dipropylene glycol n-butyl ether, propylene glycol monomethyl ether, propylene glycol monoethyl ether, diisobutyl adipate, diisopropyl adipate (also known as CERAPHYL 230), triacetin, butyl acetate, octyl acetate, propylene carbonate, butylene carbonate, dimethylsufoxide, organic amides including dimethylformamide and dimethylacetamide, ethanol, isopropanol, methanol, ethylene glycol monoethyl ether, ethylene glycol monomethyl ether, monomethylacetamide, dipropylene glycol monomethyl ether, liquid polyoxyethylene glycols, propylene glycol, 2-pyrrolidone including N-methylpyrrolidone, diethylene glycol monoethyl ether, ethylene glycol, diethyl phthalate fatty acid esters, such as the diethyl ester or diisobutyl adipate, and a mixture of at least two of these solvents. In another embodiment, the spot-on formulations include a cosolvent that is absolute ethanol, isopropanol or methanol, or a mixture thereof. In another embodiment, the compositions include benzyl alcohol as a co-solvent.

In one embodiment of the invention, the pharmaceutically or veterinarily acceptable carrier of the formulation comprises $C_1$-$C_{10}$ alcohols or esters thereof (including acetates, such as ethyl acetate, butyl acetate and the like), $C_{10}$-$C_{18}$ saturated fatty acids or esters thereof, $C_{10}$-$C_{18}$ monounsaturated fatty acids or esters thereof, monoesters or diesters of aliphatic diacids, glycerol monoesters (e.g. monoglycerides), glycerol diesters (e.g. diglycerides), glycerol triesters (e.g. triglycerides such as triacetin), glycols, glycol ethers, glycol esters or glycol carbonates, polyethylene glycols of various grades (PEGs) or monoethers, diethers, monoesters or diesters thereof (e.g. diethylene glycol monoethyl ether), or mixtures thereof.

The liquid carrier vehicle can optionally contain a crystallization inhibitor including an anionic surfactant, a cationic surfactant, a non-ionic surfactant, an amine salt, an amphoteric surfactant or polyvinylpyrrolidone, polyvinyl alcohols, copolymers of vinyl acetate and vinylpyrrolidone, 2-pyrrolidone including N-methylpyrrolidone (NMP), dimethylsulfoxide, polyethylene glycols, benzyl alcohol, mannitol, glycerol, sorbitol, polyoxyethylenated sorbitan esters; lecithin, sodium carboxymethylcellulose, solvents as defined herein that can inhibit the formation of crystals, and acrylic derivatives such acrylates or methacrylates as well as other polymers derived from acrylic monomers, or a mixture of these crystallization inhibitors.

Spot-on formulations may be prepared by dissolving the active ingredients into the pharmaceutically or veterinary acceptable vehicle. Alternatively, the spot-on formulation can be prepared by encapsulation of the active ingredient to leave a residue of the therapeutic agent on the surface of the animal. These formulations will vary with regard to the weight of the therapeutic agent in the combination depending on the species of host animal to be treated, the severity and type of infection and the body weight of the host.

Dosage forms may contain from about 0.5 mg to about 5 g of an active agent. In one embodiment of the dosage form, the dosage is from about 1 mg to about 500 mg of an active agent. More typically the dosage is about 1 mg to about 25 mg, 1 mg to about about 50 mg, 10 mg to about about 100 mg, or 20 mg to about about 200 mg. In other embodiments, the dosage is about 50 mg to about about 300 mg, 50 mg to about about 400 mg, 50 mg to about about 500 mg, 50 mg to about about 600 mg, 50 mg to about about 800 mg, or 100 mg to about about 1000 mg.

In one embodiment of the invention, the active agent is present in the formulation at a concentration of about 0.05% to about 50% weight/volume. In other embodiments, the active agent may be present in the formulation at a concentration of about 0.1% to about 30%, about 0.5% to about 20% (w/v) or about 1% to about 10% (w/v). In another embodiment of the invention, the active agent is present in the formulation as a concentration from about 0.1 to 2% weight/volume. In yet another embodiment of the invention, the active agent is present in the formulation as a concentration from about 0.25 to about 1.5% weight/volume. In still another embodiment of the invention, the active agent is present in the formulation as a concentration about 1% weight/volume.

In a particular advantageous embodiment of the invention, the dose of the inventive compounds is about 0.01 mg/kg to about 100 mg/kg of weight of animal. In another embodiment, the dose is about 0.1 mg/kg to about 100 mg/kg of weight of animal. In other embodiments, the dose of the inventive compounds is about 0.5 mg/kg to about 70 mg/kg, about 0.5 mg/kg to about 50 mg/kg or about 0.5 mg/kg to about 30 mg/kg. In other preferred embodiments, the dose is 0.5 mg/kg to about 30 mg/kg, 0.5 mg/kg to about 20 mg/kg or 0.5 mg/kg to about 10 mg/kg. More typically, in some embodiments the dose of the active compounds is about 0.01 mg/kg to 5 mg/kg, 0.1 mg/kg to about 5 mg/kg, about 0.1 mg/kg to about 3 mg/kg, or about 0.1 mg/kg to 1.5 mg/kg. In still other embodiments of the invention, the dose may be as low as 0.1 mg/kg (0.02 mg/ml), about 0.2 mg/kg (0.04 mg/ml), about 0.3 mg/kg (0.06 mg/ml), about 0.4 mg/kg (0.08 mg/ml), about 0.5 mg/kg (0.1 mg/ml), about 0.6 mg/kg (0.12 mg/ml), about 0.7 mg/kg (0.14 mg/ml), about 0.8 mg/kg (0.16 mg/ml), about 0.9 mg/kg (0.18 mg/ml), about 1.0 mg/kg (0.2 mg/ml).

Agricultural Compositions

The compounds of formula (I) can be formulated in various ways, depending on the prevailing biological and/or chemico-physical parameters. Examples of possible formulations which are suitable are: wettable powders (WP), water-soluble powders (SP), water-soluble concentrates, emulsifiable concentrates (EC), emulsions (EW) such as oil-in-water and water-in-oil emulsions, sprayable solutions, suspension concentrates (SC), dispersions on an oil or water basis, solutions which are miscible with oil, capsule suspensions (CS), dusts (DP), seed-dressing products, granules for broadcasting and soil application, granules (GR) in the form of microgranules, spray granules, coated granules and adsorption granules, water-dispersible granules (WG), water-soluble granules (SG), ULV formulations, microcapsules and waxes.

Solid state forms of the compounds of formula (I) can be prepared by methods known in the art, e.g. Byrn et al., "Solid-State Chemistry of Drugs", $2^{nd}$ Edition, SSCI Inc., (1999); Glusker et al., "Crystal Structure Analysis—A Primer", $2^{nd}$ Edition, Oxford University Press, (1985).

The formulations mentioned can be prepared in a manner known per se, for example by mixing the active compounds with at least one solvent or diluent, emulsifier, dispersant and/or binder or fixative, water repellent and optionally one or more of a desiccant, UV stabilizer, a colorant, a pigment and other processing auxiliaries.

These individual formulation types are known in principle and described, for example, in: Winnacker-Küchler, "Chemische Technologie" [Chemical Technology], Volume 7, C. Hauser Verlag, Munich, 4th Edition 1986; Wade van Valkenburg, "Pesticide Formulations", Marcel Dekker, N.Y., 1973; K. Martens, "Spray Drying Handbook", 3rd Ed. 1979, G. Goodwin Ltd. London.

The necessary formulation auxiliaries such as inert materials, surfactants, solvents and other additives are also known and described, for example, in: Watkins, "Handbook of Insecticide Dust Diluents and Carriers", 2nd Ed., Darland Books, Caldwell N.J.; H.v. Olphen, "Introduction to Clay Colloid Chemistry", 2nd Ed., J. Wiley & Sons, N.Y.; C. Marsden, "Solvents Guide", 2nd Ed., Interscience, N.Y. 1963; McCutcheon's "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schönfeldt, "Grenzflächenaktive Äthylenoxidaddukte" [Surface-active ethylene oxide adducts], Wiss. Verlagsgesell, Stuttgart 1976; Winnacker-Küchler, "Chemische Technologie" [Chemical Technology], Volume 7, C. Hauser Verlag, Munich, 4th Ed. 1986.

Wettable powders are preparations which are uniformly dispersible in water and which, besides the compounds of formula (I), also comprise ionic and/or nonionic surfactants (wetters, dispersants), for example, polyoxyethylated alkylphenols, polyoxyethylated fatty alcohols, polyoxyethylated fatty amines, fatty alcohol polyglycol ether sulfates, alkanesulfonates or alkylbenzenesulfonates, sodium lignosulfonate, sodium 2,2'-dinaphthylmethane-6,6'-disulfonate, sodium dibutylnaphthalenesulfonate or else sodium oleoylmethyltaurinate, in addition to a diluent or inert substance. To prepare the wettable powders, the compounds of formula (I) are, for example, ground finely in conventional apparatuses such as hammer mills, blower mills and air-jet mills and mixed with the formulation auxiliaries, either concomitantly or thereafter.

Emulsifiable concentrates are prepared, for example, by dissolving the compounds of formula (I) in an organic solvent, for example butanol, cyclohexanone, dimethylformamide, xylene or else higher-boiling aromatics or hydrocarbons or mixtures of these, with addition of one or more ionic and/or nonionic surfactants (emulsifiers). Emulsifiers which can be used are, for example: calcium salts of alkylarylsulfonic acids, such as calcium dodecylbenzenesulfonate or nonionic emulsifiers, such as fatty acid polyglycol esters, alkylaryl polyglycol ethers, fatty alcohol polyglycol ethers, propylene oxide/ethylene oxide condensates, alkyl polyethers, sorbitan esters such as sorbitan fatty acid esters or polyoxyethylene sorbitan esters such as polyoxyethylene sorbitan fatty acid esters.

Dusts are obtained by grinding the active substance with finely divided solid substances, for example talc or natural clays, such as kaolin, bentonite or pyrophyllite, or diatomaceous earth.

Suspension concentrates may be water- or oil-based. They can be prepared, for example, by wet grinding by means of commercially available bead mills, if appropriate with addition of surfactants, as they have already been mentioned above for example in the case of the other formulation types.

Emulsions, for example oil-in-water emulsions (EW), can be prepared for example by means of stirrers, colloid mills and/or static mixtures using aqueous organic solvents and, if appropriate, surfactants as they have already been mentioned above for example in the case of the other formulation types.

Granules can be prepared either by spraying the compounds of formula (I) onto adsorptive, granulated inert material or by applying active substance concentrates onto the surface of carriers such as sand, kaolinites or of granulated inert material, by means of binders, for example polyvinyl alcohol, sodium polyacrylate or alternatively mineral oils. Suitable active substances can also be granulated in the manner which is conventional for the production of fertilizer granules, if desired in a mixture with fertilizers.

Water-dispersible granules are prepared, as a rule, by the customary processes such as spray-drying, fluidized-bed granulation, disk granulation, mixing in high-speed mixers and extrusion without solid inert material. To prepare disk, fluidized-bed, extruder and spray granules, see, for example, processes in "Spray-Drying Handbook" 3rd ed. 1979, G. Goodwin Ltd., London; J. E. Browning, "Agglomeration", Chemical and Engineering 1967, pages 147 et seq.; "Perry's Chemical Engineer's Handbook", 5th Ed., McGraw-Hill, New York 1973, p. 8-57. In general, the agrochemical preparations comprise a range selected from the group consisting of about 0.1 to about 99% by weight and about 0.1 to about 95% by weight, of compounds of formula (I).

The concentration of compounds of formula (I) in wettable powders is, for example, about 10 to about 90% by weight, the remainder to 100% by weight being composed of customary formulation components. In the case of emulsifiable concentrates, the concentration of compounds of formula (I) can amount to ranges selected from the group consisting of about 1% to about 90% and about 5% to about 80% by weight. Formulations in the form of dusts usually comprise in the range selected from the group consisting of about 1% to about 30% by weight of compounds of formula (I) and about 5% to about 20% by weight of compounds of formula (I). For sprayable solutions comprise a range selected from the group consisting of about 0.05% to about 80% by weight of compounds of formula (I) and about 2% to about 50% by weight of compounds of formula (I). In the case of water-dispersible granules, the content of compounds of formula (I) depends partly on whether the compounds of formula (I) are in liquid or solid form and on which granulation auxiliaries, fillers and the like are being used. The water-dispersible granules, for example, comprise a range selected from the group consisting of between about 1 and about 95% and between about 10% and about 80% by weight.

In addition, the formulations of compounds of formula (I) mentioned comprise, if appropriate, the adhesives, wetters, dispersants, emulsifiers, penetrants, preservatives, antifreeze agents, solvents, fillers, carriers, colorants, antifoams, evaporation inhibitors, pH regulators and viscosity regulators which are conventional in each case.

The following are examples of agricultural compositions:
1. Products for dilution with water. For seed treatment purposes, such products may be applied to the seed diluted or undiluted.

A) Water-Soluble Concentrates 10 parts by weight of the active compound is dissolved in 90 parts by weight of water or a water-soluble solvent. As an alternative, wetters or other auxiliaries are added. The active compound dissolves upon dilution with water, whereby a formulation with 10% (w/w) of active compound is obtained.

B) Dispersible Concentrates (DC)

20 parts by weight of the active compound is dissolved in 70 parts by weight of cyclohexanone with addition of 10 parts by weight of a dispersant, for example polyvinylpyrrolidone. Dilution with water gives a dispersion, whereby a formulation with 20% (w/w) of active compounds is obtained.

C) Emulsifiable Concentrates (EC)

15 parts by weight of the active compounds is dissolved in 7 parts by weight of xylene with addition of calcium dodecylbenzenesulfonate and castor oil ethoxylate (in each case 5 parts by weight). Dilution with water gives an emulsion, whereby a formulation with 15% (w/w) of active compounds is obtained.

D) Emulsions 25 parts by weight of the active compound is dissolved in 35 parts by weight of xylene with addition of calcium dodecylbenzenesulfonate and castor oil ethoxylate (in each case 5 parts by weight). This mixture is introduced into 30 parts by weight of water by means of an emulsifier machine (e.g. Ultraturrax) and made into a homogeneous emulsion. Dilution with water gives an emulsion, whereby a formulation with 25% (w/w) of active compound is obtained.

E) Suspensions

In an agitated ball mill, 20 parts by weight of the active compound is comminuted with addition of 10 parts by weight of dispersants, wetters and 70 parts by weight of water or of an organic solvent to give a fine active compound suspension. Dilution with water gives a stable suspension of the active compound, whereby a formulation with 20% (w/w) of active compound is obtained.

F) Water-Dispersible Granules and Water-Soluble Granules (WG, SG)

50 parts by weight of the active compound is ground finely with addition of 50 parts by weight of dispersants and wetters and made as water-dispersible or water-soluble granules by means of technical appliances (for example extrusion, spray tower, fluidized bed). Dilution with water gives a stable dispersion or solution of the active compound, whereby a formulation with 50% (w/w) of active compound is obtained.

G) Water-Dispersible Powders and Water-Soluble Powders 75 parts by weight of the active compound are ground in a rotor-stator mill with addition of 25 parts by weight of dispersants, wetters and silica gel. Dilution with water gives a stable dispersion or solution of the active compound, whereby a formulation with 75% (w/w) of active compound is obtained.

H) Gel-Formulation (GF)

In an agitated ball mill, 20 parts by weight of the active compound is comminuted with addition of 10 parts by weight of dispersants, 1 part by weight of a gelling agent wetters and 70 parts by weight of water or of an organic solvent to give a fine active compound suspension. Dilution with water gives a stable suspension of the active compound, whereby a formulation with 20% (w/w) of active compound is obtained.

2. Products to be applied undiluted for foliar applications. For seed treatment purposes, such products may be applied to the seed diluted or undiluted.

I) Dustable Powders 5 parts by weight of the active compound are ground finely and mixed intimately with 95 parts by weight of finely divided kaolin. This gives a dustable product having 5% (w/w) of active compound.

J) Granules 0.5 part by weight of the active compound is ground finely and associated with 95.5 parts by weight of carriers, whereby a formulation with 0.5% (w/w) of active compound is obtained. Current methods are extrusion, spray-drying or the fluidized bed. This gives granules to be applied undiluted for foliar use.

K) ULV Solutions (UL)

10 parts by weight of the active compound is dissolved in 90 parts by weight of an organic solvent, for example xylene. This gives a product having 10% (w/w) of active compound, which is applied undiluted for foliar use.

Methods of Treatment

In another embodiment, the invention provides a method for the treatment or prevention of a parasitic infestation or infection in an animal (e.g. a mammal or bird) comprising administering an effective amount of a dihydroazole compound of formula (I) or a composition comprising the compound to the animal. Mammals which can be treated include but are not limited to humans, cats, dogs, cattle, chickens, deer, goats, horses, llamas, pigs, sheep and yaks. In one embodiment of the invention, the mammals treated are humans, cats or dogs. In another embodiment, the animals treated are cattle, horses, sheep, goats or pigs.

In one embodiment, the invention provides a method for the treatment or prevention of an ectoparasitic infestation in an animal. In various embodiments, the ectoparasite is one or more insect or arachnid including those of the genera *Ctenocephalides, Rhipicephalus, Dermacentor, Ixodes, Boophilus, Ambylomma, Haemaphysalis, Hyalomma, Sarcoptes, Psoroptes, Otodectes, Chorioptes, Hypoderma, Damalinia, Linognathus, Haematopinus, Solenoptes, Trichodectes*, and *Felicola*.

In another embodiment for the treatment against ectoparasites, the ectoparasite is from the genera *Ctenocephalides, Rhipicephalus, Dermacentor, Ixodes* and/or *Boophilus*. The ectoparasites include but are not limited to fleas, ticks, mites, mosquitoes, flies, lice, blowfly and combinations thereof Specific examples include but are not limited to cat and dog fleas (*Ctenocephalides felis, Ctenocephalides* sp. and the like), ticks (*Rhipicephalus* sp., *Ixodes* sp., *Dermacentor* sp., *Amblyoma* sp. and the like), and mites (*Demodex* sp., *Sarcoptes* sp., *Otodectes* sp. and the like), lice (*Trichodectes* sp., *Cheyletiella* sp., *Lignonathus* sp., and the like), mosquitoes (*Aedes* sp., *Culex* sp., *Anopheles* sp., and the like) and flies (*Hematobia* sp., *Musca* sp., *Stomoxys* sp., *Dematobia* sp., *Cochliomyia* sp., and the like).

Additional examples of ectoparasites include but are not limited to the tick genus *Boophilus*, especially those of the species *microplus* (cattle tick), *decoloratus* and *annulatus*; myiases such as *Dermatobia hominis* (known as Berne in Brazil) and *Cochliomyia hominivorax* (greenbottle); sheep myiases such as *Lucilia sericata, Lucilia cuprina* (known as blowfly strike in Australia, New Zealand and South Africa). Flies proper, namely those whose adult constitutes the parasite, such as *Haematobia irritans* (horn fly); lice such as *Linognathus vitulorum*, etc.; and mites such as *Sarcoptes scabici* and *Psoroptes ovis*. The above list is not exhaustive and other ectoparasites are well known in the art to be harmful to animals and humans. These include, for example migrating dipterous larvae. In another embodiment, the invention provides a method for the treatment or prevention of an endoparasitic infection in an animal, comprising administering an effective amount of a dihydroazole compound of the invention to the animal. In some embodiments, the compounds of the invention may be used against endoparasites including *Anaplocephala, Ancylostoma, Anecator, Ascaris, Capillaria, Cooperia, Dipylidium, Dirofilaria, Echinococcus, Enterobius, Fasciola, Haemonchus, Oesophagostumum, Ostertagia, Toxocara, Strongyloides, Toxascaris, Trichinella, Trichuris*, and *Trichostrongylus*.

In a particularly preferred embodiment, the invention provides a method for the prevention and/or treatment of infections by *Dirofilaria immitis*, comprising administering to the animal a parasiticidally effective amount of a compound of formula (I). It has been surprisingly been found that the compounds of the invention are active against both ectoparasites and endoparasites that harm animals.

In another embodiment of the invention, the compounds and compositions of the invention are suitable for controlling pests at a locus. Therefore, an additional embodiment of the invention is a method for controlling pests at a locus, comprising applying a pesticidally effective amount of compound of formula (I) or a composition comprising the compound to the locus. Pests that may be controlled with the compounds of the invention include insects such as *Blatella germanica, Heliothis virescens, Leptinotarsa decemlineata, Tetramorium caespitum* and combinations thereof.

In still another embodiment, the compounds and compositions of the invention are effective for protecting crops, plants and material made from wood against pests. Thus, the invention provides a method for protecting crops, plants, plant propagation material and material made from wood from pests that harm these materials comprising applying the compounds of the invention or compositions comprising the compounds to the crops, plants, plant propagation material and material made from wood.

In other embodiments, the compounds and compositions of the invention may be used against the phytoparasitic nematodes including, for example, *Anguina* spp., *Aphelenchoides* spp., *Belonoaimus* spp., *Bursaphelenchus* spp., *Ditylenchus dipsaci, Globodera* spp., *Heliocotylenchus* spp., *Heterodera* spp., *Longidorus* spp., *Meloidogyne* spp., *Pratylenchus* spp., *Radopholus similis, Rotylenchus* spp., *Trichodorus* spp., *Tylenchorhynchus* spp., *Tylenchulus* spp., *Tylenchulus semipenetrans, Xiphinema* spp.

In addition, the compounds and compositions of the invention can also be used against pests which include, but are not limited to, the following pests:

(1) from the order of Isopoda, for example *Oniscus asellus, Armadillidium vulgare* and *Porcellio scaber;*

(2) from the order of Diplopoda, for example *Blaniulus guttulatus;*

(3) from the order of Chilopoda, for example *Geophilus carpophagus* and *Scutigera* spp.;

(4) from the order of Symphyla, for example *Scutigerella immaculata;*

(5) from the order of Thysanura, for example *Lepisma saccharina;*

(6) from the order of Collembola, for example *Onychiurus armatus;*

(7) from the order of Blattaria, for example *Blatta orientalis, Periplaneta americana, Leucophaea maderae* and *Blattella germanica;*

(8) from the order of Hymenoptera, for example *Diprion* spp., *Hoplocampa* spp., *Lasius* spp., *Monomorium pharaonis* and *Vespa* spp.;
(9) from the order of Siphonaptera, for example *Xenopsylla cheopis* and *Ceratophyllus* spp.;
(10) from the order of Anoplura (Phthiraptera), for example, *Damalinia* spp., *Haematopinus* spp., *Linognathus* spp., *Pediculus* spp., *Trichodectes* spp.;
(11) from the class of Arachnida, for example, *Acarus siro, Aceria sheldoni, Aculops* spp., *Aculus* spp., *Amblyomma* spp., *Argas* spp., *Boophilus* spp., *Brevipalpus* spp., *Bryobia praetiosa, Chorioptes* spp., *Dermanyssus gallinae, Eotetranychus* spp., *Epitrimerus pyri, Eutetranychus* spp., *Eriophyes* spp., *Hemitarsonemus* spp., *Hyalomma* spp., *Ixodes* spp., *Latrodectus mactans, Metatetranychus* spp., *Oligonychus* spp., *Ornithodoros* spp., *Panonychus* spp., *Phyllocoptruta oleivora, Polyphagotarsonemus latus, Psoroptes* spp., *Rhipicephalus* spp., *Rhizoglyphus* spp., *Sarcoptes* spp., *Scorpio maurus, Stenotarsonemus* spp., *Tarsonemus* spp., *Tetranychus* spp., *Vasates lycopersici;*
(12) from the class of Bivalva, for example, *Dreissena* spp.;
(13) from the order of Coleoptera, for example, *Acanthoscelides obtectus, Adoretus* spp., *Agelastica alni, Agriotes* spp., *Amphimallon solstitialis, Anobium punctatum, Anoplophora* spp., *Anthonomus* spp., *Anthrenus* spp., *Apogonia* spp., *Atomaria* spp., *Attagenus* spp., *Bruchidius obtectus, Bruchus* spp., *Ceuthorhynchus* spp., *Cleonus mendicus, Conoderus* spp., *Cosmopolites* spp., *Costelytra zealandica, Curculio* spp., *Cryptorhynchus lapathi, Dermestes* spp., *Diabrotica* spp., *Epilachna* spp., *Faustinus cubae, Gibbium psylloides, Heteronychus arator, Hylamorpha elegans, Hylotrupes bajulus, Hypera postica, Hypothenemus* spp., *Lachnosterna consanguinea, Leptinotarsa decemlineata, Lissorhoptrus oryzophilus, Lixus* spp., *Lyctus* spp., *Meligethes aeneus, Melolontha melolontha, Migdolus* spp., *Monochamus* spp., *Naupactus xanthographus, Niptus hololeucus, Oryctes rhinoceros, Oryzaephilus surinamensis, Otiorrhynchus sulcatus, Oxycetonia jucunda, Phaedon cochleariae, Phyllophaga* spp., *Popillia japonica, Premnotrypes* spp., *Psylliodes chrysocephala, Ptinus* spp., *Rhizobius ventralis, Rhizopertha dominica, Sitophilus* spp., *Sphenophorus* spp., *Sternechus* spp., *Symphyletes* spp., *Tenebrio molitor, Tribolium* spp., *Trogoderma* spp., *Tychius* spp., *Xylotrechus* spp., *Zabrus* spp.;
(14) from the order of Diptera, for example, *Aedes* spp., *Anopheles* spp., *Bibio hortulanus, Calliphora erythrocephala, Ceratitis capitata, Chrysomyia* spp., *Cochliomyia* spp., *Cordylobia anthropophaga, Culex* spp., *Cuterebra* spp., *Dacus oleae, Dermatobia hominis, Drosophila* spp., *Fannia* spp., *Gastrophilus* spp., *Hylemyia* spp., *Hyppobosca* spp., *Hypoderma* spp., *Liriomyza* spp., *Lucilia* spp., *Musca* spp., *Nezara* spp., *Oestrus* spp., *Oscinella frit, Pegomyia hyoscyami, Phorbia* spp., *Stomoxys* spp., *Tabanus* spp., *Tannia* spp., *Tipula paludosa, Wohlfahrtia* spp.;
(15) from the class of Gastropoda, for example, *Arion* spp., *Biomphalaria* spp., *Bulinus* spp., *Deroceras* spp., *Galba* spp., *Lymnaea* spp., *Oncomelania* spp., *Succinea* spp.;
(16) from the class of helminths, for example, *Ancylostoma duodenale, Ancylostoma ceylanicum, Acylostoma braziliensis, Ancylostoma* spp., *Ascaris lubricoides, Ascaris* spp., *Brugia malayi, Brugia timori, Bunostomum* spp., *Chabertia* spp., *Clonorchis* spp., *Cooperia* spp., *Dicrocoelium* spp, *Dictyocaulus filaria, Diphyllobothrium latum, Dracunculus medinensis, Echinococcus granulosus, Echinococcus multilocularis, Enterobius vermicularis, Faciola* spp., *Haemonchus* spp., *Heterakis* spp., *Hymenolepis nana, Hyostrongulus* spp., *Loa Loa, Nematodirus* spp., *Oesophagostomum* spp., *Opisthorchis* spp., *Onchocerca volvulus, Ostertagia* spp., *Paragonimus* spp., *Schistosomen* spp., *Strongyloides fuelleborni, Strongyloides stercoralis, Stronyloides* spp., *Taenia saginata, Taenia solium, Trichinella spiralis, Trichinella nativa, Trichinella britovi, Trichinella nelsoni, Trichinella pseudopsiralis, Trichostrongulus* spp., *Trichuris trichuria, Wuchereria bancrofti;*
(17) from the order of Heteroptera, for example, *Anasa tristis, Antestiopsis* spp., *Blissus* spp., *Calocoris* spp., *Campylomma livida, Cavelerius* spp., *Cimex* spp., *Creontiades dilutus, Dasynus piperis, Dichelops furcatus, Diconocoris hewetti, Dysdercus* spp., *Euschistus* spp., *Eurygaster* spp., *Heliopeltis* spp., *Horcias nobilellus, Leptocorisa* spp., *Leptoglossus phyllopus, Lygus* spp., *Macropes excavatus, Miridae, Nezara* spp., *Oebalus* spp., *Pentomidae, Piesma quadrata, Piezodorus* spp., *Psallus seriatus, Pseudacysta persea, Rhodnius* spp., *Sahlbergella singularis, Scotinophora* spp., *Stephanitis nashi, Tibraca* spp., *Triatoma* spp.;
(18) from the order of Homoptera, for example, *Acyrthosipon* spp., *Aeneolamia* spp., *Agonoscena* spp., *Aleurodes* spp., *Aleurolobus barodensis, Aleurothrixus* spp., *Amrasca* spp., *Anuraphis cardui, Aonidiella* spp., *Aphanostigma piri, Aphis* spp., *Arboridia apicalis, Aspidiella* spp., *Aspidiotus* spp., *Atanus* spp., *Aulacorthum solani, Bemisia* spp., *Brachycaudus helichrysii, Brachycolus* spp., *Brevicoryne brassicae, Calligypona marginata, Carneocephala fulgida, Ceratovacuna lanigera, Cercopidae, Ceroplastes* spp., *Chaetosiphon fragaefolii, Chionaspis tegalensis, Chlorita onukii, Chromaphis juglandicola, Chrysomphalus ficus, Cicadulina mbila, Coccomytilus halli, Coccus* spp., *Cryptomyzus ribis, Dalbulus* spp., *Dialeurodes* spp., *Diaphorina* spp., *Diaspis* spp., *Doralis* spp., *Drosicha* spp., *Dysaphis* spp., *Dysmicoccus* spp., *Empoasca* spp., *Eriosoma* spp., *Erythroneura* spp., *Euscelis bilobatus, Geococcus coffeae, Homalodisca coagulata, Hyalopterus arundinis, kerya* spp., *Idiocerus* spp., *Idioscopus* spp., *Laodelphax striatellus, Lecanium* spp., *Lepidosaphes* spp., *Lipaphis erysimi, Macrosiphum* spp., *Mahanarva fimbriolata, Melanaphis sacchari, Metcalfiella* spp., *Metopolophium dirhodum, Monellia costalis, Monelliopsis pecanis, Myzus* spp., *Nasonovia ribisnigri, Nephotettix* spp., *Nilaparvata lugens, Oncometopia* spp., *Orthezia praelonga, Parabemisia myricae, Paratrioza* spp., *Parlatoria* spp., *Pemphigus* spp., *Peregrinus maidis, Phenacoccus* spp., *Phloeomyzus passerinii, Phorodon humuli, Phylloxera* spp., *Pinnaspis aspidistrae, Planococcus* spp., *Protopulvinaria pyriformis, Pseudaulacaspis pentagona, Pseudococcus* spp., *Psylla* spp., *Pteromalus* spp., *Pyrilla* spp., *Quadraspidiotus* spp., *Quesada gigas, Rastrococcus* spp., *Rhopalosiphum* spp., *Saissetia* spp., *Scaphoides titanus, Schizaphis graminum, Selenaspidus articulatus, Sogata* spp., *Sogatella furcifera, Sogatodes* spp., *Stictocephala festina, Tenalaphara malayensis, Tinocallis caryaefoliae, Tomaspis* spp., *Toxoptera* spp., *Trialeurodes vaporariorum, Trioza* spp., *Typhlocyba* spp., *Unaspis* spp., *Viteus vitifolii;*
(19) from the order of Isoptera, for example, *Reticulitermes* spp., *Odontotermes* spp.;
(20) from the order of Lepidoptera, for example, *Acronicta major, Aedia leucomelas, Agrotis* spp., *Alabama argillacea, Anticarsia* spp., *Barathra brassicae, Bucculatrix thurberiella, Bupalus piniarius, Cacoecia podana, Capua*

*reticulana, Carpocapsa pomonella, Cheimatobia brumata, Chilo* spp., *Choristoneura fumiferana, Clysia ambiguella, Cnaphalocerus* spp., *Earias insulana, Ephestia kuehniella, Euproctis chrysorrhoea, Euxoa* spp., *Feltia* spp., *Galleria mellonella, Helicoverpa* spp., *Heliothis* spp., *Hofmannophila pseudospretella, Homona magnanima, Hyponomeuta padella, Laphygma* spp., *Lithocolletis blancardella, Lithophane antennata, Loxagrotis albicosta, Lymantria* spp., *Malacosoma neustria, Mamestra brassicae, Mods repanda, Mythimna separata, Oria* spp., *Oulema oryzae, Panolis flammea, Pectinophora gossypiella, Phyllocnistis citrella, Pieris* spp., *Plutella xylostella, Prodenia* spp., *Pseudaletia* spp., *Pseudoplusia includens, Pyrausta nubilalis, Spodoptera* spp., *Thermesia gemmatalis, Tinea pellionella, Tineola bisselliella, Tortrix viridana, Trichoplusia* spp.;

(21) from the order of Orthoptera, for example, *Acheta domesticus, Blatta orientalis, Blattella germanica, Gryllotalpa* spp., *Leucophaea maderae, Locusta* spp., *Melanoplus* spp., *Periplaneta americana, Schistocerca gregaria;*

(22) from the order of Thysanoptera, for example, *Baliothrips biformis, Enneothrips flavens, Frankliniella* spp., *Heliothrips* spp., *Hercinothrips femoralis, Kakothrips* spp., *Rhipiphorothrips cruentatus, Scirtothrips* spp., *Taeniothrips cardamoni, Thrips* spp.;

(23) from the class of Protozoa, for example, *Eimeria* spp.

Active Agent Combinations

The compounds of formula (I) or their salts can be employed as such or in the form of their preparations (formulations) as combinations with other active substances. For agricultural uses, the compounds of formula (I) may be used in combination with, for example, insecticides, attractants, sterilants, acaricides, nematicides, herbicides, fungicides, and with safeners, fertilizers and/or growth regulators, for example as a premix/readymix.

Classifications of fungicides are well-known in the art and include classifications by FRAC (Fungicide Resistance Action Committee). Fungicides which may optionally be admixed with the compounds of formula (I) include, but are not limited to, methyl benzimidazole carbamates, such as benzimidazoles and thiophanates; dicarboximides; demethylation inhibitors, such as imidazoles, piperazines, pyridines, pyrimidines, and triazoles; phenylamides, such as acylalanines, oxazolidinones, and butyrolactones; amines, such as morpholines, piperidines, and spiroketalamines; phosphorothiolates; dithiolanes; carboxamides; hydroxy-(2-amino-)pyrimidines; anilino-pyrimidines; N-phenyl carbamates; quinone outside inhibitors; phenylpyrroles; quinolines; aromatic hydrocarbons; heteroaromatics; melanin biosynthesis inhibitors-reductase; melanin biosynthesis inhibitors-dehydratase; hydroxyanilides (SBI class III), such as fenhexamid; SBI class IV, such as thiocarbamates and allylamines; polyoxins; phenylureas; quinone inside inhibitors; benzamides; enopyranuronic acid antibiotic; hexopyranosyl antibiotic; glucopyranosyl antibiotic; glucopyranosyl antibiotic; cyanoacetamideoximes; carbamates; uncoupler of oxidative phosphorylation; organo tin compounds; carboxylic acids; heteroaromatics; phosphonates; phthalamic acids; benzotriazines; benzenesulfonamides; pyridazinones; carboxylic acid amides; tetracycline antibiotic; thiocarbamate; benzo-thiadiazole BTH; benzisothiazole; thiadiazolecarboxamide; thiazolecarboxamides; benzamidoxime; quinazolinone; benzophenone; acylpicolide; inorganic compounds, such as copper salts and sulphur; dithiocarbamates and relatives; phthalimides; chloronitriles; sulphamides; guanidines; triazines; quinones.

Other fungicides that may optionally be admixed with the compounds of formula (I) may also be from the classes of compounds described in U.S. Pat. Nos. 7,001,903 and 7,420,062, each incorporated herein by reference.

Herbicides that are known from the literature and classified by HRAC (Herbicide Resistance Action Committee) and may be combined with the compounds of the invention are, for example: aryloxyphenoxy-propionate; cyclohexanedione; phenylpyrazoline; sulfonylurea; imidazolinone, such as imazapic and imazethapyr; triazolopyrimidine; pyrimidinyl(thio)benzoate; sulfonylaminocarbonyl-triazolinone; triazine, such as atrazine; triazinone; triazolinone; uracil; pyridazinone; phenyl-carbamate; urea; amide; nitrile; benzothiadiazinone; phenyl-pyridazine; bipyridylium, such as paraquat; diphenylether; phenylpyrazole; N-phenylphthalimide; thiadiazole; thiadiazole; triazolinone; oxazolidinedione; pyrimidindione; pyridazinone; pyridinecarboxamide; triketone; isoxazole; pyrazole; triazole; isoxazolidinone; urea, such as linuron; diphenylether; glycine, such as glyphosate; phosphinic acid, such as glufosinate-ammonium; carbamate; dinitroaniline, such as pendimethalin; phosphoroamidate; pyridine; benzamide; benzoic acid; chloroacetamide; metolachlor; acetamide; oxyacetamide; tetrazolinone; nitrile; benzamide; triazolocarboxamide; quinoline carboxylic acid; dinitrophenol; thiocarbamate; phosphorodithioate; benzofuran; chloro-carbonic-acid; phenoxy-carboxylic-acid, such as 2,4-D; benzoic acid, such as dicamba; pyridine carboxylic acid, such as clopyralid, triclopyr, fluroxypyr and picloram; quinoline carboxylic acid; phthalamate semicarbazone; qrylaminopropionic acid; qrylaminopropionic acid; organoarsenical.

Other herbicides that may optionally be admixed are compounds described in U.S. Pat. Nos. 7,432,226, 7,012,041, and 7,365,082, all incorporated herein by reference.

Appropriate herbicide safeners include but are not limited to benoxacor, cloquintocet, cyometrinil, cyprosulfamide, dichlormid, dicyclonon, dietholate, fenchlorazole, fenclorim, flurazole, fluxofenim, furilazole, isoxadifen, mefenpyr, mephenate, naphthalic anyhydride and oxabetrinil.

Bactericides include, but are not limited to, bronopol, dichlorophen, nitrapyrin, nickel dimethyldithiocarbamate, kasugamycin, octhilinone, furancarboxylic acid, oxytetracycline, probenazole, streptomycin, tecloftalam, copper sulphate and other copper preparations.

Insecticides/acaricides/nematicides include those compounds mentioned in U.S. Pat. Nos. 7,420,062 and 7,001,903, U.S. Patent publication 2008/0234331, each incorporated herein by referenceand the compounds classified by IRAC (Insecticide Resistance Action Committee). Examples of insecticides/acaricides/nematicides include, but are limited to, carbamates; triazemate; organophosphates; cyclodiene organochlorines; phenylpyrazoles; DDT; methoxychlor; pyrethroids; pyrethrins; neonicotinoids; nicotine; bensultap; cartap hydrochloride; nereistoxin analogues; spinosyns; avermectins and milbemycins; juvenile hormone analogues; fenoxycarb; fenoxycarb; alkyl halides; chloropicrin; sulfuryl fluoride; cryolite; pymetrozine; flonicamid; clofentezine; hexythiazox; etoxazole; *Bacillus sphaericus*; diafenthiuron; organotin miticides; propargite; tetradifon; chlorfenapyr; DNOC; benzoylureas; buprofezin; cyromazine; diacylhydrazines; azadirachtin; amitraz; hydramethylnon; acequinocyl; fluacrypyrim; METI acaricides; rotenone; indoxacarb; metaflumizone; tetronic acid derivatives; aluminium phosphide; cyanide; phosphine; bifenazate; fluoroacetate; P450-dependent monooxygenase inhibitors; esterase inhibitors;

diamides; benzoximate; chinomethionat; dicofol; pyridalyl; borax; tartar emetic; fumigants, such as methyl bromide; ditera; clandosan; sincocin.

Veterinary compositions may include a compound of formula (I) in combination with additional pharmaceutically or veterinarily active agents. In some embodiments, the additional active agents may be one or more parasiticidal compounds including acaricides, anthelmintics, endectocides and insecticides. Anti-parasitic agents can include both ectoparasitici sal and endop ara siti ci dal agents.

Veterinary pharmaceutical agents that may be included in the compositions of the invention are well-known in the art (see e.g. *Plumb' Veterinary Drug Handbook*, 5$^{th}$ Edition, ed. Donald C. Plumb, Blackwell Publishing, (2005) or *The Merck Veterinary Manual*, 9$^{th}$ Edition, (January 2005)) and include but are not limited to acarbose, acepromazine maleate, acetaminophen, acetazolamide, acetazolamide sodium, acetic acid, acetohydroxamic acid, acetylcysteine, acitretin, acyclovir, albendazole, albuterol sulfate, alfentanil, allopurinol, alprazolam, altrenogest, amantadine, amikacin sulfate, aminocaproic acid, aminopentamide hydrogen sulfate, aminophylline/theophylline, amiodarone, amitraz, amitriptyline, amlodipine besylate, ammonium chloride, ammonium molybdenate, amoxicillin, clavulanate potassium, amphotericin B desoxycholate, amphotericin B lipid-based, ampicillin, amprolium, antacids (oral), antivenin, apomorphione, apramycin sulfate, ascorbic acid, asparaginase, aspiring, atenolol, atipamezole, atracurium besylate, atropine sulfate, aurnofin, aurothioglucose, azaperone, azathioprine, azithromycin, baclofen, barbituates, benazepril, betamethasone, bethanechol chloride, bisacodyl, bismuth subsalicylate, bleomycin sulfate, boldenone undecylenate, bromides, bromocriptine mesylate, budenoside, buprenorphine, buspirone, busulfan, butorphanol tartrate, cabergoline, calcitonin salmon, calcitrol, calcium salts, captopril, carbenicillin indanyl sodium, carbimazole, carboplatin, carnitine, carprofen, carvedilol, cefadroxil, cefazolin sodium, cefixime, chlorsulon, cefoperazone sodium, cefotaxime sodium, cefotetan disodium, cefoxitin sodium, cefpodoxime proxetil, ceftazidime, ceftiofur sodium, ceftiofur, ceftiaxone sodium, cephalexin, cephalosporins, cephapirin, charcoal (activated), chlorambucil, chloramphenicol, chlordiazepoxide, chlordiazepoxide +/- clidinium bromide, chlorothiazide, chlorpheniramine maleate, chlorpromazine, chlorpropamide, chlortetracycline, chorionic gonadotropin (HCG), chromium, cimetidine, ciprofloxacin, cisapride, cisplatin, citrate salts, clarithromycin, clemastine fumarate, clenbuterol, clindamycin, clofazimine, clomipramine, claonazepam, clonidine, cloprostenol sodium, clorazepate dipotassium, clorsulon, cloxacillin, codeine phosphate, colchicine, corticotropin (ACTH), cosyntropin, cyclophosphamide, cyclosporine, cyproheptadine, cytarabine, dacarbazine, dactinomycin/actinomycin D, dalteparin sodium, danazol, dantrolene sodium, dapsone, decoquinate, deferoxamine mesylate, deracoxib, deslorelin acetate, desmopressin acetate, desoxycorticosterone pivalate, detomidine, dexamethasone, dexpanthenol, dexraazoxane, dextran, diazepam, diazoxide (oral), dichlorphenamide, diclofenac sodium, dicloxacillin, diethylcarbamazine citrate, diethylstilbestrol (DES), difloxacin, digoxin, dihydrotachysterol (DHT), diltiazem, dimenhydrinate, dimercaprol/BAL, dimethyl sulfoxide, dinoprost tromethamine, diphenylhydramine, disopyramide phosphate, dobutamine, docusate/DSS, dolasetron mesylate, domperidone, dopamine, doramectin, doxapram, doxepin, doxorubicin, doxycycline, edetate calcium disodium.calcium EDTA, edrophonium chloride, enalapril/enalaprilat, enoxaparin sodium, enrofloxacin, ephedrine sulfate, epinephrine, epoetin/erythropoietin, eprinomectin, epsiprantel, erythromycin, esmolol, estradiol cypionate, ethacrynic acid/ethacrynate sodium, ethanol (alcohol), etidronate sodium, etodolac, etomidate, euthanasia agents w/pentobarbital, famotidine, fatty acids (essential/omega), felbamate, fentanyl, ferrous sulfate, filgrastim, finasteride, fipronil, florfenicol, fluconazole, flucytosine, fludrocortisone acetate, flumazenil, flumethasone, flunixin meglumine, fluorouracil (5-FU), fluoxetine, fluticasone propionate, fluvoxamine maleate, fomepizole (4-MP), furazolidone, furosemide, gabapentin, gemcitabine, gentamicin sulfate, glimepiride, glipizide, glucagon, glucocorticoid agents, glucosamine/chondroitin sulfate, glutamine, glyburide, glycerine (oral), glycopyrrolate, gonadorelin, grisseofulvin, guaifenesin, halothane, hemoglobin glutamer-200 (oxyglobing), heparin, hetastarch, hyaluronate sodium, hydrazaline, hydrochlorothiazide, hydrocodone bitartrate, hydrocortisone, hydromorphone, hydroxyurea, hydroxyzine, ifosfamide, imidacloprid, imidocarb dipropinate, impenem-cilastatin sodium, imipramine, inamrinone lactate, insulin, interferon alfa-2a (human recombinant), iodide (sodium/potassium), ipecac (syrup), ipodate sodium, iron dextran, isoflurane, isoproterenol, isotretinoin, isoxsuprine, itraconazole, ivermectin, kaolin/pectin, ketamine, ketoconazole, ketoprofen, ketorolac tromethamine, lactulose, leuprolide, levamisole, levetiracetam, levothyroxine sodium, lidocaine, lincomycin, liothyronine sodium, lisinopril, lomustine (CCNU), lufenuron, lysine, magnesium, mannitol, marbofloxacin, mechlorethamine, meclizine, meclofenamic acid, medetomidine, medium chain triglycerides, medroxyprogesterone acetate, megestrol acetate, melarsomine, melatonin, meloxican, melphalan, meperidine, mercaptopurine, meropenem, metformin, methadone, methazolamide, methenamine mandelate/hippurate, methimazole, methionine, methocarbamol, methohexital sodium, methotrexate, methoxyflurane, methylene blue, methylphenidate, methylprednisolone, metoclopramide, metoprolol, metronidaxole, mexiletine, mibolerlone, midazolam milbemycin oxime, mineral oil, minocycline, misoprostol, mitotane, mitoxantrone, morphine sulfate, moxidectin, naloxone, mandrolone decanoate, naproxen, narcotic (opiate) agonist analgesics, neomycin sulfate, neostigmine, niacinamide, nitazoxanide, nitenpyram, nitrofurantoin, nitroglycerin, nitroprusside sodium, nizatidine, novobiocin sodium, nystatin, octreotide acetate, olsalazine sodium, omeprozole, ondansetron, opiate antidiarrheals, orbifloxacin, oxacillin sodium, oxazepam, oxibutynin chloride, oxymorphone, oxytretracycline, oxytocin, pamidronate disodium, pancreplipase, pancuronium bromide, paromomycin sulfate, parozetine, pencillamine, general information penicillins, penicillin G, penicillin V potassium, pentazocine, pentobarbital sodium, pentosan polysulfate sodium, pentoxifylline, pergolide mesylate, phenobarbital, phenoxybenzamine, pheylbutazone, phenylephrine, phenypropanolamine, phenytoin sodium, pheromones, parenteral phosphate, phytonadione/vitamin K-1, pimobendan, piperazine, pirlimycin, piroxicam, polysulfated glycosaminoglycan, ponazuril, potassium chloride, pralidoxime chloride, prazosin, prednisolone/prednisone, primidone, procainamide, procarbazine, prochlorperazine, propantheline bromide, propionibacterium acnes injection, propofol, propranolol, protamine sulfate, pseudoephedrine, psyllium hydrophilic mucilloid, pyridostigmine bromide, pyrilamine maleate, pyrimethamine, quinacrine, quinidine, ranitidine, rifampin, s-adenosyl-methionine (SAMe), saline/hyperosmotic laxative, selamectin, selegiline/1-deprenyl, sertraline, sevelamer, sevoflurane, silymarin/milk thistle, sodium bicarbonate, sodium polystyrene sulfonate, sodium stibogluconate, sodium sulfate, sodum thiosulfate, somatotropin, sotalol, spectinomycin, spironolactone, stanozolol, streptokinase, streptozocin, succimer, succinylcholine chloride, sucralfate, sufentanil citrate, sulfachlorpyridazine sodium, sulfadiazine/trimethroprim, sulfamethoxazole/trimethoprim, sulfadimentoxine, sulfadimethoxine/ormetoprim, sulfasalazine, taurine, tepoxaline, terbinafline, terbutaline sulfate, testosterone, tetracycline, thiacetarsamide sodium, thiamine, thioguanine, thiopental sodium, thiotepa, thyrotropin, tiamulin, ticarcilin disodium, tiletamine/zolazepam, tilmocsin, tiopronin, tobramycin sulfate, tocainide, tolazoline, telfenamic acid, topiramate, tramadol, trimcinolone acetonide, trientine, trilostane, trimepraxine tartrate w/prednisolone, tripelennamine, tylosin, urdosiol, valproic acid, vanadium, vancomycin, vasopressin, vecuronium bromide, verapamil, vinblastine sulfate, vincristine sulfate, vitamin E/selenium, warfarin sodium, xylazine, yohimbine, zafirlukast, zidovudine (AZT), zinc acetate/zinc sulfate, zonisamide and mixtures thereof.

In one embodiment of the invention, arylpyrazole compounds such as phenylpyrazoles (e.g. fipronil, pyriprole), may be suitable for combination with the dihydroazole compounds of the invention. Examples of such arylpyrazole compounds include but are not limited to those described in U.S. Pat. Nos. 6,001,384; 6,010,710; 6,083,519; 6,096,329; 6,174,540; 6,685,954 and 6,998,131, all incorporated herein by reference, each assigned to Merial, Ltd., Duluth, Ga.

In another embodiment of the invention, nodulisporic acid and its derivatives (a class of known acaricidal, anthelminitic, anti-parasitic and insecticidal agents) can be added to the compositions of the invention. These compounds are used to treat or prevent infections in humans and animals and are described, for example, in U.S. Pat. Nos. 5,399,582, 5,962,499, 6,221,894 and 6,399,786, all incorporated herein by reference.

In another embodiment, anthelmintic compounds of the amino acetonitrile class (AAD) of compounds such as monepantel (ZOLVIX) and the like may be added to the compositions of the invention. These compounds are described, for example, in WO 2004/024704; Sager et al., Veterinary Parasitology, 2009, 159, 49-54; Kaminsky et al., Nature vol. 452, 13 Mar. 2008, 176-181.

In another embodiment, the compositions of the invention may advantageously include one or more isoxazoline compounds having different structures than the compounds of the invention. Various active agents having an isoxazoline ring system are described in WO 2007/079162, WO 2007/075459 and US 2009/0133319, WO 2007/070606 and US 2009/0143410, WO 2009/003075, WO 2009/002809, WO 2009/024541, WO 2005/085216 and US 2007/0066617 and WO 2008/122375, all of which are incorporated herein by reference in their entirety.

The compositions of the invention may also be combined with paraherquamide compounds and derivatives of these compounds, including derquantel (see Ostlind et al., *Research in Veterinary Science*, 1990, 48, 260-61; and Ostlind et al., *Medical and Veterinary Entomology*, 1997, 11,407-408). The paraherquamide family of compounds are known class of compounds that include a spirodioxepino indole core with activity against certain parasites (see *Tet. Lett.* 1981, 22, 135; *J. Antibiotics* 1990, 43, 1380, and *J. Antibiotics* 1991, 44, 492). In addition, the structurally related marcfortine family of compounds, such as marcfortines A-C, are also known and may be combined with the formulations of the invention (see *J. Chem. Soc.-Chem. Comm.* 1980, 601 and *Tet. Lett.* 1981, 22, 1977). Further references to the paraherquamide derivatives can be found, for example, in WO 91/09961, WO 92/22555, WO 97/03988, WO 01/076370, WO 09/004432, U.S. Pat. No. 5,703,078 and U.S. Pat. No. 5,750,695, all of which are hereby incorporated by reference in their entirety.

In another embodiment, the compositions of the invention may be combined with cyclo-depsipeptide anthelmintic compounds including emodepside (see Willson et al., *Parasitology*, January 2003, 126(Pt 1):79-86).

In some embodiments, the compositions of the invention may include one or more antinematodal agents including, but not limited to, active agents in the benzimidazole class of compounds, the imidazothiazole class, the tetrahydropyrimidine class, or the organophosphate class of compounds. In some embodiments, benzimidazoles including, but not limited to, thiabendazole, cambendazole, parbendazole, oxibendazole, mebendazole, flubendazole, fenbendazole, oxfendazole, albendazole, cyclobendazole, febantel, thiophanate and its o,o-dimethyl analogue may be included in the compositions.

In other embodiments, the compositions may include an imidazothiazole compounds including, but not limited to, tetramisole, levamisole and butamisole. In still other embodiments, the compositions of the invention may include tetrahydropyrimidine active agents including, but not limited to, pyrantel, oxantel, and morantel. Suitable organophosphate active agents include, but are not limited to, coumaphos, trichlorfon, haloxon, naftalofos and dichlorvos.

In other embodiments, the compositions may include the antinematodal compounds phenothiazine, piperazine as the neutral compound and in various salt forms, diethylcarbamazine, phenols such as disophenol, arsenicals such as arsenamide, ethanolamines such as bephenium, thenium closylate, and methyridine; cyanine dyes including pyrvinium chloride, pyrvinium pamoate and dithiazanine iodide; isothiocyanates including bitoscanate, suramin sodium, phthalofyne, and various natural products including, but not limited to, hygromycin B, α-santonin and kainic acid.

In other embodiments, the compositions of the invention may include antitrematodal agents. Suitable antitrematodal agents include, but are not limited to, the miracils such as miracil D and mirasan; praziquantel, clonazepam and its 3-methyl derivative, oltipraz, lucanthone, hycanthone, oxamniquine, amoscanate, niridazole, nitroxynil, various bisphenol compounds known in the art including hexachlorophene, bithionol, bithionol sulfoxide and menichlopholan; various salicylanilide compounds including tribromsalan, oxyclozanide, clioxanide, rafoxanide, brotianide, bromoxanide and closantel; triclabendazole, diamfenetide, clorsulon, hetolin and emetine.

Anticestodal compounds may also be advantageously used in the compositions of the invention including, but not limited to, arecoline in various salt forms, bunamidine, niclosamide, nitroscanate, paromomycin and paromomycin II.

In yet other embodiments, the compositions of the invention may include other active agents that are effective against artropod parasites. Suitable active agents include, but are not limited to, bromocyclen, chlordane, DDT, endosulfan, lindane, methoxychlor, toxaphene, bromophos, bromophosethyl, carbophenothion, chlorfenvinphos, chlorpyrifos, crotoxyphos, cythioate, diazinon, dichlorenthion diemthoate, dioxathion, ethion, famphur, fenitrothion, fenthion, fospirate, iodofenphos, malathion, naled, phosalone, phosmet, phoxim, propetamphos, ronnel, stirofos, carbaryl, promacyl, propoxur, allethrin, cyhalothrin, cypermethrin, deltamethrin, fenvalerate, flucythrinate, permethrin, phenothrin, pyrethrins, resmethrin, amitraz, benzyl benzoate, carbon disulfide, crotamiton, diflubenzuron, diphenylamine, disulfiram, isobornyl thiocyanato acetate, methoprene, monosulfiram, pirenonylbutoxide, rotenone, triphenyltin acetate, triphenyltin hydroxide, deet, dimethyl phthalate, and the compounds 1,5a,6,9,9a,9b-hexahydro-4a(4H)-dibenzofurancarboxaldehyde (MGK-11), 2-(2-ethylhexyl)-3a,4,7,7a-tetrahydro-4,7-methano-1H-isoindole-1,3(2H)dione (MGK-264), dipropyl-2,5-pyridinedicarboxylate (MGK-326) and 2-(octylthio) ethanol (MGK-874).

In another embodiment of the invention, one or more macrocyclic lactones, which act as an acaricide, anthelmintic agent and insecticide, can be added to the compositions of the invention. The macrocyclic lactones also include, but are not limited to, avermectins, such as abamectin, dimadectin, doramectin, emamectin, eprinomectin, ivermectin, latidectin, lepimectin, selamectin, and milbemycins, such as milbemectin, milbemycin D, moxidectin and nemadectin. Also included are the 5-oxo and 5-oxime derivatives of said avermectins and milbemycins. Examples of combinations of macrocyclic lactones with other active agents are described in U.S. Pat. Nos. 6,426,333; 6,482,425; 6,962,713 and 6,998,131—each assigned to Merial, Ltd., Duluth, Ga., all incorporated herein by reference.

The macrocyclic lactone compounds are known in the art and can be obtained commercially or through synthesis techniques known in the art. Reference is made to the widely available technical and commercial literature. For avermectins, ivermectin and abamectin, reference may be made, for example, to the work "Ivermectin and Abamectin", 1989, by M. H. Fischer and H. Mrozik, William C. Campbell, published by Springer Verlag., "Macrocyclic Lactones in Antiparasitic Therapy", 2002, by J Vercruysse and R S Rew published by CABI Publishing or Albers-Schönberg et al. (1981), "Avermectins Structure Determination", J. Am. Chem. Soc., 103, 4216-4221. For doramectin, "Veterinary Parasitology", vol. 49, No. 1, July 1993, 5-15 may be consulted. For milbemycins, reference may be made, inter al/a, to Davies H. G. et al., 1986, "Avermectins and Milbemycins", Nat. Prod. Rep., 3, 87-121, Mrozik H. et al., 1983, Synthesis of Milbemycins from Avermectins, Tetrahedron Lett., 24, 5333-5336, U.S. Pat. No. 4,134,973 and EP 0 677 054.

Macrocyclic lactones are either natural products or are semi-synthetic derivatives thereof. The structures of the avermectins and milbemycins are closely related, e.g., by sharing a complex 16-membered macrocyclic lactone ring; milbemycins lack the glycosidic moiety of the avermectins. The natural products avermectins are disclosed in U.S. Pat. No. 4,310,519 to Albers-Schönberg et al., and the 22,23-dihydro avermectin compounds are disclosed in Chabala et al., U.S. Pat. No. 4,199,569. Mention is also made of Kitano, U.S. Pat. No. 4,468,390, Beuvry et al., U.S. Pat. No. 5,824,653, EP 0 007 812 A1, U.K. Patent Specification 1 390 336, EP 0 002 916, and Ancare New Zealand Patent No. 237 086, inter alia. Naturally occurring milbemycins are described in Aoki et al., U.S. Pat. No. 3,950,360 as well as in the various references cited in "The Merck Index" 12$^{th}$ ed., S. Budavari, Ed., Merck & Co., Inc. Whitehouse Station, New Jersey (1996). Latidectin is described in the "International Nonproprietary Names for Pharmaceutical Substances (INN)", WHO Drug Information, vol. 17, no. 4, pp. 263-286, (2003). Semisynthetic derivatives of these classes of compounds are well known in the art and are described, for example, in U.S. Pat. Nos. 5,077,308, 4,859,657, 4,963,582, 4,855,317, 4,871,719, 4,874,749, 4,427,663, 4,310,519, 4,199,569, 5,055,596, 4,973,711, 4,978,677, 4,920,148 and EP 0 667 054.

In another embodiment of the invention, the class of acaricides or insecticides known as insect growth regulators (IGRs) can also be added to the compositions of the invention. Compounds belonging to this group are well known to the practitioner and represent a wide range of different chemical classes. These compounds all act by interfering with the development or growth of the insect pests. Insect growth regulators are described, for example, in U.S. Pat. Nos. 3,748,356; 3,818,047; 4,225,598; 4,798,837; 4,751,225, EP 0 179 022 or U.K. 2 140 010 as well as U.S. Pat. Nos. 6,096,329 and 6,685,954 (all incorporated herein by reference). Examples of IGRs suitable for use include but are not limited to methoprene, pyriproxyfen, hydroprene, cyromazine, fluazuron, lufenuron, novaluron, pyrethroids, formamidines and 1-(2,6-difluorobenzoyl)-3-(2-fluoro-4-(trifluoromethyl)phenylurea.

An insecticidal agent that can be combined with the compound of the invention to form a composition can be a spinosyn (e.g. spinosad) or a substituted pyridylmethyl derivative compound such as imidacloprid. Agents of this class are described above, and for example, in U.S. Pat. No. 4,742,060 or in EP 0 892 060, both incorporated herein by reference. It would be well within the skill level of the practitioner to decide which individual compound can be used in the inventive formulation to treat a particular parasitic infection/infestation. For ectoparasites, active agents that can be combined also include but are not limited to pyrethoids, organophosphates and neonicotinoids such as imidacloprid, as well as compounds such as metaflumizone, amitraz and ryanodine receptor antagonists.

Where appropriate the anthelmintic, parasiticidal and insecticial agent may also be selected from the group of compounds described above as suitable for agrochemical use.

In general, the additional active agent is included in a dose of between about 0.1 µg and about 1000 mg. More typically, the additional active agent may be included in a dose of about 10 µg to about 500 mg, about 1 mg to about 300 mg, about 10 mg to about 200 mg or about 10 mg to about 100 mg. In one embodiment of the invention, the additional active agent is included in a dose of between about 1 µg and about 10 mg.

In other embodiments of the invention, the additional active agent may be included in a dose of about 5 µg/kg to about 50 mg/kg per weight of the animal. In other embodiments, the additional active agent may be present in a dose of about 0.01 mg/kg to about 30 mg/kg, about 0.1 mg/kg to about 20 mg/kg, or about 0.1 mg/kg to about 10 mg/kg of weight of animal. In other embodiments, the additional active agent may be present in a dose of about 5 µg/kg to about 200 µg/kg or about 0.1 mg/kg to about 1 mg/kg of weight of animal. In still another embodiment of the invention, the additional active agent is included in a dose between about 0.5 mg/kg to about 50 mg/kg.

The proportions, by weight, of the dihydroazole compound and the additional active agent are for example between about 5/1 and about 10,000/1. However, one of ordinary skill in the art would be able to select the appropriate ratio of dihydroazole compound and the additional active agent for the intended host and use thereof.

Another aspect of the invention is the process of making the dihydroazole compounds of the invention.

The compounds of formula (I) may be prepared according to the processes described herein or by the application or adaptation of known methods (i.e. methods heretofore used or described in the chemical literature).

The invention will now be further described by way of the following non-limiting examples.

EXAMPLES

All temperatures are given in degrees Centigrade; room temperature means 20 to 25° C. Reagents were purchased from commercial sources or prepared following literature procedures.
DCM=dichloromethane
THF=tetrahydrofuran
MeOH=methanol
EtOH=ethanol
EA=ethyl acetate
DMF=dimethylformamide
DMA=dimethyl acetamide
DMFDMA=dimethylformamide dimethyl acetal
AcOH=acetic acid
TFA=trifluoroacetic acid
TEA=triethylamine
DIEA=diisopropylethylamine Proton and fluorine magnetic resonance (respectively $^1$H NMR and $^{19}$F NMR) spectra were recorded on a Varian INOVA NMR spectrometer [400 MHz (1H) or 500 MHz ($^1$H) and 377 MHz ($^{19}$F)]. All spectra were determined in the solvents indicated. Chemical shifts are reported in ppm downfield of tetramethylsilane (TMS), referenced to the residual proton peak of the respective solvent peak for $^1$H NMR. Interproton coupling constants are reported in Hertz (Hz).

LC-MS spectra were obtained using two different systems. For LCMS method 1, LC-MS spectra were obtained using an Agilent 12005L HPLC equipped with a 6130 mass spectrometer operating with electrospray ionization; chromatographic data were obtained using a Shimadzu Shimpack XR-ODS, 3.0×30 mm, 2.2 micron particle size column and a water:methanol gradient from 15% methanol to 95% methanol in 2.2 minutes under a 1.5 mL/min flow; a hold at 95% methanol was applied at the end of the gradient for 0.8 minutes; and both water and methanol mobile phases contained 0.1% formic acid. For LCMS method 2, LCMS spectra were obtained using a Waters ACQUITY UPLC™ equipped with a Thermofinnigan AQA™ mass spectrometer operating with electrospray ionization; chromatographic data were obtained using a Supelco® Analytical Ascentis® Express, 2.1×50 mm, 2.7 micron particle size column ($C_{18}$) and a water:acetonitrile gradient from 5% acetonitrile to 100% acetonitrile in 0.8 minute under a 1.5 mL/min flow; a hold at 100% methanol was applied at the end of the gradient for 0.05 minutes; and water mobile phase was buffered with ammonium acetate (10 mmolar) and 0.1% v./v. acetic acid. When LCMS retention times are reported as RT, LCMS method 1 or 2 is then specified.

When semi-preparative HPLC was carried out to purify reaction mixture, a modified Gilson HPLC system was used with offline regeneration; chromatographic data were obtained using a Varian Pursuit™ XRS, 21.4×50 mm, 10 micron particle size column (C18) and a water:methanol gradient from 40% methanol to 100% methanol in 5 minutes under a 28 mL/min flow; and water mobile phase was buffered with ammonium acetate (10 mmolar) and 0.1% v./v. ammonium hydroxide.

Compound No 1.008 of Example 1 was prepared according to the following general reaction Scheme 4:

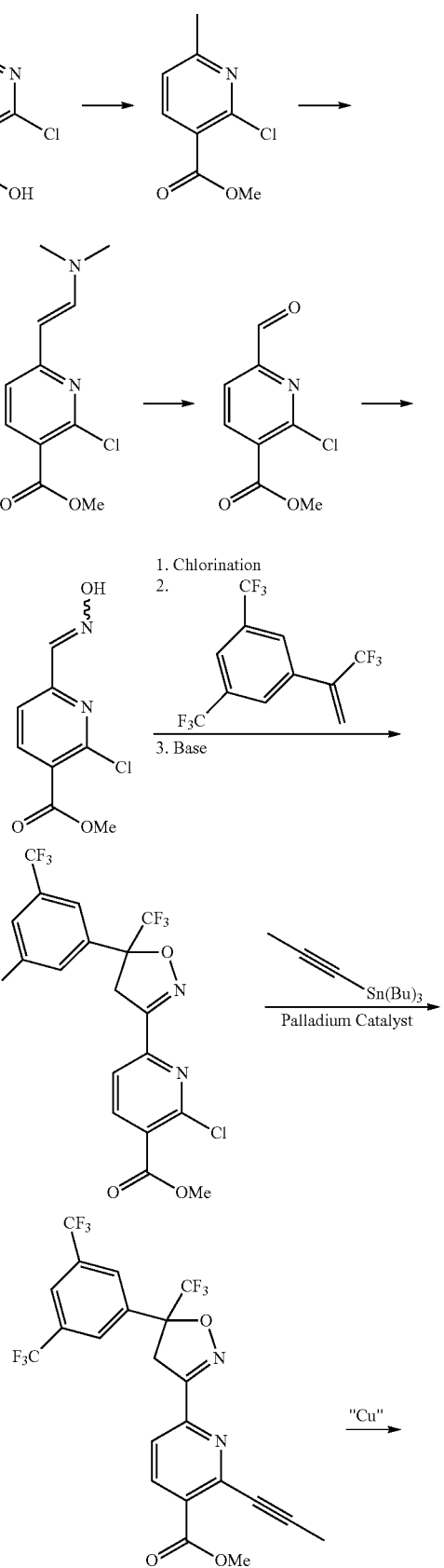

Scheme 4

65
-continued

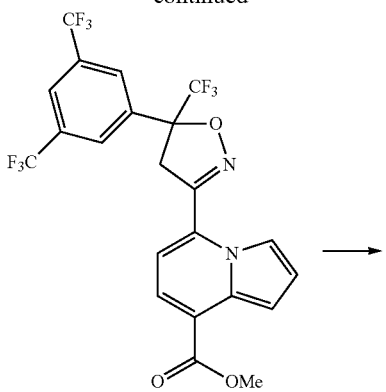

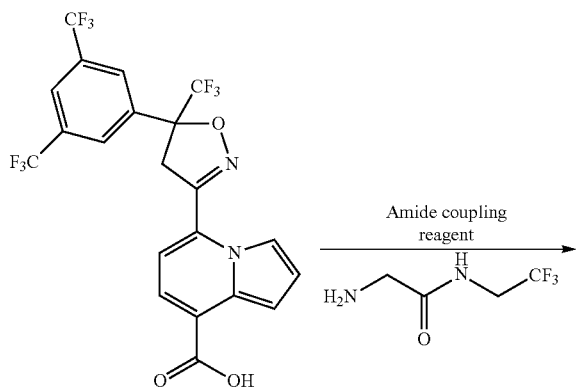

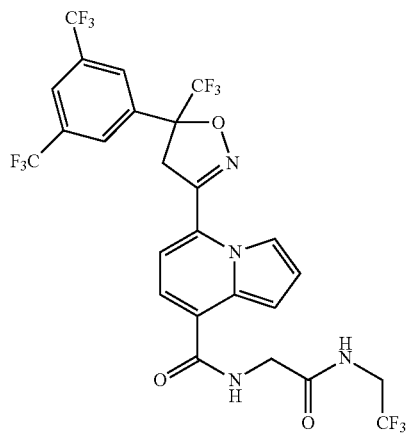

Compounds of Example 2 to 4 were prepared according to a general reaction scheme similar to the one above except that 1,3-dichloro-5-(1-trifluoromethylvinyl)-benzene was used in the [3+2] cycloaddition step instead of 1,3-bistrifluoromethyl-5-(1-trifluoromethylvinyl)-benzene and/or 2-methylthioethylamine was used in the last amide coupling step instead of 2-amino-N-(2,2,2-trifluoroethyl)acetamide.

Furthermore, it will be apparent to one of skill in the art that the synthetic sequence depicted in Scheme 4 may be used to prepare additional compounds with different substitution patterns by using alternative styrene derivative having the desired substitution pattern and alternative amines or alcohols in the last step.

66

Example 1

5-[5-(3,5-Bistrifluoromethylphenyl)-5-trifluoromethyl-4,5-dihydroisoxazol-3-yl]-indolizine-8-carboxylic acid [(2,2,2-trifluoroethylcarbamoyl)methyl]-amide (compound No 1.008)

5-[5-(3,5-Bistrifluoromethylphenyl)-5-trifluoromethyl-4,5-dihydroisoxazol-3-yl]-indolizine-8-carboxylic acid (50 mg), 1-ethyl-(3-dimethylaminopropyl)carbodiimide hydrochloride (EDAC.HCl, 22.5 mg), 1-hydroxybenzotriazole monohydrate (HOBt.H2O, 20 mg) and N-methylmorpholine (22 μL) were stirred in a mixture of DMF-DCM (1/2, 1 mL) for 20 minutes at room temperature prior to adding 2-amino-N-(2,2,2-trifluoroethyl)acetamide (50 mg, Ukrorgsynthesis Ltd. Kiev, UKRAINE). The reaction mixture was stirred overnight at room temperature. The mixture was diluted with water and EA. The organic layer was collected, washed with brine, dried over magnesium sulfate, filtered and concentrated under reduced pressure to give a residue that was purified by chromatography (SiO$_2$, DCM/MeOH) to afford the title compound as an orange-reddish solid (11.1 mg, 17%). MS (ES): M/Z [M+H]=649. 1H NMR (400 MHz, CHLOROFORM-d): 3.88-4.04 (m, 3H), 4.33 (d, J=5.3 Hz, 2H), 4.39 (d, J=16.6 Hz, 1H), 6.84 (d, J=7.4 Hz, 1H), 7.05-7.08 (m, 1H), 7.08-7.21 (m, 3H), 7.33 (t, J=4.9 Hz, 1H), 8.01 (s, 1H), 8.13 (s, 2H), 8.72 (d, J=1.8 Hz, 1H). 19F NMR (376 MHz, CHLOROFORM-d): −80.0 (s, 3F), −72.9 (t, J=9.2 Hz, 3F), −63.3 (s, 6F).

The starting material, 5-[5-(3,5-bistrifluoromethylphenyl)-5-trifluoromethyl-4,5-dihydroisoxazol-3-yl]-indolizine-8-carboxylic acid, was prepared as follows:

a. Oxalyl chloride (9.3 mL) was added to a solution of 2-chloro-6-methyl-nicotinic acid (9 g) in DCM (500 mL). After stirring 30 minutes, the mixture was concentrated under reduced pressure to give a residue that was treated with MeOH (500 mL) at 0° C. After stirring overnight at room temperature, the mixture was concentrated under reduced pressure to give a residue that was diluted with water and EA, neutralized with a saturated aqueous solution of sodium bicarbonate solution and extracted three times with EA. The organic layer was collected, washed with brine, dried over sodium sulfate, filtered and concentrated under reduced pressure to afford 2-chloro-6-methyl-nicotinic acid methyl ester (9.7 g, 99%). 1H NMR (400 MHz, CHLOROFORM-d): 2.60 (s, 3H), 3.95 (s, 3H), 7.17 (d, J=7.8 Hz, 1H), 8.09 (d, J=7.8 Hz, 1H).

b. A mixture of 2-chloro-6-methyl-nicotinic acid methyl ester (2 g) in DMF (10 mL) and DMFDMA (3 mL) were heated to 110° C. for 16 hours prior to adding more DMFDMA (1 mL). After 3 hours at 110° C., the mixture was cooled to room temperature, diluted with water and extracted three times with EA. The organic layer was collected, washed with brine, dried over sodium sulfate, filtered and concentrated under reduced pressure to give a residue that was purified by chromatography (SiO$_2$, Heptane/EA/MeOH) to afford 2-chloro-6-(-2-dimethylaminovinyl)-nicotinic acid methyl ester (1.2 g, 46%). 1H NMR (400 MHz, CHLOROFORM-d): 2.96 (s, 6H), 3.87 (s, 3H), 5.09 (d, J=12.9 Hz, 1H), 6.71 (d, J=8.4 Hz, 1H), 7.68 (d, J=12.9 Hz, 1H), 7.92 (d, J=8.2 Hz, 1H).

c. Sodium periodate (2.14 g) was added to a solution of 2-chloro-6-(-2-dimethylaminovinyl)-nicotinic acid methyl ester (1.2 g) in a mixture of THF (40 mL) and water (10 mL). After one hour stirring at room temperature, the mixture was quenched with an aqueous solution of sodium thiosulfate and filtered through a plug of Celite®. The filtrate was diluted with more water and extracted three times with EA. The organic layer was collected, washed with brine, dried over sodium sulfate, filtered and concentrated under reduced pressure to afford 2-chloro-6-formyl-nicotinic acid methyl ester (1.02 g) that was used without further purification into next step.

d. A 50% solution of hydroxylamine in water (1 mL) was added to a solution 2-chloro-6-formyl-nicotinic acid methyl ester in a mixture of THF (40 mL) and water (10 mL). After one hour at room temperature, the reaction was quenched with an aqueous solution of sodium thiosulfate and extracted three times with EA. The organic layer was collected, washed with brine, dried over magnesium sulfate, filtered and concentrated under reduced pressure to afford 2-chloro-6-(hydroxyiminomethyl)-nicotinic acid methyl ester as solid residue (1 g) that was used without further purification into next step.

e. N-Chlorosuccinimide (667 mg) was added to a solution of 2-chloro-6-(hydroxyiminomethyl)-nicotinic acid methyl ester in DMF (5 mL) and the mixture heated to 40° C. for 20 minutes. The mixture was cooled to around 0° C. (ice bath) and then 1,3-bistrifluoromethyl-5-(1-trifluoromethylvinyl)-benzene (2 g, prepared from commercially available 2-bromo-3,3,3-trifluoropropene and 3,5-bistrifluoromethylphenylboronic acid by the method described in *J. Fluorine. Chem.* 1999, 95, 167-170) and TEA (0.75 mL) were added and the mixture stirred at room temperature overnight. The mixture was diluted with water and extracted three times with EA. The organic layer was collected, washed with brine, dried over magnesium sulfate, filtered and concentrated under reduced pressure to give a residue that was purified by chromatography (SiO$_2$, Heptane/EA) to afford 6-[5-(3,5-bistrifluoromethylphenyl)-5-trifluoromethyl-4,5-dihydroisoxazol-3-yl]-2-chloro-nicotinic acid methyl ester (500 mg, 22% over 3 steps). MS (ES): M/Z [M+H]=521. RT=2.24 min (LCMS method 1).

f. 6[5-(3,5-Bistrifluoromethylphenyl)-5-trifluoromethyl-4,5-dihydroisoxazol-3-yl]-2-chloro-nicotinic acid methyl ester (490 mg), tributyl(1-propyl)tin (426 mg) and [1,1'-bis(diphenylphosphino)ferrocene] dichloropalladium(II) (39.5 mg) in toluene (10 mL) were stirred heated to 90° C. overnight. The mixture was let cool to room temperature and then stirred with a saturated aqueous solution of potassium fluoride. The mixture was extracted three times with EA. The organic layers were combined, washed with brine, dried over sodium sulfate, filtered through a plug of Celite® and concentrated under reduced pressure to give a residue that was purified by chromatography (SiO$_2$, Heptane/EA) to afford 6-[5-(3,5-bistrifluoromethylphenyl)-5-trifluoromethyl-4,5-dihydroisoxazol-3-yl]-2-prop-1-ynyl-nicotinic acid methyl ester (360 mg, 64%). 1H NMR (400 MHz, CHLOROFORM-d): 2.21 (s, 3H), 3.87-4.04 (m, 4H), 4.43 (d, J=18.4 Hz, 1H), 7.97 (s, 1H), 8.01 (d, J=8.2 Hz, 1H), 8.08 (s, 2H), 8.26 (d, J=8.4 Hz, 1H). 19F NMR (376 MHz, CHLOROFORM-d): −80.2 (s, 3F), −63.3 (s, 6F)

g. 6-[5-(3,5-Bistrifluoromethylphenyl)-5-trifluoromethyl-4,5-dihydroisoxazol-3-yl]-2-prop-1-ynyl-nicotinic acid methyl ester (250 mg), copper(I) chloride (35 mg), TEA (0.3 mL) in DMA (3 mL) were stirred heated to 130° C. overnight. The mixture was cooled to room temperature and diluted with water. The mixture was extracted three times with EA. The organic layers were combined, washed with brine, dried over sodium sulfate, filtered and concentrated under reduced pressure to give a residue that was purified by chromatography (SiO$_2$, Heptane/EA) to afford 5-[5-(3,5-bis-trifluoromethylphenyl)-5-trifluoromethyl-4,5-dihydroisoxazol-3-yl]-indolizine-8-carboxylic acid methyl ester as an orange-reddish solid (54 mg). MS (ES): M/Z [M+H]=525. RT=2.35 min (LCMS method 1).

h. 5-[5-(3,5-Bistrifluoromethylphenyl)-5-trifluoromethyl-4,5-dihydroisoxazol-3-yl]-indolizine-8-carboxylic acid methyl ester (94.5 mg) and lithium hydroxide (16 mg) were stirred in a 4 to 1 mixture of THF/Water (4 mL) at room temperature for 6 hours before dilution with more water. The mixture was acidified to pH around 3 with a 10% aqueous solution of hydrochloric acid and extracted with EA. The organic layer was collected, dried over magnesium sulfate, filtered and concentrated under reduced pressure to give an orange-reddish residue (88 mg) used directly in the next amide coupling step.

Example 2

5-[5-(3,5-Bistrifluoromethylphenyl)-5-trifluoromethyl-4,5-dihydroisoxazol-3-yl]-indolizine-8-carboxylic acid (2-methylthioethyl)-amide (compound No 1.009)

Using a procedure similar to that described in Example 1, except using 2-methylthioethylamine, the title compound was isolated as an orange-reddish solid (10.1 mg, 23%). MS (ES): M/Z [M+H]=584. 1H NMR (400 MHz, CHLOROFORM-d): 2.18 (s, 3H), 2.83 (t, J=6.2 Hz, 2H), 3.76 (q, J=6.0 Hz, 2H), 3.98 (d, J=16.6 Hz, 1H), 4.41 (d, J=16.6 Hz, 1H), 6.79 (t, J=4.8 Hz, 1H), 6.90 (d, J=7.2 Hz, 1H), 7.05-7.11 (m, 1H), 7.13 (d, J=3.1 Hz, 1H), 7.20 (d, J=7.4 Hz, 1H), 8.00 (s, 1H), 8.13 (s, 2 H), 8.75 (d, J=1.6 Hz, 1H). 19F NMR (376 MHz, CHLOROFORM-d): −80.0 (s, 3F), −63.3 (s, 6F).

Example 3

5-[5-(3,5-Dichlorophenyl)-5-trifluoromethyl-4,5-dihydroisoxazol-3-yl]-indolizine-8-carboxylic acid [(2,2,2-trifluoroethylcarbamoyl)methyl]-amide (compound No 1.011)

Using a procedure similar to that described in Example 1, except using 5-[5-(3,5-dichlorophenyl)-5-trifluoromethyl-4,5-dihydroisoxazol-3-yl]-indolizine-8-carboxylic acid (73 mg), the title compound was isolated as an orange-reddish solid (25.2 mg, 26%). MS (ES): M/Z [M+H]=581. 1HNMR (400 MHz, CHLOROFORM-d): 3.80-4.01 (m, 3H), 4.24 (d, J=16.6 Hz, 1H), 4.29 (d, J=5.1 Hz, 2H), 6.77 (d, J=7.4 Hz, 1H), 6.97-7.05 (m, 1H), 7.09 (d, J=3.3 Hz, 1H), 7.12 (d, J=7.4 Hz, 1H), 7.22 (br. s., 1H), 7.34 (t, J=5.0 Hz, 1H), 7.43 (t, J=1.6 Hz, 1H), 7.52 (s, 2H), 8.69 (d, J=1.8 Hz, 1H). 19F NMR (376 MHz, CHLOROFORM-d): −79.8 (s, 3F), −72.8 (s, 6F).

The starting material, 5-[5-(3,5-dichlorophenyl)-5-trifluoromethyl-4,5-dihydroisoxazol-3-yl]-indolizine-8-carboxylic acid, was prepared using a procedure similar to that described in Example 1, except using in part e, 1,3-dichloro-

Example 4

5-[5-(3,5-Dichlorophenyl)-5-trifluoromethyl-4,5-dihydroisoxazol-3-yl]-indolizine-8-carboxylic acid (2-methylthioethyl)-amide (compound No 1.013)

Using a procedure similar to that described in Example 1, except using 5-[5-(3,5-dichlorophenyl)-5-trifluoromethyl-4,5-dihydroisoxazol-3-yl]-indolizine-8-carboxylic acid (37 mg, described above in Example 3) and 2-methylthioethyl-amine, the title compound was isolated as an orange-reddish solid (21.2 mg, 49%). MS (ES): M/Z [M+H]=516. 1H NMR (400 MHz, CHLOROFORM-d): 2.17 (s, 3H), 2.83 (t, J=6.2 Hz, 2H), 3.75 (q, J=6.0 Hz, 2H), 3.91 (d, J=16.6 Hz, 1H), 4.28 (d, J=16.6 Hz, 1H), 6.83 (d, J=7.4 Hz, 1H), 7.02-7.08 (m, 1H), 7.17 (d, J=7.2 Hz, 1H), 7.46 (t, J=1.7 Hz, 1H), 7.55 (s, 2 H), 8.73 (d, J=1.6 Hz, 1H). 19F NMR (376 MHz, CHLOROFORM-d): −79.8 (s, 3F).

Compound No 1.006 of Example 5 was prepared according to the following general reaction Scheme 5:

Scheme 5

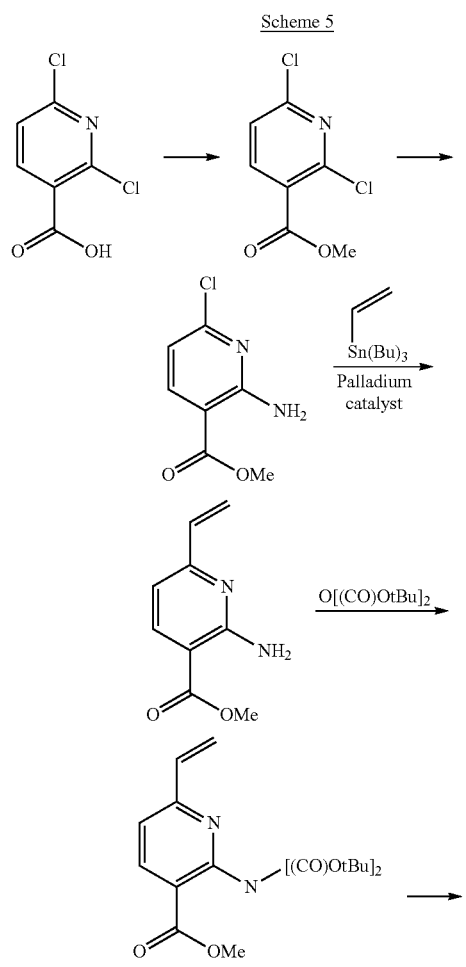

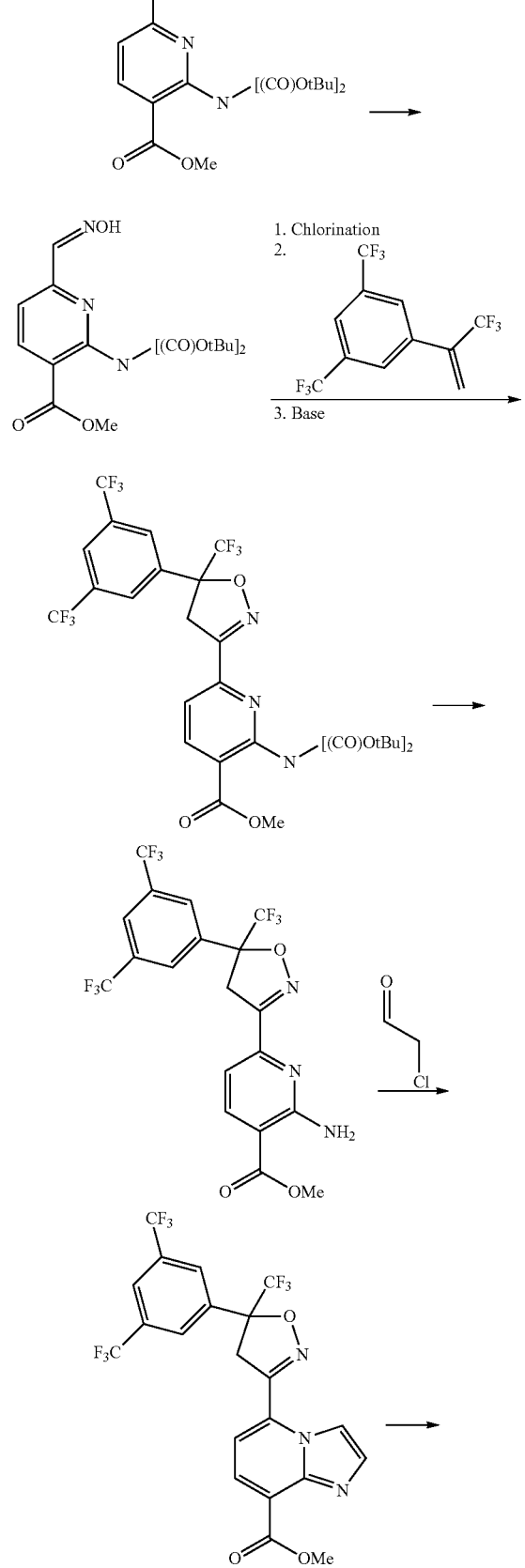

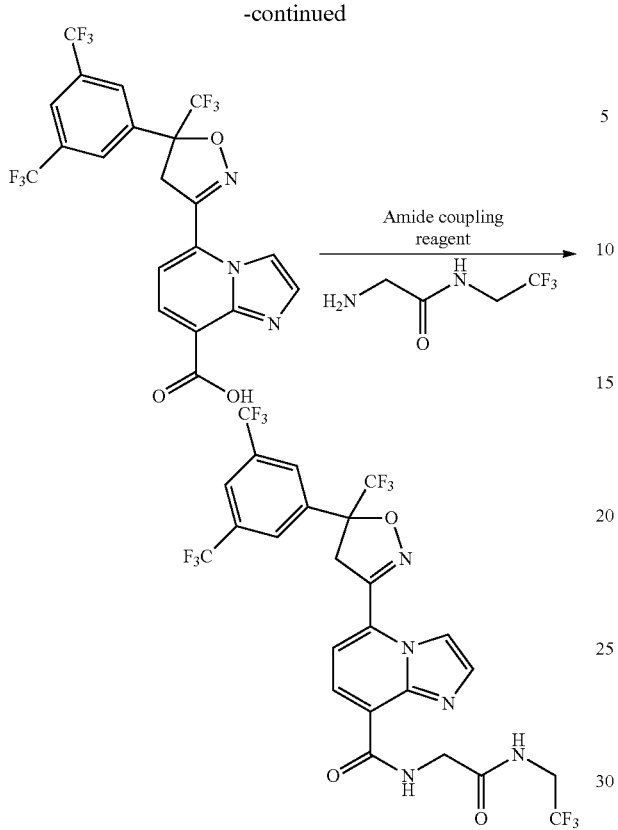

Compound no 1.007 of Example 6 was prepared according to a general reaction scheme similar to the one above except that 2-methylthioethylamine was used in the last amide coupling step instead of 2-amino-N-(2,2,2-trifluoroethyl) acetamide.

Further, it will be apparent to one of skill in the art that the synthetic sequence depicted in Scheme 5 may be used to prepare additional compounds having different substituents by using alternative styrene derivatives having the desired substitution pattern and alternative amines or alcohols to obtain the desired amide or ester in the last step.

Example 5

5-[5-(3,5-Bistrifluoromethylphenyl)-5-trifluoromethyl-4,5-dihydroisoxazol-3-yl]-imidazo[1,2-a]pyridine-8-carboxylic acid [(2,2,2-trifluoroethylcarbamoyl)methyl]-amide (compound No 1.006)

Using a procedure similar to that described in Example 1, except using 5-[5-(3,5-bistrifluoromethylphenyl)-5-trifluoromethyl-4,5-dihydroisoxazol-3-yl]-imidazo[1,2-a]pyridine-8-carboxylic acid (45 mg), the title compound was isolated as an orange-reddish solid (13.1 mg, 23%). MS (ES): M/Z [M+H]=650. 1H NMR (400 MHz, CHLOROFORM-d): 3.85-4.08 (m, 3H), 4.33 (d, J=6.1 Hz, 2H), 4.44 (d, J=16.8 Hz, 1H), 6.86-7.04 (m, 1H), 7.22 (d, J=7.6 Hz, 1H), 7.87 (d, J=1.0 Hz, 1H), 8.02 (s, 1H), 8.12 (s, 2H), 8.26 (d, J=7.6 Hz, 1H), 8.92 (d, J=1.0 Hz, 1H), 10.85-11.06 (m, 1H). 19F NMR (376 MHz, CHLOROFORM-d): −80.1 (s, 3F), −72.9 (t, J=9.2 Hz, 3F), −63.3 (s, 6F).

The starting material, 5-[5-(3,5-bistrifluoromethylphenyl)-5-trifluoromethyl-4,5-dihydroisoxazol-3-yl]-imidazo[1,2-a]pyridine-8-carboxylic acid, was prepared as follows:

a. Oxalyl chloride (11.1 mL) was added to a solution of 2,6-dichloronicotinic acid (8 g) in a mixture of DCM (300 mL) and DMF (0.2 mL). After stirring 2 hours, the mixture was concentrated under reduced pressure to give a residue that was treated with MeOH (300 mL) at 0° C. The mixture was stirred at to room temperature and then was concentrated under reduced pressure to give a residue that was diluted with water and EA, neutralized with a saturated aqueous solution of sodium bicarbonate solution and extracted three times with EA. The organic layers were combined, washed with brine, dried over sodium sulfate, filtered and concentrated under reduced pressure to afford 2,6-dichloronicotinic acid methyl ester (8 g, 93%). 1H NMR (400 MHz, CHLOROFORM-d): 3.96 (s, 3H), 7.36 (d, J=8.2 Hz, 1H), 8.16 (d, J=8.0 Hz, 1H).

b. A concentrated solution of ammonium hydroxide (2 mL) was added to a solution of 2-chloro-6-methyl-nicotinic acid methyl ester (2 g) in 1,4-dioxane (2 mL). The mixture in a 10 mL microwave Pyrex tube was cap sealed and heated to 100° C. for 20 minutes using a Discover CEM microwave unit (CEM, Matthews, NC-USA). This reaction was set-up three more times using exactly the same conditions. The 4 reaction mixtures were combined and concentrated under reduced pressure to afford a residue that was diluted with water and extracted three times with EA.

The organic layers were combined, washed with brine, dried over magnesium sulfate, filtered and concentrated under reduced pressure to give a residue that was purified by chromatography (SiO$_2$, Heptane/EA) to afford 2-amino-6-chloro-nicotinic acid methyl ester (3.44 g, 47%). 1H NMR (400 MHz, CHLOROFORM-d): 3.89 (s, 3H), 6.63 (d, J=8.0 Hz, 1H), 8.06 (d, J=8.0 Hz, 1H).

c. 2-Amino-6-chloro-nicotinic acid methyl ester (3.44 g), tributyl(vinyl)tin (5.4 mL) and tetrakis(triphenylphosphine)palladium(0) (6.5 g) in xylene (200 mL) were stirred heated to 130° C. After 1.5 hours, the mixture was let cool to room temperature and then stirred with a saturated aqueous solution of potassium fluoride for 1.5 hours and filtered over a plug of Celite®. The filtrate was extracted three times with EA. The organic layers were combined, washed with brine, dried over sodium sulfate, filtered and concentrated under reduced pressure to afford 2-amino-6-vinyl-nicotinic acid methyl ester (1.7 g, 52%). 1H NMR (400 MHz, CHLOROFORM-d): 3.89 (s, 3H), 5.54 (dd, J=10.6, 0.9 Hz, 1H), 6.27 (d, J=17.4 Hz, 1H), 6.46 (br. s., 2H), 6.59-6.74 (m, 2H), 8.10 (d, J=8.0 Hz, 1H).

d. 2-Amino-6-vinyl-nicotinic acid methyl ester (1.7 g), di-tert-butyl dicarbonate (8.3 g) and 4-dimethylaminopyridine (1.4 g) in DCM (100 mL) were heated to 40° C. overnight. The mixture was concentrated under reduced pressure to give a residue that was purified by chromatography (SiO$_2$, Heptane/EA/MeOH) to give 2-bis(tert-butoxycarbonyl)amino-6-vinyl-nicotinic acid methyl ester (2.85 g, 79%). 1H NMR (400 MHz, CHLOROFORM-d): 1.40 (s, 18H), 3.90 (s, 3H), 5.63 (d, J=10.9 Hz, 1H), 6.33 (d, J=17.4 Hz, 1H), 6.83 (dd, J=17.4, 10.7 Hz, 1H), 7.37 (d, J=8.0 Hz, 1H), 8.32 (d, J=8.0 Hz, 1H).

e. 2-Bis(tert-butoxycarbonyl)amino-6-vinyl-nicotinic acid methyl ester (2.85 g) dissolved in a mixture of DCM (75 mL) and methanol (25 mL) was treated with ozone gas for 10 minutes. After stirring 15 minutes at −78° C., the mixture was purged with oxygen and 20 minutes with nitrogen and then quenched with dimethyl sulfide (0.5 mL) followed by a 10% solution of sodium thiosulfate (10 mL) and diluted with DCM. The organic layer was dried over sodium sulfate, filtered and concentrated under reduced pressure to give 2-bis(tert-butoxycarbonyl)amino-6-formyl-nicotinic acid methyl ester that was used without further purification into next step. 1H NMR (400 MHz, CHLOROFORM-d): 1.42 (s, 18H), 3.95 (s, 3H), 8.01 (d, J=7.8 Hz, 1H), 8.52 (d, J=7.8 Hz, 1H), 10.07 (s, 1H).

f. A 50% solution of hydroxylamine in water (1.5 mL) was added to a solution 2-bis(tert-butoxycarbonyl)amino-6-formyl-nicotinic acid methyl ester in EtOH (50 mL). After one hour at room temperature, the reaction was diluted with water and concentrated under reduced pressure to remove EtOH. The residual mixture was extracted three times with EA. The organic layers were combined, washed with brine, dried over magnesium sulfate, filtered and concentrated under reduced pressure to afford 2-bis(tert-butoxycarbonyl)amino-6-(hydroxyiminomethyl)-nicotinic acid methyl ester as solid residue (2.77 g, 93% over two steps). 1H NMR (400 MHz, CHLOROFORM-d): 1.40 (s, 18H), 3.92 (s, 3H), 7.87 (d, J=8.2 Hz, 1H), 8.22 (s, 1H), 8.37 (d, J=8.0 Hz, 2H).

g. N-Chlorosuccinimide (0.94 g) was added to a solution of 2-bis(tert-butoxycarbonyl)amino-6-(hydroxyiminomethyl)-nicotinic acid methyl ester (2.77 g) in DNIF (10 mL) and mixture heated to 40° C. for 2 hours. The mixture was cooled to around 0° C. (ice bath) and then 1,3-bistrifluoromethyl-5-(1-trifluoromethylvinyl)-benzene (2.8 g described in Example 1) and TEA (1.05 mL) were added and the mixture stirred at room temperature overnight. The mixture was diluted with water and extracted three times with EA. The organic layers were combined, washed with brine, dried over magnesium sulfate, filtered and concentrated under reduced pressure to give a residue that was purified by chromatography (SiO₂, Heptane/EA) to afford 6-[5-(3,5-bistrifluoromethyl-phenyl)-5-trifluoromethyl-4,5-dihydro-isoxazol-3-yl]-2-bis(tert-butoxycarbonyl) amino-nicotinic acid methyl ester (2.14 g, 43%). 1H NMR (400 MHz, CHLOROFORM-d): 1.43 (s, 18H), 3.93 (d, J=18.0 Hz, 1H), 3.93 (s, 3H), 4.33 (d, J=18.2 Hz, 1 H), 7.98 (s, 1H), 8.04-8.13 (m, 3H), 8.44 (d, J=8.0 Hz, 1H). 19F NMR (376 MHz, CHLOROFORM-d): −80.2 (s, 3F), −63.3 (s, 6F).

h. TFA (5 mL) was added to a solution of 6-[5-(3,5-bistrifluoromethyl-phenyl)-5-trifluoromethyl-4,5-dihydro-isoxazol-3-yl]-2-bis(tert-butoxycarbonyl) amino-nicotinic acid methyl ester (2.14 g) in DCM (40 mL). After stirring overnight at room temperature, the mixture was quenched with a saturated aqueous solution of sodium bicarbonate solution and extracted three times with DCM. The organic layers were combined, washed with brine, dried over sodium sulfate, filtered and concentrated under reduced pressure to afford 2-amino-6-[5-(3,5-bistrifluoromethyl-phenyl)-5-trifluoromethyl-4,5-dihydro-isoxazol-3-yl]-nicotinic acid methyl ester (1.12 g, 73%) as a solid. 1H NMR (400 MHz, CHLOROFORM-d): 3.84 (d, J=18.2 Hz, 1H), 3.91 (s, 3H), 4.30 (d, J=18.4 Hz, 1H), 6.44 (br. s., 2H), 7.34 (d, J=8.0 Hz, 1H), 7.97 (s, 1H), 8.08 (s, 2H), 8.19 (d, J=8.0 Hz, 1H). 19F NMR (376 MHz, CHLOROFORM-d): −80.1 (s, 3F), −63.3 (s, 6F).

i. 2-Amino-6-[5-(3,5-bistrifluoromethylphenyl)-5-trifluoromethyl-4,5-dihydro-isoxazol-3-yl]-nicotinic acid methyl ester (200 mg) and a 50% aqueous solution of chloroacetaldehyde (0.4 mL) in isopropanol (2 mL) were stirred heated to 50° C. over the week-end. The mixture was cooled to room temperature and diluted with water and EA, neutralized with a saturated aqueous solution of sodium bicarbonate solution and extracted three times with EA. The organic layers were combined, washed with brine, dried over sodium sulfate, filtered and concentrated under reduced pressure to give a residue that was purified by chromatography (SiO₂, DCM/MeOH) to afford 5-[5-(3,5-bistrifluoromethylphenyl)-5-trifluoromethyl-4,5-dihydroisoxazol-3-yl]-imidazo[1,2-a]pyridine-8-carboxylic acid methyl ester as a solid (200 mg).

j. 5-[5-(3,5-Bistrifluoromethylphenyl)-5-trifluoromethyl-4,5-dihydroisoxazol-3-yl]-imidazo[1,2-a]pyridine-8-carboxylic acid methyl ester (200 mg) and lithium hydroxide (45 mg) were stirred in a 4 to 1 mixture of THF/Water (2 mL) at room temperature for 20 minutes before dilution with more water. The mixture was acidified to pH around 3 with a 10% aqueous solution of hydrochloric acid and extracted with EA. The organic layer was collected, dried over magnesium sulfate, filtered and concentrated under reduced pressure to give a residue used directly in the next amide coupling step.

Example 6

5-[5-(3,5-Bistrifluoromethylphenyl)-5-trifluoromethyl-4,5-dihydroisoxazol-3-yl]-imidazo[1,2-a]pyridine-8-carboxylic acid (2-methylthioethyl)-amide (compound No 1.007)

Using a procedure similar to that described in Example 1, except using 5-[5-(3,5-bistrifluoromethylphenyl)-5-trifluoromethyl-4,5-dihydroisoxazol-3-yl]-imidazo[1,2-a]pyridine-8-carboxylic acid (45 mg) and 2-methylthioethylamine (0.016 mL), the title compound was isolated as an orange-reddish solid (11.9 mg, 23%). MS (ES): M/Z [M+H]=585. 1H NMR (400 MHz, CHLOROFORM-d): 2.22 (s, 3 H), 2.85 (t, J=6.8 Hz, 2 H), 3.82 (q, J=6.6 Hz, 2 H), 4.01 (d, J=17.0 Hz, 1H), 4.44 (d, J=16.8 Hz, 1 H), 7.21 (d, J=7.6 Hz, 1H), 7.85 (s, 1H), 8.02 (s, 1 H), 8.12 (s, 2H), 8.28 (d, J=7.6 Hz, 1H), 8.90 (d, J=1.0 Hz, 1H), 10.67 (br. s., 1H). 19F NMR (376 MHz, CHLOROFORM-d): −80.0 (s, 3F), −63.3 (s, 6F). Compound No 2.004 of Example 7 was prepared according to the following general reaction Scheme 6:

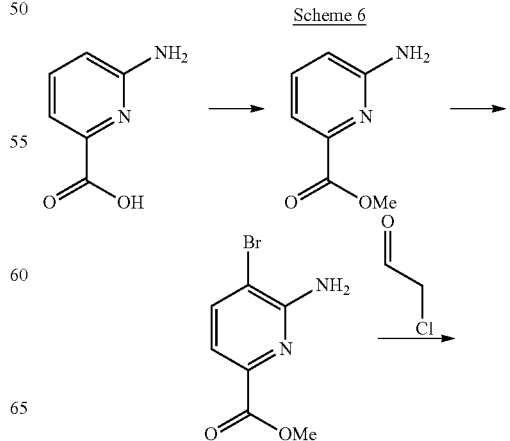

-continued

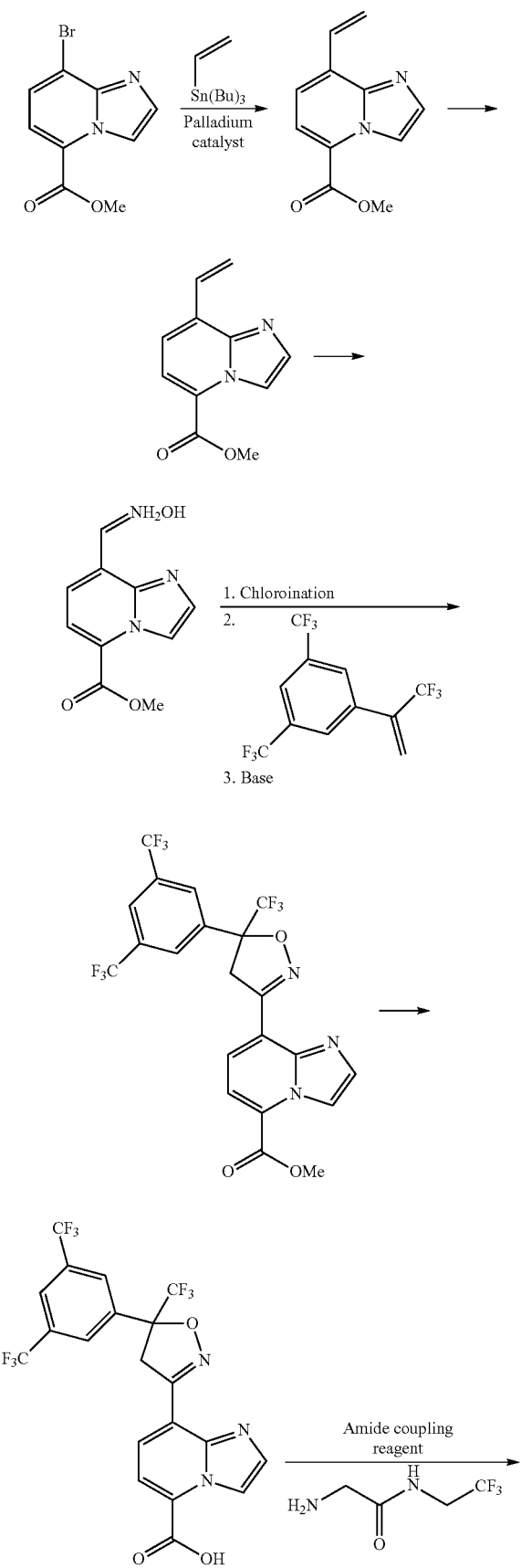

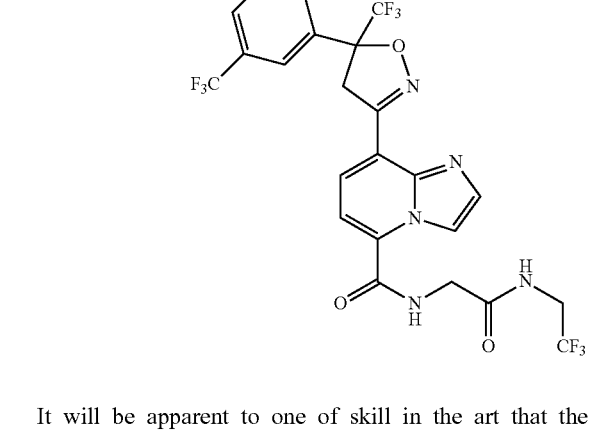

It will be apparent to one of skill in the art that the synthetic sequence depicted in Scheme 6 may be used to prepare additional compounds having different substituents by using the appropriate reagents. For example, compounds having different substituents on the phenyl ring may be prepared by using an alternative styrene derivative having the desired substitution pattern. Further, it will be apparent that a variety of amines or alcohols may be utilized to obtain the desired amide or ester in the last step.

Example 7

8-[5-(3,5-Bistrifluoromethylphenyl)-5-trifluoromethyl-4,5-dihydroisoxazol-3-yl]-imidazo[1,2-a]pyridine-5-carboxylic acid 1(2,2,2-trifluoroethylcarbamoyl)methyl]-amide (compound No 2.004)

Using a procedure similar to that described in Example 1, except using 8-[5-(3,5-bistrifluoromethylphenyl)-5-trifluoromethyl-4,5-dihydroisoxazol-3-yl]-imidazo[1,2-a]pyridine-5-carboxylic acid, the title compound was isolated as a solid (2.9 mg). MS (ES): M/Z [M+H]=650. 1H NMR (400 MHz, CHLOROFORM-d): 3.91-4.07 (m, 2H), 4.27 (d, J=4.9 Hz, 2H), 4.33-4.47 (m, 1H), 4.76-4.89 (m, 1H), 6.20-6.38 (m, 1H), 7.10-7.22 (m, 1H), 7.30-7.40 (m, 1H), 7.77 (s, 1H), 7.84-7.92 (m, 1H), 7.97 (s, 1H), 8.15 (s, 2H), 8.62 (s, 1H). 19F NMR (376 MHz, CHLOROFORM-d): −80.1 (s, 3F), −72.9 (m, 3F), −63.3 (s, 6F).

The starting material, 8-[5-(3,5-bistrifluoromethylphenyl)-5-trifluoromethyl-4,5-dihydroisoxazol-3-yl]-imidazo[1,2-a]pyridine-5-carboxylic acid, was prepared as follows:
a. Sulfuric acid was added to a solution of 6-aminopyridine-2-carboxylic acid (10 g) in methanol (300 mL) and the mixture was heated to reflux overnight. The mixture was cooled to room temperature and then was concentrated under reduced pressure to give a residue that was diluted with water and EA, neutralized with a saturated aqueous solution of sodium bicarbonate solution and extracted three times with EA. The organic layers were combined, washed with brine, dried over sodium sulfate, filtered and concentrated under reduced pressure to afford 6-aminopyridine-2-carboxylic acid methyl ester (8.5 g, 77%). MS (ES): M/Z [M+H]=153. 1H NMR (400 MHz, CHLOROFORM-d): 3.96 (s, 3H), 4.77 (br. s., 2H), 6.67 (d, J=8.2 Hz, 1H), 7.50 (d, J=7.0 Hz, 1H) and 7.55 (t, J=7.7 Hz, 1H).
b. A solution of bromine (2.57 ml) in chloroform (40 mL) was slowly added over 30 minutes to a solution of 6-aminopyridine-2-carboxylic acid methyl ester (6.92 g) in chloroform (300 mL). The mixture was stirred overnight at room temperature and then loaded on silica and purified by chromatography (SiO$_2$, Heptane/EA) to afford 6-amino-5-bromopyridine-2-carboxylic acid methyl ester as a solid (2 g, 19%) along with 6-amino-3-bromopyridine-2-carboxylic acid methyl ester (3 g, 29%) and 6-amino-3,5-dibromopyridine-2-carboxylic acid methyl ester (2.6 g, 18%). 1H NMR (400 MHz, CHLOROFORM-d): 3.97 (s, 3H), 5.22 (br. s., 2H) 7.38 (d, J=7.8 Hz, 1H) and 7.79 (d, J=7.8 Hz, 1H)

c. 6-Amino-5-bromopyridine-2-carboxylic acid methyl ester (2 g) and a 50% aqueous solution of chloroacetaldehyde (2.8 mL) in isopropanol (100 mL) were stirred heated to 70° C. overnight. More of the 50% aqueous solution of chloroacetaldehyde (0.35 mL) was added at room temperature and the mixture was stirred heated to 80° C. for an additional 3 hours. The mixture was cooled to room temperature, loaded on silica and purified by chromatography (SiO$_2$, Heptane/EA) to afford afford 8-bromo-imidazo[1,2-a]pyridine-5-carboxylic acid methyl ester as a solid (2.3 g). MS (ES): M/Z [M+H]=255. 1H NMR (400 MHz, CHLOROFORM-d): 4.00 (s, 3H), 7.51 (d, J=7.6 Hz, 1H), 7.63 (d, J=7.8 Hz, 1H), 7.82 (s, 1H) and 8.90 (s, 1H)

d. 8-Bromo-imidazo[1,2-a]pyridine-5-carboxylic acid methyl ester (2.03 g), tributyl(vinyl)tin (2.7 mL) and 1'-bis(diphenylphosphino)ferrocene-palladium(II)dichloride (323 mg) in toluene (100 mL) were stirred heated to 70° C. overnight. More tributyl(vinyl)tin (2.7 mL) was added at room temperature and the mixture was stirred heated to 90° C. overnight. The mixture was let cool to room temperature and then stirred with a saturated aqueous solution of potassium fluoride for 1.5 hours and filtered over a plug of Celite®. The filtrate was extracted three times with EA. The organic layers were combined, washed with brine, dried over sodium sulfate, filtered and concentrated under reduced pressure to afford a residue that was purified by chromatography (SiO$_2$, Heptane/EA) to afford 8-vinyl-imidazo [1,2-a]pyridine-5-carboxylic acid methyl ester (753 mg, 42%). 1H NMR (400 MHz, CHLOROFORM-d): 4.02 (s, 3H), 5.75 (d, J=11.3 Hz, 1H), 6.58 (d, J=17.6 Hz, 1H), 7.28-7.38 (m, 2H), 7.71-7.85 (m, 2H) and 8.89 (s, 1H).

e. Sodium periodate (216 mg) was added to a solution of 8-vinyl-imidazo[1,2-a]pyridine-5-carboxylic acid methyl ester (98 mg) in a mixture of THF (4 mL) and water (1 mL). After stirring at room temperature, an aqueous solution of osmium tetroxide (4%) was added and the mixture let to stir for 4 hours. The mixture was then quenched with an aqueous solution of sodium thiosulfate and filtered through a plug of Celite®. The filtrate was diluted with more water and extracted three times with EA. The organic layer was collected, washed with brine, dried over sodium sulfate, filtered and concentrated under reduced pressure to afford 8-formyl-imidazo[1,2-a]pyridine-5-carboxylic acid methyl ester (1.02 g) that was used without further purification into next step.

f. A 50% solution of hydroxylamine in water (1.5 mL) was added to a solution 8-formyl-imidazo[1,2-a]pyridine-5-carboxylic acid methyl ester (0.29 mmole) in EtOH (3 mL). After one hour at room temperature, the reaction was diluted with water and concentrated under reduced pressure to remove EtOH. The residual mixture was extracted three times with EA. The organic layers were combined, washed with brine, dried over magnesium sulfate, filtered and concentrated under reduced pressure to give a residue that was purified by chromatography (SiO$_2$, Heptane/EA) to afford 8-(hydroxyimino-methyl)-imidazo[1,2-a]pyridine-5-carboxylic acid methyl ester as solid residue (12 mg).

g. N-Chlorosuccinimide (16.2 mg) was added to a solution of 8-(hydroxyimino-methyl)-imidazo[1,2-a]pyridine-5-carboxylic acid methyl ester (12 mg) in DMF (0.5 mL) and mixture heated to 40° C. for 20 minutes. The mixture was cooled to around 0° C. (ice bath) and then 1,3-bistrifluoromethyl-5-(1-trifluoromethylvinyl)-benzene (22 mg described in Example 1) and TEA (15 µL) were added and the mixture stirred at room temperature. The mixture was purified by chromatography (SiO$_2$, Heptane/EA) to afford 8-[5-(3,5-bistrifluoromethylphenyl)-5-trifluoromethyl-4,5-dihydroisoxazol-3-yl]-imidazo[1,2-a]pyridine-5-carboxylic acid methyl ester (11 mg, 39%). MS (ES): M/Z [M+H]=526. 19F NMR (376 MHz, CHLOROFORM-d): −80.2 (s, 3F) and −63.3 (s, 6F).

h. 8-[5-(3,5-Bistrifluoromethylphenyl)-5-trifluoromethyl-4,5-dihydroisoxazol-3-yl]-imidazo[1,2-a]pyridine-5-carboxylic acid methyl ester (9 mg) and lithium hydroxide (3 mg) were stirred in a 5 to 1 mixture of THF/Water (0.6 mL) at room temperature for 30 minutes before dilution with more water. The mixture was acidified to pH around 3 with a 10% aqueous solution of hydrochloric acid and extracted with EA. The organic layer was collected, dried over magnesium sulfate, filtered and concentrated under reduced pressure to give a residue used directly in the next amide coupling step.

Compound No 1.018 of Example 8 was prepared according to the following general reaction Scheme 7:

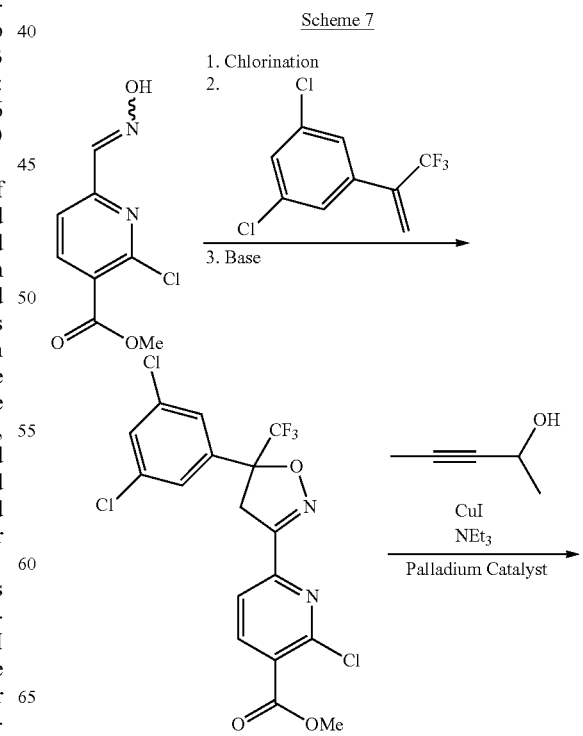

-continued

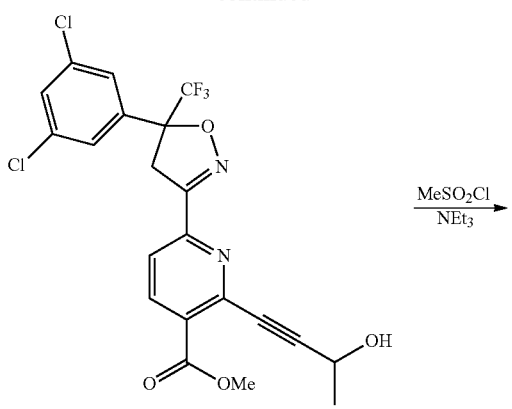

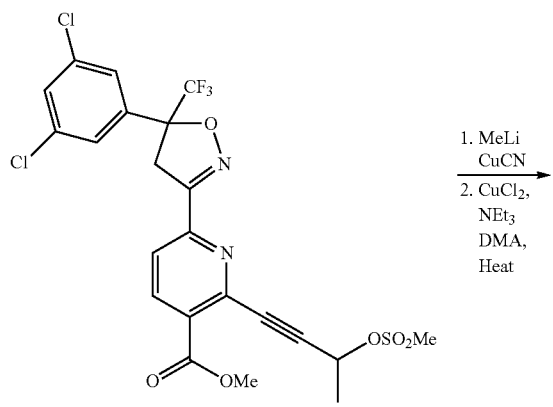

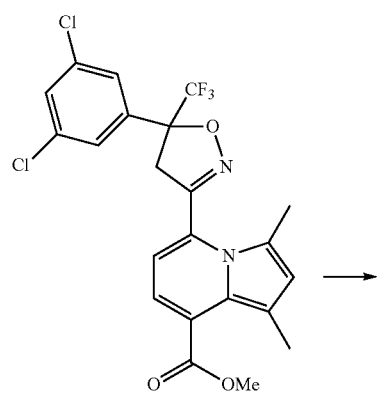

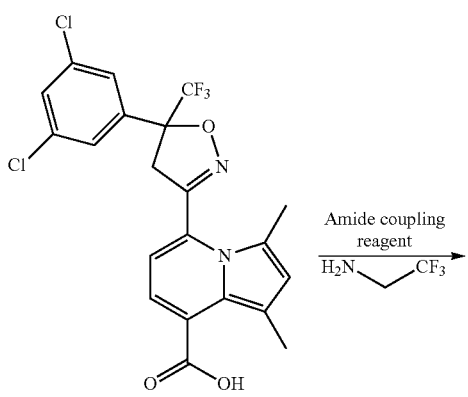

-continued

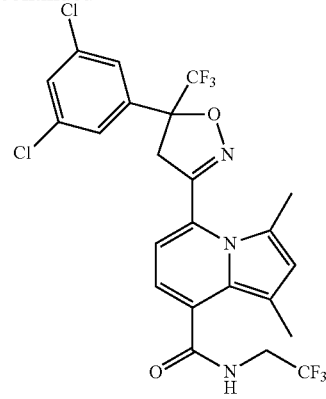

It will be apparent to one of skill in the art that the synthetic sequence depicted in Scheme 7 may be used to prepare additional compounds having different substituents by using the appropriate reagents. For example, compounds having different substituents on the phenyl ring may be prepared by using an alternative styrene derivatives having the desired substitution pattern and alternative amines or alcohols to obtain the desired amide or ester in the last step.

Example 8

5-[5-(3,5-Dichlorophenyl)-5-trifluoromethyl-4,5-dihydroisoxazol-3-yl]-1,3-dimethylindolizine-8-carboxylic acid (2,2,2-trifluoroethyl)-amide (compound No 1.018)

Using a procedure similar to that described in Example 1, except using 5-[5-(3,5-dichlorophenyl)-5-trifluoromethyl-4,5-dihydroisoxazol-3-yl]-1,3-dimethylindolizine-8-carboxylic acid (90 mg) and 2,2,2-trifluoroethylamine (38 mg), the title compound was isolated as a solid (85 mg, 81%). Rf=0.35 (3:7 EA/heptane). MS (ES): M/Z [M+H]=552. 1H NMR (400 MHz, DMSO-$d_6$): 2.18 (s, 3H), 2.19 (s, 3H), 4.11 (qd, J=9.7, 6.6 Hz, 2H), 4.48 (d, J=18.7 Hz, 1H), 4.56 (d, J=18.6 Hz, 1 H), 6.57 (s, 1H), 6.62 (d, J=7.0 Hz, 1H), 7.04 (d, J=7.0 Hz, 1H), 7.67 (d, J=1.7 Hz, 2H), 7.84 (t, J=1.9 Hz, 1H), 9.21 (t, J=6.3 Hz, 1H). 19F NMR (376 MHz, DMSO-$d_6$): −78.8 (s, 3F) and −70.6 (t, J=9.9Hz, 3 F)

The starting material, 5-[5-(3,5-dichlorophenyl)-5-trifluoromethyl-4,5-dihydroisoxazol-3-yl]-1,3-dimethylindolizine-8-carboxylic acid, was prepared as follows:

a. N-Chlorosuccinimide (1.6 g) was added to a solution of 2-chloro-6-(hydroxyiminomethyl)-nicotinic acid methyl ester (2.49 g, described in Example 1 a-d) in DMF (5 mL) and the mixture heated to 40° C. for 20 minutes. The mixture was cooled to around 0° C. (ice bath) and then 1,3-dichloro-5-(1-trifluoromethylvinyl)-benzene (3.1 g, prepared from commercially available 2-bromo-3,3,3-trifluoropropene and 3,5-dichlorophenylboronic acid by the method described in J. Fluorine. Chem. 1999, 95, 167-170) and TEA (1.8 mL) were added and the mixture stirred at room temperature overnight. The mixture was diluted with water and extracted with EA. The organic layer was collected, washed with brine, dried over sodium sulfate, filtered and concentrated under reduced pressure to give a residue that was purified by chromatography (SiO$_2$, Heptane/EA) to afford 2-chloro-6-[5-(3,5-dichlorophenyl)-5-trifluoromethyl-4,5-dihydroisoxazol-3-yl]-nicotinic acid methyl ester as a white solid (500 mg, 22% over 3 steps). Rf=0.35 (2:8 EA/heptane). 19F NMR (376 MHz, DMSO-$d_6$): −80.1 (s, 3F).

b. 2-Chloro-6-[5-(3,5-dichlorophenyl)-5-trifluoromethyl-4,5-dihydroisoxazol-3-yl]-nicotinic acid methyl ester (1.75 g), but-3-yn-2-ol (0.33 g), copper(I) iodide (40 mg) and bis(triphenylphosphine)palladiumchloride (0.13 g) in TEA (20 mL) were stirred heated to 50° C. for around 40 hours. The mixture was let cool to room temperature and concentrated under reduced pressure to give a residue that was diluted with EA. The mixture was filtered through a plug of Celite® and concentrated under reduced pressure to give a residue that was purified by chromatography (SiO$_2$, Heptane/EA) to afford 6-[5-(3,5-dichlorophenyl)-5-trifluoromethyl-4,5-dihydroisoxazol-3-yl]-2-(3-hydroxy-but-1-ynyl)-nicotinic acid methyl ester (0.5 g, 26%) along with recovered starting material 2-chloro-6-[5-(3,5-dichlorophenyl)-5-trifluoromethyl-4,5-dihydroisoxazol-3-yl]-nicotinic acid methyl ester (1.2 g, 69%). Rf=0.55 (1:1 EA/heptane).

c. To a solution of 6-[5-(3,5-dichlorophenyl)-5-trifluoromethyl-4,5-dihydroisoxazol-3-yl]-2-(3-hydroxy-but-1-ynyl)-nicotinic acid methyl ester (0.5 g) in THF (15 mL) cooled at at around −30° C. was added TEA (0.21 mL) followed by methanesulfonyl chloride (0.18 g). The mixture was let rise to room temperature and stirred for one hour. The mixture was filtered and filtrate concentrated under reduced pressure to give a residue that was purified by chromatography (SiO$_2$, Heptane/EA) to afford 6-[5-(3,5-dichlorophenyl)-5-trifluoromethyl-4,5-dihydroisoxazol-3-yl]-2-(3-methanesulfonyloxy-but-1-ynyl)-nicotinic acid methyl ester (0.6 g). Rf=0.7 (1:1 EA/heptane). 1H NMR (400 MHz, CHLOROFORM-d): 1.83 (d, J=6.7 Hz, 3H), 3.25 (br.s., 3 H), 3.88 (d, J=18.4 Hz, 1H), 3.98 (s, 3H), 4.27 (d, J=18.3 Hz, 1H), 5.62 (q, J=6.7 Hz, 1H), 7.44 (t, J=1.8 Hz, 1H), 7.52 (d, J=1.6 Hz, 2H), 8.08 (d, J=8.3 Hz, 1H) and 8.32 (d, J=8.3 Hz, 1H). 19F NMR (376 MHz, CHLOROFORM-d): −80.0 (s, 3F).

d. To a suspension of copper cyanide (0.14 g) in THF (15 mL) cooled at around −50° C. was added dropwise a solution of methyllithium in diethoxymethane (0.5 mL of a 3 molar solution from Aldrich). The mixture was let stirred 30 minutes prior to be cooled cooled at around −75° C. A solution of 6-[5-(3,5-dichlorophenyl)-5-trifluoromethyl-4,5-dihydroisoxazol-3-yl]-2-(3-methanesulfonyloxy-but-1-ynyl)-nicotinic acid methyl ester (0.54 g) in THF (7 mL) was added dropwise to the mixture that was let stirred at around −75° C. for 2 hours prior and then let rise to room temperature overnight. The mixture was quenched with a saturated solution of ammonium chloride, extracted with EA. The organic layer was collected, washed with brine, dried over sodium sulfate, filtered and concentrated under reduced pressure to give a residue that was purified by chromatography (SiO$_2$, Heptane/EA) to afford the allene intermediate (0.5 g). Rf=0.4 (2:8 EA/heptane). This residue was then dissolved in DMA (10 mL) and copper(II) chloride (50 mg) and TEA (0.75 mL) added to the mixture prior to heating to 130° C. for 5 hours under nitrogen. The mixture was cooled to room temperature and concentrated under reduced pressure to give a residue that was purified by chromatography (SiO$_2$, Heptane/EA) to afford 5-[5-(3,5-dichlorophenyl)-5-trifluoromethyl-4,5-dihydroisoxazol-3-yl]-1,3-dimethylindolizine-8-carboxylic acid methyl ester (0.3 g, 60%). Rf=0.35 (2:8 EA/heptane). 1H NMR (400 MHz, CHLOROFORM-d): 2.28 (s, 3H), 2.31 (s, 3H), 3.73 (d, J=17.8 Hz, 1H), 3.96 (s, 3H), 4.07 (d, J=17.7 Hz, 1H), 6.53 (s, 1H), 6.58 (d, J=7.0 Hz, 1H), 6.89 (d, J=7.0 Hz, 1H), 7.47 (t, J=1.8 Hz, 1H) and 7.51 (d, J=1.6 Hz, 2H). 19F NMR (376 MHz, CHLOROFORM-d): −79.5 (s, 3F).

e. To a solution of 5-[5-(3,5-dichlorophenyl)-5-trifluoromethyl-4,5-dihydroisoxazol-3-yl]-1,3-dimethylindolizine-8-carboxylic acid methyl ester (280 mg) in a 1 to 1 mixture of THF/MeOH (10 mL) was added a 1.5 molar aqueous solution of lithium hydroxide (1.5 mL) and the mixture stirred at room temperature overnight. The mixture was acidified to pH around 3 with a molar solution of hydrochloric acid and extracted with EA. The organic layer was collected, washed with brine, dried over sodium sulfate, filtered and concentrated under reduced pressure to give a solid (270 mg) used directly in the next amide coupling step. 1H NMR (400 MHz, CHLOROFORM-d) 2.29 (s, 3 H), 2.40 (s, 3H), 3.75 (d, J=17.8 Hz, 1H), 4.08 (d, J=17.8 Hz, 1H), 6.56 (s, 1H), 6.60 (d, J=7.1 Hz, 1H), 7.12 (d, J=7.1 Hz, 1H), 7.48 (t, J=1.8 Hz, 1H) and 7.52 (d, J=1.5 Hz, 2H). 19F NMR (376 MHz, CHLOROFORM-d): −79.5 (s, 3F).

Tables 1 and 2 below describe additional compounds of formula (I) prepared according to the general synthetic schemes and examples 1-6 described above.

TABLE 1

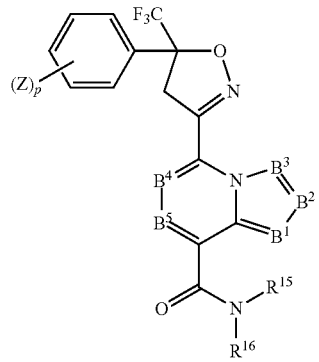

| Compound No. | $(Z)_p$ | $B^5$ | $B^4$ | $B^3$ | $B^2$ | $B^1$ | $R^{15}$ | $R^{16}$ | Ms MH+ | RT (min) | LCMS Method |
|---|---|---|---|---|---|---|---|---|---|---|---|
| 1.001 | 3,5-Cl$_2$ | C—H | C—H | C—H | C—H | N | H | CH$_2$C(O)NHCH$_2$CF$_3$ | 582 | 2.21 | 1 |
| 1.002 | 3,5-Cl$_2$ | C—H | C—H | C—H | C—H | N | H | CH$_2$CF$_3$ | 525 | 2.32 | 1 |
| 1.003 | 3,5-(CF$_3$)$_2$ | C—H | C—H | C—H | C—H | N | CH$_3$ | CH$_2$CO$_2$CH$_3$ | 597 | 2.06 | 1 |
| 1.004 | 3,5-(CF$_3$)$_2$ | C—H | C—H | C—H | C—H | N | CH$_3$ | CH$_2$CO$_2$H | 583 | 2.07 | 1 |

TABLE 1-continued

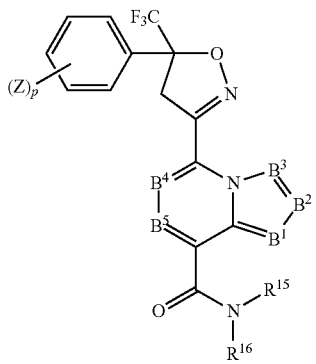

| Compound No. | $(Z)_p$ | $B^5$ | $B^4$ | $B^3$ | $B^2$ | $B^1$ | $R^{15}$ | $R^{16}$ | Ms $MH^+$ | RT (min) | LCMS Method |
|---|---|---|---|---|---|---|---|---|---|---|---|
| 1.005 | 3,5-$(CF_3)_2$ | C—H | C—H | C—H | C—H | N | $CH_3$ | $CH_2C(O)NHCH_2CF_3$ | 664 | 2.14 | 1 |
| 1.006 | 3,5-$(CF_3)_2$ | C—H | C—H | C—H | C—H | N | H | $CH_2C(O)NHCH_2CF_3$ | 650 | 2.18 | 1 |
| 1.007 | 3,5-$(CF_3)_2$ | C—H | C—H | C—H | C—H | N | H | $CH_2CH_2SCH_3$ | 585 | 2.31 | 1 |
| 1.008 | 3,5-$(CF_3)_2$ | C—H | C—H | C—H | C—H | C—H | H | $CH_2C(O)NHCH_2CF_3$ | 648 | 2.18 | 1 |
| 1.009 | 3,5-$(CF_3)_2$ | C—H | C—H | C—H | C—H | C—H | H | $CH_2CH_2SCH_3$ | 584 | 2.24 | 1 |
| 1.010 | 3,5-$(CF_3)_2$ | C—H | C—H | C—H | C—H | C—H | H | $CH_2CF_3$ | | | |
| 1.011 | 3,5-$Cl_2$ | C—H | C—H | C—H | C—H | C—H | H | $CH_2C(O)NHCH_2CF_3$ | 581 | 2.20 | 1 |
| 1.012 | 3,5-$Cl_2$ | C—H | C—H | C—H | C—H | C—H | H | $CH_2CF_3$ | | | |
| 1.013 | 3,5-$Cl_2$ | C—H | C—H | C—H | C—H | C—H | H | $CH_2CH_2SCH_3$ | 516 | 2.26 | 1 |
| 1.014 | 3-Cl,5-$CF_3$ | C—H | C—H | C—H | C—H | C—H | H | $CH_2C(O)NHCH_2CF_3$ | | | |
| 1.015 | 3-Cl,5-$CF_3$ | C—H | C—H | C—H | C—H | C—H | H | $CH_2CF_3$ | | | |
| 1.016 | 3-Cl,5-$CF_3$ | C—H | C—H | C—H | C—H | C—H | H | $CH_2CH_2SCH_3$ | | | |
| 1.017 | 3,5-$Cl_2$ | C—H | C—H | C—Me | C—H | C—Me | H | $CH_2C(O)NHCH_2CF_3$ | 609 | 2.12 | 1 |
| 1.018 | 3,5-$Cl_2$ | C—H | C—H | C—Me | C—H | C—Me | H | $CH_2CF_3$ | 552 | 2.17 | 1 |
| 1.019 | 3,5-$Cl_2$ | C—H | C—H | C—Me | C—H | C—Me | H | $CH_2CH_2SCH_3$ | 544 | 2.18 | 1 |
| 1.020 | 3,5-$(CF_3)_2$ | C—H | C—H | C—Me | C—H | C—Me | H | $CH_2C(O)NHCH_2CF_3$ | | | |
| 1.021 | 3,5-$(CF_3)_2$ | C—H | C—H | C—Me | C—H | C—Me | H | $CH_2CF_3$ | | | |
| 1.022 | 3,5-$(CF_3)_2$ | C—H | C—H | C—Me | C—H | C—Me | H | $CH_2CH_2SCH_3$ | | | |
| 1.023 | 3-Cl,5-$CF_3$ | C—H | C—H | C—Me | C—H | C—Me | H | $CH_2C(O)NHCH_2CF_3$ | | | |
| 1.024 | 3-Cl,5-$CF_3$ | C—H | C—H | C—Me | C—H | C—Me | H | $CH_2CF_3$ | | | |
| 1.025 | 3-Cl,5-$CF_3$ | C—H | C—H | C—Me | C—H | C—Me | H | $CH_2CH_2SCH_3$ | | | |

The numbers 1.001 to 1.025 are assigned to the above compounds in Table 1 for identification and reference hereinafter.

TABLE 2

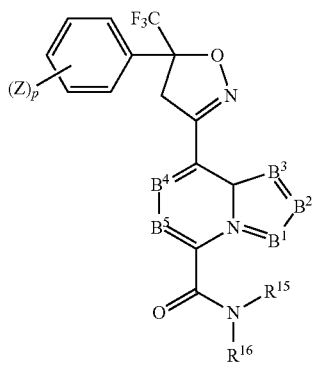

| Compound No. | $(Z)_p$ | $B^5$ | $B^4$ | $B^3$ | $B^2$ | $B^1$ | $R^{15}$ | $R^{16}$ | Ms $MH^+$ | RT Method | LCMS (min) |
|---|---|---|---|---|---|---|---|---|---|---|---|
| 2.001 | 3,5-$Cl_2$ | C—H | C—H | N | C—H | C—H | H | $CH_2C(O)NHCH_2CF_3$ | | | |
| 2.002 | 3,5-$Cl_2$ | C—H | C—H | N | C—H | C—H | H | $CH_2CF_3$ | | | |
| 2.003 | 3,5-$Cl_2$ | C—H | C—H | N | C—H | C—H | H | $CH_2CH_2SCH_3$ | | | |
| 2.004 | 3,5-$(CF_3)_2$ | C—H | C—H | N | C—H | C—H | H | $CH_2C(O)NHCH_2CF_3$ | 650 | 1.85 | 1 |
| 2.005 | 3,5-$(CF_3)_2$ | C—H | C—H | N | C—H | C—H | H | $CH_2CF_3$ | | | |
| 2.006 | 3,5-$(CF_3)_2$ | C—H | C—H | N | C—H | C—H | H | $CH_2CH_2SCH_3$ | | | |
| 2.007 | 3-Cl,5-$CF_3$ | C—H | C—H | N | C—H | C—H | H | $CH_2C(O)NHCH_2CF_3$ | | | |
| 2.008 | 3-Cl,5-$CF_3$ | C—H | C—H | N | C—H | C—H | H | $CH_2CF_3$ | | | |
| 2.009 | 3-Cl,5-$CF_3$ | C—H | C—H | N | C—H | C—H | H | $CH_2CH_2SCH_3$ | | | |
| 2.010 | 3,5-$Cl_2$ | C—H | C—H | C—H | C—H | C—H | H | $CH_2C(O)NHCH_2CF_3$ | | | |
| 2.011 | 3,5-$Cl_2$ | C—H | C—H | C—H | C—H | C—H | H | $CH_2CF_3$ | | | |

TABLE 2-continued

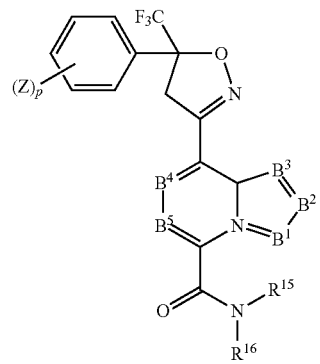

| Compound No. | (Z)$_p$ | B$^5$ | B$^4$ | B$^3$ | B$^2$ | B$^1$ | R$^{15}$ | R$^{16}$ | Ms MH+ | RT Method | LCMS (min) |
|---|---|---|---|---|---|---|---|---|---|---|---|
| 2.012 | 3,5-Cl$_2$ | C—H | C—H | C—H | C—H | C—H | H | CH$_2$CH$_2$SCH$_3$ | | | |
| 2.013 | 3,5-(CF$_3$)$_2$ | C—H | C—H | C—H | C—H | C—H | H | CH$_2$C(O)NHCH$_2$CF$_3$ | | | |
| 2.014 | 3,5-(CF$_3$)$_2$ | C—H | C—H | C—H | C—H | C—H | H | CH$_2$CF$_3$ | | | |
| 2.015 | 3,5-(CF$_3$)$_2$ | C—H | C—H | C—H | C—H | C—H | H | CH$_2$CH$_2$SCH$_3$ | | | |
| 2.016 | 3-Cl,5-CF$_3$ | C—H | C—H | C—H | C—H | C—H | H | CH$_2$C(O)NHCH$_2$CF$_3$ | | | |
| 2.017 | 3-Cl,5-CF$_3$ | C—H | C—H | C—H | C—H | C—H | H | CH$_2$CF$_3$ | | | |
| 2.018 | 3-Cl,5-CF$_3$ | C—H | C—H | C—H | C—H | C—H | H | CH$_2$CH$_2$SCH$_3$ | | | |

The numbers 2.001 to 2.018 are assigned to the above compounds for identification and reference hereinafter.

Biological Activity Against Parasites

METHOD A: Screening Method to Test Contact Activity of Compounds Against Ticks

A solution of the test compound was used to coat the inner wall of glass vials and to treat two filter papers. Once dried, one filter paper was placed in the cap of the vial and the other in the bottom of the vial. Each treated vial was infested with 10 adult *Rhipicephalus sanguineus* (Brown Dog Tick). Contact of the ticks with residues was induced by holding the vials in a controlled environment (24° C., 90-95% relative humidity) and assessment was performed at 24, 48 hours after application in comparison with untreated controls. Compounds numbers 1.008, 1.009, 1.011 and 1.013 gave at least 80% control of *Rhipicephalus sanguineus* at the 48 hour assessment at a test concentration of 200 ppm or less.

METHOD B: Screening Method to test Contact Activity of Compounds Against Fleas

A solution of the test compound was dispensed, using a pipette, onto filter paper placed into a glass vial. The filter paper was allowed to dry before infesting each vial with 10 adult *Ctenocephalides felis*. The treated *Ctenocephalides felis* were held in a controlled environment (24° C., 90-95% relative humidity) and assessment was performed at 24, 48 and 72 hours after application in comparison with untreated controls. Compounds numbers 1.009 gave at least 80% control at 72 hours assessment at a test concentration of 100 ppm or less.

METHOD C: Screening Method to Test Activity of Compounds Against Fleas Following Ingestion.

A cylindrical test container was filled with 10 adult *Ctenocephalides felis*. A cylindrical well was closed on one end with a self-sealing flexible film and placed on top of the test container in such a position that the fleas could pierce the film and feed on the contents of the cylinder. The test compound solution was then pipetted into bovine blood and added to the well. The container part with the *Ctenocepha-lides felis* was held at 20-22° C. and 40-60% relative humidity while the well part containing the treated blood was held at 37° C. and 40-60% relative humidity. Assessment was performed at 72 hours after application in comparison with untreated controls. Compounds numbers 1.001, 1.003, 1.005, 1.006, 1.007, 1.008, 1.009, 1.011 and 1.013 gave at least 80% control at a test concentration of 50 ppm or less.

METHOD D: Screening Method to Test Contact Activity of Compounds Against Stable Flies.

A solution of the test compound was used to treat a filter paper contained within a Petri dish and the filter paper was allowed to evaporate to dryness. A small piece of absorbent cotton moistened with 10% sucrose and ten adult flies (*Stomoxys calcitrans*) were added to each dish. Dishes were capped and held at room temperature. Assessments were performed at 24 hours after infestation in comparison with untreated controls. Compound number 1.013 gave at least 80% control at a test concentration of 5 µg/cm2 or less.

METHOD E: Screening Method to Test Activity of Compounds Against Microfilaria of *Dirofilaria immitis*.

Four hundred to six hundred microfilaria of *Dirofilaria immitis* were added to wells of a microtitre plate containing RPMI-1640 media (Fisher Scientific) and the test compound in DMSO. The microtitre plate was then held at 37° C. in an environment containing 5% CO$_2$. An assessment was conducted at 5 days to determine survival of the microfilaria. Microfilaria exposed to DMSO and no test compound served as controls. Compounds numbers 1.001 and 1.005 gave at least 60% motility inhibition at a test concentration of 5 ppm or less.

The invention is further described by the following numbered paragraphs:

1. A dihydroazole compound of formula (I), or a pharmaceutically acceptable salt thereof:

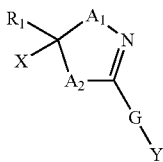

(I)

wherein:

$R_1$ is hydrogen, halogen, —CN, or alkyl, haloalkyl, alkenyl, haloalkenyl, alkynyl, haloalkynyl, cycloalkyl, halocycloalkyl, alkylcycloalkyl or cycloalkylalkyl, each which is unsubstituted or substituted with one or more of halogen, hydroxy, amino, alkyl- or di(alkyl)amino, alkyl, cycloalkyl, haloalkyl, alkenyl, haloalkenyl, alkynyl, haloalkynyl, alkoxy, haloalkoxy, alkylthio, haloalkylthio, $R_7S(O)$—, $R_7S(O)_2$—, $R_7C(O)$—, $R_7R_8NC(O)$—, $R_7OC(O)$—, $R_7C(O)O$—, $R_7C(O)NR_8$—, —CN or —NO$_2$;

X is aryl or heteroaryl, which may be unsubstituted or substituted by one or more of halogen, hydroxy, amino, alkyl- or di(alkyl)amino, alkyl, cycloalkyl, haloalkyl, alkenyl, haloalkenyl, alkynyl, haloalkynyl, alkoxy, haloalkoxy, alkylthio, haloalkylthio, $R_7S(O)$—, $R_7S(O)_2$—, $R_7C(O)$—, $R_7R_8NC(O)$—, $R_7OC(O)$—, $R_7C(O)O$—, $R_7C(O)NR_8$—, —CN or —NO$_2$;

$A_1$ and $A_2$ are independently oxygen, $NR_2$ or $CR_7R_8$;

G is G-1 or G-2;

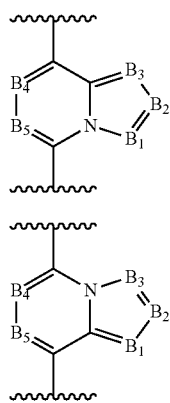

G-1

G-2

$B_1$, $B_2$, $B_3$, $B_4$ and $B_5$ are independently N or C—$R_9$;

Y is hydrogen, halogen, —CN; or Y is alkyl, haloalkyl, alkenyl, haloalkenyl, alkynyl, haloalkynyl, cycloalkyl, alkylcycloalkyl, cycloalkylalkyl, aryl, or heterocyclyl or heteroaryl each of which is unsubstituted or substituted with one or more of halogen, hydroxy, amino, alkyl- or di(alkyl)amino, alkyl, cycloalkyl, haloalkyl, alkenyl, haloalkenyl, alkynyl, haloalkynyl, alkoxy, haloalkoxy, alkylthio, haloalkylthio, $R_7S(O)$—, $R_7S(O)_2$—, $R_7C(O)$—, $R_7R_8NC(O)$—, $R_7OC(O)$—, $R_7C(O)O$—, $R_7C(O)NR_8$—, —CN or —NO$_2$; or Y is Y-1, Y-2, Y-3, Y-4, Y-5, Y-6, Y-7, Y-8, Y-9, Y-10, Y-11, Y-12 or Y-13;

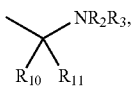

Y-1

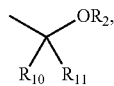

Y-2

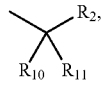

Y-3

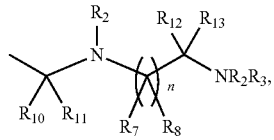

Y-4

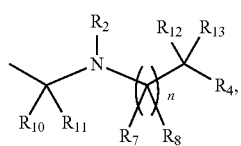

Y-5

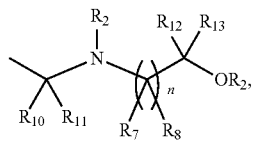

Y-6

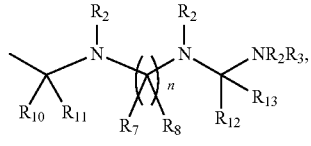

Y-7

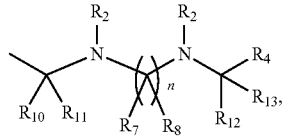

Y-8

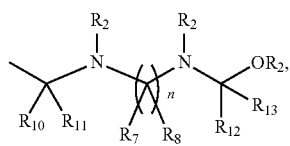

Y-9

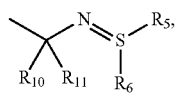

Y-10

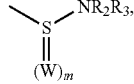

Y-11

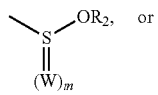

Y-12 or

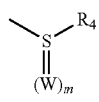

Y-13

$R_2$, $R_3$ are independently hydrogen, alkyl, haloalkyl, thioalkyl, alkylthioalkyl, hydroxyalkyl, alkoxylakyl, alkenyl, haloalkenyl, alkynyl, haloalkynyl, cycloalkyl, $R_{10}S(O)-$, $R_{10}S(O)_2-$, $R_{10}C(O)-$, $R_{10}C(S)-$, $R_{10}R_{11}NC(O)-$, $R_{10}R_{11}NC(S)-R_{10}OC(O)-$;

$R_4$, $R_5$ and $R_6$ are independently hydrogen, alkyl, haloalkyl, thioalkyl, alkylthioalkyl, hydroxyalkyl, alkoxylakyl, alkenyl, haloalkenyl, alkynyl, haloalkynyl, cycloalkyl, aryl or heteroaryl;

$R_7$ and $R_8$ are independently hydrogen, alkyl, haloalkyl, thioalkyl, alkylthioalkyl, hydroxyalkyl, alkoxylakyl, alkenyl, haloalkenyl, alkynyl or haloalkynyl;

$R_9$ is hydrogen, halogen, —CN, or alkyl, haloalkyl, alkenyl, haloalkenyl, alkynyl, haloalkynyl, cycloalkyl, halocycloalkyl, alkylcycloalkyl or cycloalkylalkyl, each which is unsubstituted or substituted with one or more of halogen, hydroxy, amino, alkyl- or di(alkyl)amino, alkyl, cycloalkyl, haloalkyl, alkenyl, haloalkenyl, alkynyl, haloalkynyl, alkoxy, haloalkoxy, alkylthio, haloalkylthio, $R_7S(O)-$, $R_7S(O)_2-$, $R_7C(O)-$, $R_7R_8NC(O)-$, $R_7OC(O)-$, $R_7C(O)O-$, $R_7C(O)NR_8-$, —CN or —$NO_2$;

$R_{10}$, $R_{11}$, $R_{12}$ and $R_{13}$ are each independently hydrogen, alkyl, haloalkyl, thioalkyl, alkylthioalkyl, hydroxyalkyl, alkoxylakyl, alkenyl, haloalkenyl, alkynyl or haloalkynyl; or $R_{10}$ together with $R_{11}$ form =O, =S or =$NR_2$; or
$R_{12}$ together with $R_{13}$ form =O, =S or =$NR_2$;
W is O, S or $NR_2$;
n is 1-4; and
m is 0, 1 or 2.

2. The compound of paragraph 1, wherein G is G-1.
3. The compound of paragraph 1, wherein G is G-2.
4. The compound of paragraph 1, wherein:
G is G-1;
$A_1$ is oxygen; and
X is optionally substituted aryl.
5. The compound of paragraph 1, wherein:
G is G-2;
$A_1$ is oxygen; and
X is optionally substituted aryl.
6. The compound of paragraph 1, wherein:
$A_1$ is oxygen;
X is optionally substituted aryl;
$R_1$ is hydrogen, halogen, alkyl or haloalkyl; and
Y is Y-1, Y-2, Y-3, Y-4, Y-5, Y-6, Y-7, Y-8, Y-9, Y-10, Y-11, Y-12 or Y-13.
7. The compound of paragraph 1, wherein:
$A_1$ is oxygen;
X is optionally substituted aryl;
$R_1$ is hydrogen, halogen, alkyl or haloalkyl; and
Y is pyrazolyl or triazolyl.
8. The compound of paragraph 1, wherein:
G is G-1;
$B_1$, $B_2$, $B_3$, $B_4$ and $B_5$ are each C—$R_9$;
$R_1$ is $C_1$-$C_4$alkyl or $C_1$-$C_4$haloalkyl;
X is phenyl, which may be unsubstituted or substituted by one or more halogen, $C_1$-$C_4$alkyl or $C_1$-$C_4$haloalkyl;
$A_1$ is oxygen;
$A_2$ is $CR_7R_8$;
Y is Y-1, Y-4, Y-5, Y-6;
$R_2$ and $R_4$ are independently hydrogen, $C_1$-$C_4$alkyl, $C_1$-$C_4$haloalkyl, $C_1$-$C_4$akoxy-$C_1$-$C_4$alkyl or $C_1$-$C_4$alkylthio-$C_1$-$C_4$alkyl; and
$R_3$, and $R_9$ are independently hydrogen, $C_1$-$C_4$alkyl or $C_1$-$C_4$haloalkyl.
9. The compound of paragraph 1, wherein:
G is G-2;
$B_1$, $B_2$, $B_3$, $B_4$ and $B_5$ are each C—$R_9$;
$R_1$ is $C_1$-$C_4$alkyl or $C_1$-$C_4$haloalkyl;
X is phenyl, which may be unsubstituted or substituted by one or more halogen, $C_1$-$C_4$alkyl or $C_1$-$C_4$haloalkyl;
$A_1$ is oxygen;
$A_2$ is $CR_7R_8$;
Y is Y-1, Y-4, Y-5, Y-6;
$R_2$ and $R_4$ are independently hydrogen, $C_1$-$C_4$alkyl, $C_1$-$C_4$haloalkyl, $C_1$-$C_4$akoxy-$C_1$-$C_4$alkyl or $C_1$-$C_4$alkylthio-$C_1$-$C_4$alkyl; and
$R_3$, and $R_9$ are independently hydrogen, $C_1$-$C_4$alkyl or $C_1$-$C_4$haloalkyl.
10. The compound of paragraph 1, wherein:
G is G-1;
$B_1$, $B_2$, $B_4$ and $B_5$ are each C—$R_9$;
$B_3$ is N;
$R_1$ is $C_1$-$C_4$alkyl or $C_1$-$C_4$haloalkyl;
X is phenyl, which may be unsubstituted or substituted by one or more halogen, $C_1$-$C_4$alkyl or $C_1$-$C_4$haloalkyl;
$A_1$ is oxygen;
$A_2$ is $CR_7R_8$;
Y is Y-1, Y-4, Y-5, Y-6;
$R_2$ and $R_4$ are independently hydrogen, $C_1$-$C_4$alkyl, $C_1$-$C_4$haloalkyl, $C_1$-$C_4$akoxy-$C_1$-$C_4$alkyl or $C_1$-$C_4$alkylthio-$C_1$-$C_4$alkyl; and
$R_3$, and $R_9$ are independently hydrogen, $C_1$-$C_4$alkyl or $C_1$-$C_4$haloalkyl.
11. The compound of paragraph 1, wherein:
G is G-2;
$B_2$, $B_3$, $B_4$ and $B_5$ are each C—$R_9$;
$B_1$ is N;
$R_1$ is $C_1$-$C_4$alkyl or $C_1$-$C_4$haloalkyl;
X is phenyl, which may be unsubstituted or substituted by one or more halogen, $C_1$-$C_4$alkyl or $C_1$-$C_4$haloalkyl;
$A_1$ is oxygen;
$A_2$ is $CR_7R_8$;
Y is Y-1, Y-4, Y-5, Y-6;
$R_2$ and $R_4$ are independently hydrogen, $C_1$-$C_4$alkyl, $C_1$-$C_4$haloalkyl, $C_1$-$C_4$akoxy-$C_1$-$C_4$alkyl or $C_1$-$C_4$alkylthio-$C_1$-$C_4$alkyl; and
$R_3$, and $R_9$ are independently hydrogen, $C_1$-$C_4$alkyl or $C_1$-$C_4$haloalkyl.
12. The compound of paragraph 8, wherein:
$A_2$ is $CH_2$;
$R_9$ is hydrogen;
$R_{12}$ together with $R_{13}$ form =O, =S or =$NR_2$;
$R_2$ and $R_4$ are independently hydrogen, $C_1$-$C_4$alkyl, $C_1$-$C_4$haloalkyl; and
$R_3$, $R_7$ and $R_8$ are each hydrogen.
13. The compound of paragraph 9, wherein:
$A_2$ is $CH_2$;
$R_9$ is hydrogen;
$R_{12}$ together with $R_{13}$ form =O, =S or =$NR_2$;
$R_2$ and $R_4$ are independently hydrogen, $C_1$-$C_4$alkyl, $C_1$-$C_4$haloalkyl; and
$R_3$, $R_7$ and $R_8$ are each hydrogen.
14. The compound of paragraph 8, wherein:
$A_2$ is $CH_2$;
$R_9$ is hydrogen;
$R_{10}$ together with $R_{11}$ form =O, =S or =$NR_2$;
$R_2$ and $R_4$ are independently hydrogen, $C_1$-$C_4$alkyl, $C_1$-$C_4$haloalkyl; and
$R_3$, $R_7$ and $R_8$ are each hydrogen.
15. The compound of paragraph 9, wherein:
$A_2$ 1S $CH_2$;
$R_9$ is hydrogen;
$R_{10}$ together with $R_{11}$ form =O, =S or =$NR_2$;

$R_2$ and $R_4$ are independently hydrogen, $C_1$-$C_4$alkyl, $C_1$-$C_4$haloalkyl; and
$R_3$, $R_7$ and $R_8$ are each hydrogen.

16. The compound of paragraph 8, wherein:
$A_2$ is $CH_2$;
$R_9$ is hydrogen;
$R_{10}$ together with $R_{11}$ form =O, =S or =$NR_2$;
$R_{12}$ together with $R_{13}$ form =O, =S or =$NR_2$;
$R_2$ and $R_4$ are independently hydrogen, $C_1$-$C_4$alkyl or $C_1$-$C_4$haloalkyl; and
$R_3$, $R_7$ and $R_8$ are hydrogen.

17. The compound of paragraph 10, wherein:
$A_2$ is $CH_2$;
$R_9$ is hydrogen;
$R_{12}$ together with $R_{13}$ form =O, =S or =$NR_2$;
$R_2$ and $R_4$ are independently hydrogen, $C_1$-$C_4$alkyl, $C_1$-$C_4$haloalkyl; and $R_3$, $R_7$ and $R_8$ are each hydrogen.

18. The compound of paragraph 11, wherein:
$A_2$ is $CH_2$;
$R_9$ is hydrogen;
$R_{12}$ together with $R_{13}$ form =O, =S or =$NR_2$;
$R_2$ and $R_4$ are independently hydrogen, $C_1$-$C_4$alkyl, $C_1$-$C_4$haloalkyl; and
$R_3$, $R_7$ and $R_8$ are each hydrogen.

19. The compound of paragraph 10, wherein:
$A_2$ is $CH_2$;
$R_9$ is hydrogen;
$R_{10}$ together with $R_{11}$ form =O, =S or =$NR_2$;
$R_2$ and $R_4$ are independently hydrogen, $C_1$-$C_4$alkyl, $C_1$-$C_4$haloalkyl; and
$R_3$, $R_7$ and $R_8$ are each hydrogen.

20. The compound of paragraph 11, wherein:
$A_2$ is $CH_2$;
$R_9$ is hydrogen;
$R_{10}$ together with $R_{11}$ form =O, =S or =$NR_2$;
$R_2$ and $R_4$ are independently hydrogen, $C_1$-$C_4$alkyl, $C_1$-$C_4$haloalkyl; and
$R_3$, $R_7$ and $R_8$ are each hydrogen.

21. The compound of paragraph 10, wherein:
$A_2$ is $CH_2$;
$R_9$ is hydrogen;
$R_{10}$ together with $R_{11}$ form =O, =S or =$NR_2$;
$R_{12}$ together with $R_{13}$ form =O, =S or =$NR_2$;
$R_2$ and $R_4$ are independently hydrogen, $C_1$-$C_4$alkyl or $C_1$-$C_4$haloalkyl; and
$R_3$, $R_7$ and $R_8$ are hydrogen.

22. The compound of paragraph 11, wherein:
$A_2$ is $CH_2$;
$R_9$ is hydrogen;
$R_{10}$ together with $R_{11}$ form =O, =S or =$NR_2$;
$R_{12}$ together with $R_{13}$ form =O, =S or =$NR_2$;
$R_2$ and $R_4$ are independently hydrogen, $C_1$-$C_4$alkyl or $C_1$-$C_4$haloalkyl; and
$R_3$, $R_7$ and $R_8$ are hydrogen.

23. A composition for the treatment or prevention of a parasitic infection or infestation in an animal comprising an effective amount of a compound of paragraph 1 in combination with a pharmaceutically acceptable carrier.

24. A method for the treatment or prevention of a parasitic infection or infestation in an animal, comprising administering to the animal an effective amount of a compound of paragraph 1 to the animal.

25. Use of the compound of paragraph 1 in the treatment or prevention of a parasitic infection or infestation in an animal.

26. Use of the compound of paragraph 1 in the manufacture of a medicament for the treatment or prevention of a parasitic infection or infestation in an animal.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. An injectable antiparasitic composition for the treatment of a parasitic infestation or infection in an animal comprising:
(a) an effective amount of a dihydroazole compound of formula (I), or a pharmaceutically or agriculturally acceptable salt thereof:

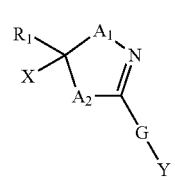

(I)

wherein:
$R_1$ is hydrogen, halogen, —CN, or alkyl, haloalkyl, alkenyl, haloalkenyl, alkynyl, haloalkynyl, cycloalkyl, halocycloalkyl, alkylcycloalkyl or cycloalkylalkyl, each which is unsubstituted or substituted with one or more of halogen, hydroxy, amino, alkyl- or di(alkyl)amino, alkyl, cycloalkyl, haloalkyl, alkenyl, haloalkenyl, alkynyl, haloalkynyl, alkoxy, haloalkoxy, alkylthio, haloalkylthio, $R_7S(O)$—, $R_7S(O)_2$—, $R_7C(O)$—, $R_7R_8NC(O)$—, $R_7OC(O)$—, $R_7C(O)O$—, $R_7C(O)NR_8$—, —CN or —$NO_2$;

X is aryl or heteroaryl, which may be unsubstituted or substituted by one or more of halogen, hydroxy, amino, alkyl- or di(alkyl)amino, alkyl, cycloalkyl, haloalkyl, alkenyl, haloalkenyl, alkynyl, haloalkynyl, alkoxy, haloalkoxy, alkylthio, haloalkylthio, $R_7S(O)$—, $R_7S(O)_2$—, $R_7C(O)$—, $R_7R_8NC(O)$—, $R_7OC(O)$—, $R_7C(O)O$—, $R_7C(O)NR_8$—, —CN or —$NO_2$;

$A_1$ is oxygen;
$A_2$ is oxygen, $NR_2$ or $CR_7R_8$;
G is G-1 or G-2;

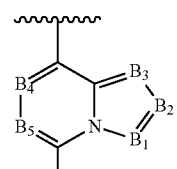

G-1

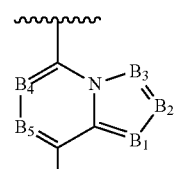

G-2

$B_1$, $B_2$, $B_3$, $B_4$ and $B_5$ are independently N or C—$R_9$;

Y is hydrogen, halogen, —CN; or Y is alkyl, haloalkyl, alkenyl, haloalkenyl, alkynyl, haloalkynyl, cycloalkyl, alkylcycloalkyl, cycloalkylalkyl, aryl, or heterocyclyl or heteroaryl each of which is unsubstituted or substituted with one or more of halogen, hydroxy, amino, alkyl- or di(alkyl)amino, alkyl, cycloalkyl, haloalkyl, alkenyl, haloalkenyl, alkynyl, haloalkynyl, alkoxy, haloalkoxy, alkylthio, haloalkylthio, $R_7S(O)$—, $R_7S(O)_2$—, $R_7C(O)$—, $R_7R_8NC(O)$—, $R_7OC(O)$—, $R_7C(O)O$—, $R_7C(O)NR_8$—, —CN or —NO_2; or Y is Y-1, Y-2, Y-3, Y-4, Y-5, Y-6, Y-7, Y-8, Y-9, Y-10, Y-11, Y-12 or Y-13;

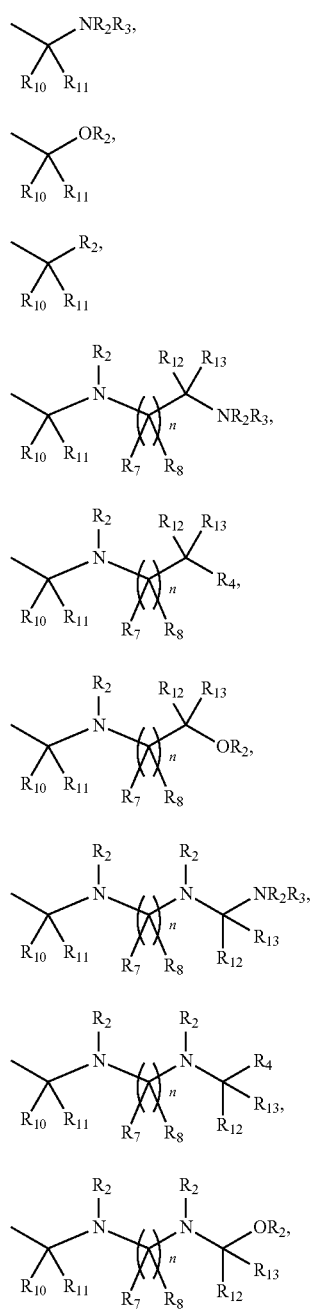

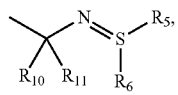

Y-10

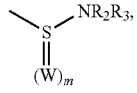

Y-11

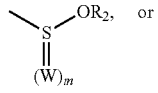

Y-12

Y-13

$R_2$, $R_3$ are independently hydrogen, alkyl, haloalkyl, thioalkyl, alkylthioalkyl, hydroxyalkyl, alkoxylakyl, alkenyl, haloalkenyl, alkynyl, haloalkynyl, cycloalkyl, $R_{10}S(O)$—, $R_{10}S(O)_2$—, $R_{10}C(O)$—, $R_{10}C(S)$—, $R_{10}R_{11}NC(O)$—, $R_{10}R_{11}NC(S)$—$R_{10}OC(O)$—;

$R_4$, $R_5$ and $R_6$ are independently hydrogen, alkyl, haloalkyl, thioalkyl, alkylthioalkyl, hydroxyalkyl, alkoxylakyl, alkenyl, haloalkenyl, alkynyl, haloalkynyl, cycloalkyl, aryl or heteroaryl;

$R_7$ and $R_8$ are independently hydrogen, alkyl, haloalkyl, thioalkyl, alkylthioalkyl, hydroxyalkyl, alkoxylakyl, alkenyl, haloalkenyl, alkynyl or haloalkynyl;

$R_9$ is is hydrogen, halogen, —CN, or alkyl, haloalkyl, alkenyl, haloalkenyl, alkynyl, haloalkynyl, cycloalkyl, halocycloalkyl, alkylcycloalkyl or cycloalkylalkyl, each which is unsubstituted or substituted with one or more of halogen, hydroxy, amino, alkyl- or di(alkyl)amino, alkyl, cycloalkyl, haloalkyl, alkenyl, haloalkenyl, alkynyl, haloalkynyl, alkoxy, haloalkoxy, alkylthio, haloalkylthio, $R_7S(O)$—, $R_7S(O)_2$—, $R_7C(O)$—, $R_7R_8NC(O)$—, $R_7OC(O)$—, $R_7C(O)O$—, $R_7C(O)NR_8$—, —CN or —NO_2;

$R_{10}$, $R_{11}$, $R_{12}$ and $R_{13}$ are each independently hydrogen, alkyl, haloalkyl, thioalkyl, alkylthioalkyl, hydroxyalkyl, alkoxylakyl, alkenyl, haloalkenyl, alkynyl or haloalkynyl; or $R_{10}$ together with $R_{11}$ form =O, =S or =NR_2; or
$R_{12}$ together with $R_{13}$ form =O, =S or =NR_2;
W is O, S or NR_2;
n is 1-4; and
m is 0, 1 or 2; and
(b) a pharmaceutically acceptable carrier.

2. The composition of claim 1, wherein G is G-1.

3. The composition of claim 1, wherein G is G-2.

4. The composition of claim 1, wherein:
G is G-1;
and
X is optionally substituted aryl.

5. The composition of claim 1, wherein:
G is G-2;
and
X is optionally substituted aryl.

6. The composition of claim 1, wherein:
X is optionally substituted aryl;
$R_1$ is hydrogen, halogen, alkyl or haloalkyl; and
Y is Y-1, Y-2, Y-3, Y-4, Y-5, Y-6, Y-7, Y-8, Y-9, Y-10, Y-11, Y-12 or Y-13.

7. The composition of claim 1, wherein:
X is optionally substituted aryl;
$R_1$ is hydrogen, halogen, alkyl or haloalkyl; and
Y is Y 1, Y-4, Y-5 or Y-6.

8. The composition of claim 1, wherein:
G is G-1;
$B_1$, $B_2$, $B_3$, $B_4$ and $B_5$ are each C—$R_9$;
$R_1$ is $C_1$-$C_4$alkyl or $C_1$-$C_4$haloalkyl;
X is phenyl, which may be unsubstituted or substituted by one or more halogen, $C_1$-$C_4$alkyl or $C_1$-$C_4$haloalkyl;
$A_2$ is $CR_7R_8$;
Y is Y-1, Y-4, Y-5, Y-6;
$R_3$ and $R_4$ are independently hydrogen, $C_1$-$C_4$alkyl, $C_1$-$C_4$haloalkyl, $C_1$-$C_4$akoxy-$C_1$-$C_4$alkyl or $C_1$-$C_4$alkylthio-$C_1$-$C_4$alkyl; and
$R_2$, and $R_9$ are independently hydrogen, $C_1$-$C_4$alkyl or $C_1$-$C_4$haloalkyl.

9. The composition of claim 1, wherein:
G is G-2;
$B_1$, $B_2$, $B_3$, $B_4$ and $B_5$ are each C—$R_9$;
$R_1$ is $C_1$-$C_4$alkyl or $C_1$-$C_4$haloalkyl;
X is phenyl, which may be unsubstituted or substituted by one or more halogen, $C_1$-$C_4$alkyl or $C_1$-$C_4$haloalkyl;
$A_2$ is $CR_7R_8$;
Y is Y-1, Y-4, Y-5, Y-6;
$R_3$ and $R_4$ are independently hydrogen, $C_1$-$C_4$alkyl, $C_1$-$C_4$haloalkyl, $C_1$-$C_4$akoxy-C-$C_4$alkyl or $C_1$-$C_4$alkylthio-$C_1$-$C_4$alkyl; and
$R_2$, and $R_9$ are independently hydrogen, $C_1$-$C_4$alkyl or C-$C_4$haloalkyl.

10. The composition of claim 1, wherein:
G is G-1;
$B_1$, $B_2$, $B_4$ and $B_5$ are each C—$R_9$;
$B_3$ is N;
$R_1$ is $C_1$-$C_4$alkyl or $C_1$-$C_4$haloalkyl;
X is phenyl, which may be unsubstituted or substituted by one or more halogen, $C_1$-$C_4$alkyl or $C_1$-$C_4$haloalkyl;
$A_2$ is $CR_7R_8$;
Y is Y-1, Y-4, Y-5, Y-6;
$R_3$ and $R_4$ are independently hydrogen, $C_1$-$C_4$alkyl, $C_1$-$C_4$haloalkyl, $C_1$-$C_4$akoxy-$C_1$-$C_4$alkyl or $C_1$-$C_4$alkylthio-$C_1$-$C_4$alkyl; and
$R_2$, and $R_9$ are independently hydrogen, $C_1$-$C_4$alkyl or $C_1$-$C_4$haloalkyl.

11. The composition of claim 1, wherein:
G is G-2;
$B_2$, $B_3$, $B_4$ and $B_5$ are each C—$R_9$;
$B_1$ is N;
$R_1$ is $C_1$-$C_4$alkyl or $C_1$-$C_4$haloalkyl;
X is phenyl, which may be unsubstituted or substituted by one or more halogen, $C_1$-$C_4$alkyl or $C_1$-$C_4$haloalkyl;
$A_2$ is $CR_7R_8$;
Y is Y-1, Y-4, Y-5, Y-6;
$R_3$ and $R_4$ are independently hydrogen, $C_1$-$C_4$alkyl, $C_1$-$C_4$haloalkyl, $C_1$-$C_4$akoxy-$C_1$-$C_4$alkyl or $C_1$-$C_4$alkylthio-$C_1$-$C_4$alkyl; and
$R_2$, and $R_9$ are independently hydrogen, $C_1$-$C_4$alkyl or $C_1$-$C_4$haloalkyl.

12. The composition of claim 8, wherein:
$A_2$ is $CH_2$;
$R_9$ is hydrogen;
$R_{10}$ together with $R_{11}$ form =O, =S or =$NR_2$;
$R_3$ is hydrogen, $C_1$-$C_4$alkyl, $C_1$-$C_4$haloalkyl or $C_1$-$C_4$alkylthio-$C_1$-$C_4$alkyl; and
$R_2$, $R_7$ and $R_8$ are each hydrogen.

13. The composition of claim 9, wherein:
$R_9$ is hydrogen;
$R_{10}$ together with $R_{11}$ form =O, =S or =$NR_2$;
$R_3$ is hydrogen, $C_1$-$C_4$alkyl, $C_1$-$C_4$haloalkyl or $C_1$-$C_4$alkylthio-$C_1$-$C_4$alkyl; and
$R_2$, $R_7$ and $R_8$ are each hydrogen; and
Y is Y-1 or Y-4.

14. The composition of claim 8, wherein:
$A_2$ is $CH_2$;
$R_9$ is hydrogen;
$R_{10}$ together with $R_{11}$ form =O, =S or =$NR_2$;
$R_{12}$ together with $R_{13}$ form =O, =S or =$NR_2$;
$R_3$ is hydrogen, $C_1$-$C_4$alkyl, $C_1$-$C_4$haloalkyl or $C_1$-$C_4$alkylthio-$C_1$-$C_4$alkyl;
$R_2$, $R_7$ and $R_8$ are each hydrogen; and
Y is Y-1 or Y-4.

15. The composition of claim 9, wherein:
$A_2$ is $CH_2$;
$R_9$ is hydrogen;
$R_{10}$ together with $R_{11}$ form =O, =S or =$NR_2$;
$R_{12}$ together with $R_{13}$ form =O, =S or =$NR_2$;
$R_3$ is hydrogen, $C_1$-$C_4$alkyl, $C_1$-$C_4$haloalkyl or $C_1$-$C_4$alkylthio-$C_1$-$C_4$alkyl;
$R_2$, $R_7$ and $R_8$ are each hydrogen; and
Y is Y-1 or Y-4.

16. The composition of claim 8, wherein:
$A_2$ is $CH_2$;
$R_9$ is hydrogen;
$R_{10}$ together with $R_{11}$ form =O;
$R_{12}$ together with $R_{13}$ form =O;
$R_3$ is hydrogen, $C_1$-$C_4$alkyl or $C_1$-$C_4$haloalkyl or $C_1$-$C_4$alkylthio-$C_1$-$C_4$alkyl;
$R_2$, $R_7$ and $R_8$ are hydrogen; and
Y is Y-1 or Y-4.

17. The composition of claim 10, wherein:
$A_2$ is $CH_2$;
$R_9$ is hydrogen;
$R_{10}$ together with $R_{11}$ form =O, =S or =$NR_2$;
$R_3$ is hydrogen, $C_1$-$C_4$alkyl, $C_1$-$C_4$haloalkyl or $C_1$-$C_4$alkylthio-$C_1$-$C_4$alkyl;
$R_2$, $R_7$ and $R_8$ are each hydrogen; and
Y is Y-1 or Y-4.

18. The composition of claim 11, wherein:
$A_2$ is $CH_2$;
$R_9$ is hydrogen;
$R_{10}$ together with $R_{11}$ form =O, =S or =$NR_2$;
$R_3$ is hydrogen, $C_1$-$C_4$alkyl, $C_1$-$C_4$haloalkyl or $C_1$-$C_4$alkylthio-$C_1$-$C_4$alkyl;
$R_2$, $R_7$ and $R_8$ are each hydrogen; and
Y is Y-1 or Y-4.

19. The composition of claim 10, wherein:
$A_2$ is $CH_2$;
$R_9$ is hydrogen;
$R_{10}$ together with $R_{11}$ form =O, =S or =$NR_2$;
$R_{12}$ together with $R_{13}$ form =O, =S or =$NR_2$;
$R_3$ is hydrogen, $C_1$-$C_4$alkyl, $C_1$-$C_4$haloalkyl or $C_1$-$C_4$alkylthio-$C_1$-$C_4$alkyl;
$R_2$, $R_7$ and $R_8$ are each hydrogen; and
Y is Y-1 or Y-4.

20. The composition of claim 11, wherein:
$A_2$ is $CH_2$;
$R_9$ is hydrogen;
$R_{10}$ together with $R_{11}$ form =O, =S or =$NR_2$;
$R_{12}$ together with $R_{13}$ form =O, =S or =$NR_2$;
$R_3$ is hydrogen, $C_1$-$C_4$alkyl, $C_1$-$C_4$haloalkyl or $C_1$-$C_4$alkylthio-$C_1$-$C_4$alkyl;
$R_2$, $R_7$ and $R_8$ are each hydrogen; and
Y is Y-1 or Y-4.

21. The composition of claim 10, wherein:
$A_2$ is $CH_2$;
$R_9$ is hydrogen;
$R_{10}$ together with $R_{11}$ form =O;
$R_{12}$ together with $R_{13}$ form =O;
$R_3$ is hydrogen, $C_1$-$C_4$alkyl or $C_1$-$C_4$haloalkyl or $C_1$-$C_4$alkylthio-$C_1$-$C_4$alkyl;
$R_2$, $R_7$ and $R_8$ are hydrogen; and
Y is Y-1 or Y-4.

22. The composition of claim 11, wherein:
$A_2$ is $CH_2$;
$R_9$ is hydrogen;
$R_{10}$ together with $R_{11}$ form =O;
$R_{12}$ together with $R_{13}$ form =O;
$R_3$ is hydrogen, $C_1$-$C_4$alkyl or $C_1$-$C_4$haloalkyl or $C_1$-$C_4$alkylthio-$C_1$-$C_4$alkyl;
$R_3$, $R_7$ and $R_8$ are hydrogen; and
Y is Y-1 or Y-4.

23. The composition of claim 9, wherein:
$A_2$ is $CH_2$;
$R_9$ is hydrogen;
$R_{10}$ together with $R_{11}$ form =O;
$R_{12}$ together with $R_{13}$ form =O;
$R_3$ is $C_1$-$C_4$haloalkyl or $C_1$-$C_4$-alkylthio-$C_1$-$C_4$-alkyl;
$R_2$, $R_7$ and $R_8$ are hydrogen; and
Y is Y-1 or Y-4.

24. The composition of claim 23, wherein:
Y is Y-1; and
$R_3$ is —$CH_2CH_2SCH_3$.

25. The composition of claim 23, wherein:
Y is Y-4; and
$R_3$ is —$CH_2CF_3$.

26. The composition of claim 1, wherein the compound of formula (I) is a compound of of formula 1.001 to 1.025:

1.001 to 1.025 wherein Z, p, $B^1$, $B^2$, $B^3$, $B^4$, $B^5$, $R^{15}$ and $R^{16}$ are:

| Compound No. | $(Z)_p$ | $B^5$ | $B^4$ | $B^3$ | $B^2$ | $B^1$ | $R^{15}$ | $R^{16}$ |
|---|---|---|---|---|---|---|---|---|
| 1.001 | 3,5-$Cl_2$ | C—H | C—H | C—H | C—H | N | H | $CH_2C(O)NHCH_2CF_3$ |
| 1.002 | 3,5-$Cl_2$ | C—H | C—H | C—H | C—H | N | H | $CH_2CF_3$ |
| 1.003 | 3,5-$(CF_3)_2$ | C—H | C—H | C—H | C—H | N | $CH_3$ | $CH_2CO_2CH_3$ |
| 1.004 | 3,5-$(CF_3)_2$ | C—H | C—H | C—H | C—H | N | $CH_3$ | $CH_2CO_2H$ |
| 1.005 | 3,5-$(CF_3)_2$ | C—H | C—H | C—H | C—H | N | $CH_3$ | $CH_2C(O)NHCH_2CF_3$ |
| 1.006 | 3,5-$(CF_3)_2$ | C—H | C—H | C—H | C—H | N | H | $CH_2C(O)NHCH_2CF_3$ |
| 1.007 | 3,5-$(CF_3)_2$ | C—H | C—H | C—H | C—H | N | H | $CH_2CH_2SCH_3$ |
| 1.008 | 3,5-$(CF_3)_2$ | C—H | C—H | C—H | C—H | C—H | H | $CH_2C(O)NHCH_2CF_3$ |
| 1.009 | 3,5-$(CF_3)_2$ | C—H | C—H | C—H | C—H | C—H | H | $CH_2CH_2SCH_3$ |
| 1.010 | 3,5-$(CF_3)_2$ | C—H | C—H | C—H | C—H | C—H | H | $CH_2CF_3$ |
| 1.011 | 3,5-$Cl_2$ | C—H | C—H | C—H | C—H | C—H | H | $CH_2C(O)NHCH_2CF_3$ |
| 1.012 | 3,5-$Cl_2$ | C—H | C—H | C—H | C—H | C—H | H | $CH_2CF_3$ |
| 1.013 | 3,5-$Cl_2$ | C—H | C—H | C—H | C—H | C—H | H | $CH_2CH_2SCH_3$ |
| 1.014 | 3-Cl,5-$CF_3$ | C—H | C—H | C—H | C—H | C—H | H | $CH_2C(O)NHCH_2CF_3$ |
| 1.015 | 3-Cl,5-$CF_3$ | C—H | C—H | C—H | C—H | C—H | H | $CH_2CF_3$ |
| 1.016 | 3-Cl,5-$CF_3$ | C—H | C—H | C—H | C—H | C—H | H | $CH_2CH_2SCH_3$ |
| 1.017 | 3,5-$Cl_2$ | C—H | C—H | C—Me | C—H | C—Me | H | $CH_2C(O)NHCH_2CF_3$ |
| 1.018 | 3,5-$Cl_2$ | C—H | C—H | C—Me | C—H | C—Me | H | $CH_2CF_3$ |
| 1.019 | 3,5-$Cl_2$ | C—H | C—H | C—Me | C—H | C—Me | H | $CH_2CH_2SCH_3$ |
| 1.020 | 3,5-$(CF_3)_2$ | C—H | C—H | C—Me | C—H | C—Me | H | $CH_2C(O)NHCH_2CF_3$ |
| 1.021 | 3,5-$(CF_3)_2$ | C—H | C—H | C—Me | C—H | C—Me | H | $CH_2CF_3$ |
| 1.022 | 3,5-$(CF_3)_2$ | C—H | C—H | C—Me | C—H | C—Me | H | $CH_2CH_2SCH_3$ |
| 1.023 | 3-Cl,5-$CF_3$ | C—H | C—H | C—Me | C—H | C—Me | H | $CH_2C(O)NHCH_2CF_3$ |
| 1.024 | 3-Cl,5-$CF_3$ | C—H | C—H | C—Me | C—H | C—Me | H | $CH_2CF_3$ or |
| 1.025 | 3-Cl,5-$CF_3$ | C—H | C—H | C—Me | C—H | C—Me | H | $CH_2CH_2SCH_3$. |

27. The composition of claim 1, wherein the compound of formula (I) is a compound of of formula 2.001 to 1.018:

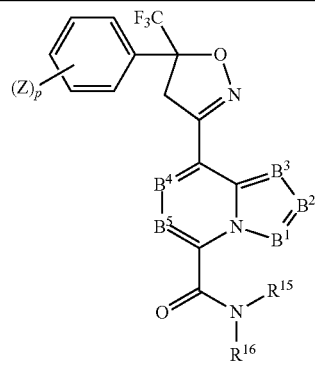

2.001 to 2.018 wherein Z, p, $B^1$, $B^2$, $B^3$, $B^4$, $B^5$, $R^{15}$ and $R^{16}$ are:

| Compound No. | $(Z)_p$ | $B^5$ | $B^4$ | $B^3$ | $B^2$ | $B^1$ | $R^{15}$ | $R^{16}$ |
|---|---|---|---|---|---|---|---|---|
| 2.001 | 3,5-$Cl_2$ | C—H | C—H | N | C—H | C—H | H | $CH_2C(O)NHCH_2CF_3$ |
| 2.002 | 3,5-$Cl_2$ | C—H | C—H | N | C—H | C—H | H | $CH_2CF_3$ |
| 2.003 | 3,5-$Cl_2$ | C—H | C—H | N | C—H | C—H | H | $CH_2CH_2SCH_3$ |
| 2.004 | 3,5-$(CF_3)_2$ | C—H | C—H | N | C—H | C—H | H | $CH_2C(O)NHCH_2CF_3$ |
| 2.005 | 3,5-$(CF_3)_2$ | C—H | C—H | N | C—H | C—H | H | $CH_2CF_3$ |
| 2.006 | 3,5-$(CF_3)_2$ | C—H | C—H | N | C—H | C—H | H | $CH_2CH_2SCH_3$ |
| 2.007 | 3-Cl,5-$CF_3$ | C—H | C—H | N | C—H | C—H | H | $CH_2C(O)NHCH_2CF_3$ |
| 2.008 | 3-Cl,5-$CF_3$ | C—H | C—H | N | C—H | C—H | H | $CH_2CF_3$ |
| 2.009 | 3-Cl,5-$CF_3$ | C—H | C—H | N | C—H | C—H | H | $CH_2CH_2SCH_3$ |
| 2.010 | 3,5-$Cl_2$ | C—H | C—H | C—H | C—H | C—H | H | $CH_2C(O)NHCH_2CF_3$ |
| 2.011 | 3,5-$Cl_2$ | C—H | C—H | C—H | C—H | C—H | H | $CH_2CF_3$ |
| 2.012 | 3,5-$Cl_2$ | C—H | C—H | C—H | C—H | C—H | H | $CH_2CH_2SCH_3$ |
| 2.013 | 3,5-$(CF_3)_2$ | C—H | C—H | C—H | C—H | C—H | H | $CH_2C(O)NHCH_2CF_3$ |
| 2.014 | 3,5-$(CF_3)_2$ | C—H | C—H | C—H | C—H | C—H | H | $CH_2CF_3$ |
| 2.015 | 3,5-$(CF_3)_2$ | C—H | C—H | C—H | C—H | C—H | H | $CH_2CH_2SCH_3$ |
| 2.016 | 3-Cl,5-$CF_3$ | C—H | C—H | C—H | C—H | C—H | H | $CH_2C(O)NHCH_2CF_3$ |
| 2.017 | 3-Cl,5-$CF_3$ | C—H | C—H | C—H | C—H | C—H | H | $CH_2CF_3$ |
| 2.018 | 3-Cl,5-$CF_3$ | C—H | C—H | C—H | C—H | C—H | H | $CH_2CH_2SCH_3$. |

28. The composition of claim 1, wherein the animal is a cat, a dog or cattle.

29. The composition of claim 1, wherein the parasites are ticks or fleas.

* * * * *